US008153765B2

(12) United States Patent
Park et al.

(10) Patent No.: US 8,153,765 B2
(45) Date of Patent: Apr. 10, 2012

(54) ANTI-CD38 ANTIBODIES FOR THE TREATMENT OF CANCER

(75) Inventors: Peter U. Park, Somerville, MA (US); Laura M. Bartle, Arlington, MA (US); Anna Skaletskaya, Cambridge, MA (US); Viktor Golmakher, Newton, MA (US); Daniel Tavares, Natick, MA (US); Jutta Deckert, Lexington, MA (US); Vincent Mikol, Paris (FR); Veronique Blanc, Paris (FR)

(73) Assignee: Sanof Aventis, Paris (FR)

( * ) Notice: Subject to any disclaimer, the term of this patent is extended or adjusted under 35 U.S.C. 154(b) by 234 days.

(21) Appl. No.: 12/441,466

(22) PCT Filed: Oct. 16, 2007

(86) PCT No.: PCT/IB2007/004172
§ 371 (c)(1),
(2), (4) Date: Aug. 10, 2009

(87) PCT Pub. No.: WO2008/047242
PCT Pub. Date: Apr. 24, 2008

(65) Prior Publication Data
US 2009/0304710 A1    Dec. 10, 2009

(30) Foreign Application Priority Data
Oct. 19, 2006  (EP) ..................... 06291628

(51) Int. Cl.
*C12P 21/08* (2006.01)
(52) U.S. Cl. .................. 530/387.3; 530/350; 530/387.1; 530/388.2; 530/388.7; 530/388.8; 530/389.1; 530/389.6; 530/389.7; 530/391.3; 530/391.7; 435/334
(58) Field of Classification Search .......... 530/350, 530/387.1, 387.3, 388.2, 388.7, 388.8, 389.1, 530/389.6, 389.7, 391.3, 391.7; 435/334
See application file for complete search history.

(56) References Cited

U.S. PATENT DOCUMENTS

| | | | |
|---|---|---|---|
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,444,887 A | 4/1984 | Hoffmann |
| 4,450,254 A | 5/1984 | Isley et al. |
| 4,716,111 A | 12/1987 | Osband et al. |
| 4,816,397 A | 3/1989 | Boss et al. |
| 4,816,567 A | 3/1989 | Cabilly et al. |
| 4,946,778 A | 8/1990 | Ladner et al. |
| 5,223,409 A | 6/1993 | Ladner et al. |
| 5,258,498 A | 11/1993 | Huston et al. |
| 5,403,484 A | 4/1995 | Ladner et al. |
| 5,416,064 A | 5/1995 | Chari et al. |
| 5,427,908 A | 6/1995 | Dower et al. |
| 5,475,092 A | 12/1995 | Chari et al. |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,571,698 A | 11/1996 | Ladner et al. |
| 5,580,717 A | 12/1996 | Dower et al. |
| 5,585,089 A | 12/1996 | Queen et al. |
| 5,585,499 A | 12/1996 | Chari et al. |
| 5,639,641 A | 6/1997 | Pedersen et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,807,715 A | 9/1998 | Morrison et al. |
| 5,814,318 A | 9/1998 | Lonberg et al. |

(Continued)

FOREIGN PATENT DOCUMENTS

EP    0 239 400    9/1987

(Continued)

OTHER PUBLICATIONS

Michaelsen et al. (Eur. J. Immunol. Jan. 1991; 21 (1): 11-6).*

(Continued)

*Primary Examiner* — Stephen Rawlings

(57) ABSTRACT

Antibodies, humanized antibodies, resurfaced antibodies, antibody fragments, derivatized antibodies, and conjugates of same with cytotoxic agents, which specifically bind to CD38, are capable of killing CD38$^+$ cells by apoptosis, antibody-dependent cell-mediated cytotoxicity (ADCC), and/or complement-dependent cytotoxicity (CDC). Said antibodies and fragments thereof may be used in the treatment of tumors that express CD38 protein, such as multiple myeloma, chronic lymphocytic leukemia, chronic myelogenous leukemia, acute myelogenous leukemia, or acute lymphocytic leukemia, or the treatment of autoimmune and inflammatory diseases such as systemic lupus, rheumatoid arthritis, multiple sclerosis, erythematosus, and asthma. Said derivatized antibodies may be used in the diagnosis and imaging of tumors that express elevated levels of CD38. Also provided are cytotoxic conjugates comprising a cell binding agent and a cytotoxic agent, therapeutic compositions comprising the conjugate, methods for using the conjugates in the inhibition of cell growth and the treatment of disease, and a kit comprising the cytotoxic conjugate. In particular, the cell binding agent is a monoclonal antibody, and epitope-binding fragments thereof, that recognizes and binds the CD38 protein.

30 Claims, 20 Drawing Sheets

U.S. PATENT DOCUMENTS

| | | | |
|---|---|---|---|
| 5,821,047 | A | 10/1998 | Garrard et al. |
| 5,846,545 | A | 12/1998 | Chari et al. |
| 5,969,108 | A | 10/1999 | McCafferty et al. |
| 6,333,410 | B1 | 12/2001 | Chari et al. |
| 6,340,701 | B1 | 1/2002 | Chari et al. |
| 6,436,931 | B1 | 8/2002 | Chari et al. |
| 6,534,660 | B1 | 3/2003 | Yongxin et al. |
| 6,586,618 | B1 | 7/2003 | Zhao et al. |
| 6,596,757 | B1 | 7/2003 | Chari et al. |
| 6,630,579 | B2 | 10/2003 | Chari et al. |
| 6,706,708 | B2 | 3/2004 | Chari et al. |
| 6,716,821 | B2 | 4/2004 | Zhao et al. |
| 6,756,397 | B2 | 6/2004 | Zhao et al. |
| 7,223,397 | B1 * | 5/2007 | Rosenblum et al. ........ 424/178.1 |
| 7,276,497 | B2 | 10/2007 | Chari et al. |
| 7,329,760 | B2 | 2/2008 | Zhao et al. |
| 7,538,195 | B2 * | 5/2009 | Singh et al. ................ 530/387.3 |
| 7,732,131 | B2 * | 6/2010 | Moretta et al. ..................... 435/5 |
| 7,816,543 | B2 * | 10/2010 | Bouchard et al. ............. 549/293 |
| 7,850,962 | B2 * | 12/2010 | Teeling et al. ............. 424/130.1 |
| 7,851,432 | B2 * | 12/2010 | Chari et al. ........................ 514/1 |
| 2003/0235582 | A1 | 12/2003 | Singh et al. |
| 2005/0118183 | A1 | 6/2005 | Hoffee et al. |
| 2009/0123950 | A1 * | 5/2009 | Tesar .......................... 435/7.23 |

FOREIGN PATENT DOCUMENTS

| | | |
|---|---|---|
| EP | 0 332 424 | 9/1989 |
| EP | 0 338 745 | 10/1989 |
| EP | 0 519 596 | 12/1992 |
| EP | 0 592 106 | 4/1994 |
| EP | 1 331 266 | 7/2003 |
| EP | 1 498 490 | 1/2005 |
| EP | 1 498 491 | 1/2005 |
| EP | 1 676 910 | 7/2006 |
| EP | 1 792 987 | 6/2007 |
| EP | 1 864 682 | 12/2007 |
| WO | WO 89/09622 | 10/1989 |
| WO | WO 90/02809 | 3/1990 |
| WO | WO 91/09967 | 7/1991 |
| WO | WO 91/10737 | 7/1991 |
| WO | WO 91/10741 | 7/1991 |
| WO | WO 92/01047 | 1/1992 |
| WO | WO 92/18619 | 10/1992 |
| WO | WO 96/16990 | 6/1996 |
| WO | WO 98/46645 | 10/1998 |
| WO | WO 98/50433 | 11/1998 |
| WO | WO 99/54342 | 10/1999 |
| WO | WO 00/12508 | 3/2000 |
| WO | WO 00/40265 | 7/2000 |
| WO | WO 03/074679 | 9/2003 |
| WO | WO 2004/029207 | 4/2004 |
| WO | WO 2004/099249 | 11/2004 |
| WO | WO 2005/040170 | 5/2005 |
| WO | WO 2005/103083 | 11/2005 |
| WO | WO 2006/019447 | 2/2006 |
| WO | WO 2006/099875 | 9/2006 |
| WO | WO 2006/105338 | 10/2006 |
| WO | WO 2007/041635 | 4/2007 |
| WO | WO 2007/085930 | 8/2007 |

OTHER PUBLICATIONS

Lucisano Valim et al. (Clin. Exp. Immunol. Apr. 1991; 84 (1): 1-8).*
Rudikoff et al (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Winkler et al. (J. Immunol. Oct. 15, 2000: 165 (8): 4505-4514).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Ellis et al (J. Immunol. Jul. 15, 1995; 155 (2): 925-37).*
Lewis et al. (Cancer Immunol. Immunother. Sep. 1993; 37 (4): 255-63).*
Kipps et al. (J. Exp. Med. Jan. 1, 1985; 161 (1): 1-17).*
Zupo et al. (Eur. J. Immunol. May 1994; 24 (5): 1218-22).*
Cellular and Molecular Immunology (Eds. Abass et al.; 1991; W.B. Saunders: Philadelphia; p. 54).*
Ausiello et al., Functional topography of discrete domains of human CD38, Tissue Antigens, vol. 56, 2000 pp. 539-547.
Basi et al., New Humanized antibodies that rcognize beta amyloid peptides, Database EMBL Dec. 16, 2004, Database Accession No. ADR88440, XP002442066.
Beavers et al., Monoclonal antibody containing recombinant DNA, Database EMBL Mar. 25, 2003, Accession No. AAQ10379 XP002442057.
Better et al., *Escherichia coli* Secretion of an Active Chimeric Antibody Fragment, Science, vol. 240, 1988, pp. 1041-1043.
Bhaskar et al., New Antibody that competitively inhibits binding of TMEFF219 to TMEFF2, Database EMBL Dec. 18, 2003, Accession No. ADC27440 XP002442058.
Bhuyan et al., CC-1065 (NCS 298223), a Most Potent Antitumor Agent: Kinetics of inhibition of Growth, DNA Synthesis and Cell Survival, Cancer Research. vol. 42, Sep. 1982, pp. 3532-3537.
Biffis et al., Highly Efficient Alkyne Hydroarylation with Chelating Dicarbene Palladium (II) and Platinum (II) Complexes, Adv. Synth. Catal. vol. 350, 2008, 189-196.
Boder et al., Directed evolution of antibody fragments with monovalent femtomolar antigen-binding affinity, PNAS, vol. 97, Sep. 2000, pp. 10701-10705.
Boger et al., Synthesis of N-(tert-Butyloxycarbonyl)-CBI, CABI. CBI-CDPI1 and CAB-CDPI2, J. Org. Chem., vol. 55, 1990, pp. 5823-5833.
Boger et al., Synthesis and Preliminary Evaluation of (+)-CBI-INDOLE2: An Enhanced Functional Analog of (+)-CC-1065, BioOrg. Med. Chem Lett. vol. 1, pp. 115-120.
Brinkmann et al., Phage Display of disulfide-stabilized Fv fragments, J. of Immunol. Methods, vol. 182, 1995, pp. 41-50.
Burton et al., Human Antibodies From Combinatorial Libraries, Advances in Immunology, vol. 57, 1994, pp.191-280.
Byrne et al., The Structure of anti-Gal immunoglobulin genes in naïve and stimulated Gal knockout mice, Database EMBL Apr. 18, 2002, Database Accession No. AY090904, XP002442065.
Carlsson et al., Protein Thiolation and Reversible Protein-Protein Conjugation, Biochem. J. vol. 173, 1978, pp. 723-737.
Chari et al., Enhancement of the Selectivity and Antitumor Efficacy of a CC-1065 Analogue through Immunoconjugate, Cancer Research, vol. 55, Sep. 1995, pp. 4079-4084.
Dagher et al., c-Kit and CD38 are expressed by long-term reconstituting hematopoletic cell present in the murine yolk sac, Biology of Blood and Marrow Transplantation, vol. 4, 1998, pp. 69-74.
Davies et al., Affinity improvement of single antibody VH domains: residues in all three hypervariable, immunotechnology, vol. 2, Issue 3, Sep. 1996, pp. 169-179.
Deaglio et al., CD38 is a signaling molecule in B-cell chronic lymphocytic leukemia cells, Blood, vol. 102, 2003, pp. 2146-2155.
Ferrara et al., Modulation of Therapeutic Antibody Effector Functions by Glycosylation Engineering: Influence of Golgi Enzyme Localization Domain, Biotechnology & Bioengineerin vol. 93, Iss. 5, Apr. 5, 2006, pp. 851-861.
Foster et al., Phase I trial of Adozelesin using the treatment schedule of daily x5 every 3 weeks; Investigational New Drugs, vol. 13, 1996, pp. 321-326.
Funaro et al., Human CD38 is associated to distinct molecules which mediate transmembrane signaling in different lineages: Eur. J. of Immunol, vol. 23, 1993, pp. 2407-2411.
Funaro et al, Involvement of the multilineage CD38 molecule in a unique pathway of cell activation and proliferation, J. of Immunol, vol. 145, 1990, pp. 2390-2396.

Furukawa et al., A Role of the Third Complementarity-determining Region in the Affinity Maturation of an Antibody, J. of Biol. Chem.. vol. 276, Jul. 20, 2001, pp. 27622-27628.

Gazzano-Santoro et al., A non-radioactive complement-dependent cytotoxicity assay for anti CD20 monoclonal antibody, J. of Immunol. Methods, vol. 202, 1997, pp. 163-171.

Ghezzi et al., Uptake of antitumor platinum(II)-complexes by cancer cells, assayed by inductively coupled plasma mass spectrometry (ICP-MS), J. of Inorganic Biochemistry, vol. 98, 2004, pp. 73078.

Gillies et al., High-level expression of chimeric antibodies using adapted cDNA variable region cassettes, J. of Immunol. Methods, vol. 125, 1989, pp. 191-202.

Goldmacher et al., Antibody-complement-mediated cytotoxicity is enhanced by ribosome-inactivating proteins, J. Immunol. vol. 135, 1985, pp. 3648-3651.

Goldmacher et al., Evidence that pinocytosis in lymphoid cells has a low capacity, J. Immunol. vol. 135, 1985, pp. 3648-3651.

Gram et al., In vitro selection and affinity maturation of antibodies from a naive combinatorial, PNAS, vol. 89, Apr. 1992, pp. 3576-3580.

Hoshino et al., Mapping of the catalytic and epitopic sites of human CD38/Nad+ glycohydrolase to a functional domain in the carboxyl terminus, J. of Immunology, 1997, vol. 158, pp. 741-747.

Hudson, P.J., Recombinant antibody constructs in cancer therapy, Current Opinion in immunology. vol. 11, 1999, pp. 548-557.

Huston et al., Protein Engineering of Single-Chain Fv Analogs and Fusion Proteins, Methods in Enzymology, vol. 203, 1991, pp. 46-88.

Kalesse et al., The Chemistry and Biology of the Leptomycin Family, Synthesis, vol. 8, 2002, pp. 981-1003.

Kearney et al., A New Mouse Myeloma Cell Line That has Lost immunoglobulin Expression But Permiet the Construction of Antibody-Secreting Hybrid Cell Lines, J. of Immunol. vol. 123, 1979, pp. 1548-1550.

Kitanka et al., CD38 ligation in human B cell progenitors triggers tyrosine phosphorylation of CD19 with lyn and phosphatidylinositol 3-kinase, J. of Immunol. vol. 159, 1997, pp. 184-192.

Kitanka et al., CD38-Mediated Signaling Events in Murine Pro-B Cells Expressing Human CD38 With or Without Its Cytoplasmic Domain, J. of Immunol., vol. 162, 1999, pp. 1952-1958.

Konopleva et al, Ligation of Cell Surface CD38 Protein with Agnostic Monoclonal antibody induces a Cell Growth Signal in Myeloid Leukemia Cells, J. of Immunolgy, vol. 161, 1998, pp. 4702-4703.

Kovala-Demertzi et al., Platinum (II) and palladium (II) complexes with 2-Acetyl pyridine 4N-ethyl thiosemicarbazone able to overcome the cis-Platin resistance, Biometals, vol. 16, 2003, pp. 411-418.

Kumagai et al., Ligation of CD38 Suppresses Human B Lymphopoiesis, J. of Exp, Med., vol. 181, 1995, pp. 11101-1110.

Lazar et al, Engineered antibody Fc variants with enhanced effector function, PNAS, vol. 103, No. 11, 2006, pp. 4005-4010.

Lee et al., Structural Determination of a Cyclic Metabolite of NAD+ With Intracellular Ca2+-mobilizing Activity, J. of Biol. Chem., vol. 264, Jan. 25, 1989, pp. 1608-1615.

Lee et al., ADP-ribosyl cyclase: an enzyme that cyclizes NAD+ into a calcium-mobilizing metabolite. Cell Regulation, vol. 2, Mar. 1991, pp. 203-209.

Lee et al., ADP-ribosyl cycle and CD38. Multifunctional enzymes in Ca+2 signaling, Adv. Exp. Med. Biol, 1997, vol. 419, pp. 411-419.

Liu et al., Eradication of large colon tumor xenografts by targeted delivery of maytansinoids, PNAS, vol. 93, Aug. 1996, pp. 8618-8623.

Lund et al., CD38 Signaling in by Lymphocytes Is Controlled by Its Ectodomain but Occurs Independently of Ezymatically Generated ADP-Ribose or Cyclic ADP-Ribose, J. of Immunology, 1999, vol. 162, pp. 2693-2702.

Lustgarten et al., The response to a foreign antigen in the autoimmune NZB/W F1 murine strain, Database EMBL May 4, 2000, Database Accession No, L16832, XP00244059.

Ma et al., Humanised anti-HER2 monoclonal antibody and its preparation, Database EMBL Jul. 15, 2004, Database Accession No. AD057830, XP02442064.

Mallone et al., Signaling through CD38 induces NK cell activation, Int. Immunol. vol. 13, 2001, pp. 397-409.

Mori et al., Total Syntheses of Prothracarcin and Tomaymycin by Use of Palladium Catalyzed Carbonylation; Tetrahedron, vol. 42, 1986, pp. 3793-3806.

Morra et al., CD38 is functionally dependent on the TCR/CD3 complex in human cells, FASEB J., vol. 12, 1998, pp. 581-592.

Morrison, S.L., Transfectomas Provide Novel Chimeric Antibodies, Science, vol. 229, 1985, pp. 1202-1207.

Mullinax et al., Expression of heterodimeric Fab antibody protein in one cloning step, Biotechniques, vol. 12, No. 6, Jun. 1992, pp. 864-869.

Nisonoff et al., Separation of Univalent Fragments from the Bivalent Rabbit Antibody Molecule by Reduction of Disulfide Bonds, Arch. of Biochem. & Biophy. vol. 89, 1960, pp. 230-244.

Oliver et al., Mouse CD38 is down-regulated on germinal center B cells and mature plasma cells, J. of Immunology, vol. 158, 1997, pp. 1108-1115.

Padlan, E.A., A Possible Procedure for Reducing the Immunogenicity of Antibody Variable Domains While Preserving Their Ligand-Binding Properties, Molecular Immunology, vol. 28. No. 4/5 1991, pp. 489-498.

Parham, P., On the fragmentation of monoclonal IgG1, IgG2a and IgG2b from BALB/c mice, J. of Immunol. vol. 131, 1983, pp. 2895-2902.

Partida-Sanchez et al., Regulation of Dendritic Cell Trafficking by the ADP-Ribosyl Cyclase CD38: Impact on the Development of Humoral Immunity, Immunity, vol. 20, Mar. 2004, pp. 279-291.

Partida-Sanchez et al., Cyclic ADP-ribose production by CD38 regulates intracellular calcium release, exctracellular calcium influx and chemotaxis in neutrophils and is required for bacterial clearance in vivo, Nature Medicine, vol. 7, 2001, pp. 1209-1216.

Pearson et al., Improved tools for biological sequence comparison, PNAS, vol. 85, 1988, pp. 2444-2448.

Persic et al., An integrated vector system for the eukaryotic expression of antibodies or their fragments after selection from phage display libraries, Gene, vol. 187, Issue 1, Mar. 1997, pp. 9018.

Rader et al., A phage display approach for rapid antibody humanization: Designed combinatorial V gene libraries, PNAS, vol. 95, Jul. 1998, pp. 8910-8915.

Randall et al., Expression of Murine CD38 Defines a Population of Long-Term Reconstituting Hematopoietic Stem Cells, Blood, vol. 87, 1996, pp. 4057-4067.

Ray et al., Anticancer and Antimicrobial Metallopharmaceutical Agents Based on Palladium, Gold, and Silver N-Heterocyclic Carbene Complexes, J. Am Chem Soc. vol. 129, 2007, pp. 15042-15053.

Reth et al., Regulated progression of a cultured pre-B-cell line to the B-cell stage, Nature, vol. 317, 1985, pp. 353-355.

Reynolds et al., The Chemistry, Mechanism of Action and Biological Properties of CC-1065, A Potent Antitumor Antibiotic. J. of Antibiotics, Mar. 1988, pp. 319-334.

Ridderstad et al., Kinetics of Establishing the Memory B Cell Population as Revealed by CD38 Expression, J. of Immunology, vol. 160, 1998, pp. 4688-4695.

Roguska et al., Humanization of murine monoclonal antibodies through variable domain resurfacing, PNAS, vol. 91, 1994, pp. 969-973.

Sawai et al., Direct production of the Fab fragment derived from the sperm immobilizing antibody using polymerase chain reaction and cDNA expression vectors, Am. J. of Reproductive Immunology, vol. 34, Issue 1, Jul. 1995, pp. 26-34.

Shields et al., High Resolution Mapping of the Binding Site on Human IgG1 For FcγRI, FcγRII, FcγRIII,and RcRn and Design of IgG1 Variants with Improved Bindig to the FcγR, J. of Biol. Chem., vol. 275, 2001, pp. 6591-6604.

Shinkawa et al., The Absence of Fucose but Not the Presence of Galactose or Bisecting N-Acetylglucosamine of Human IgG1 Complex-type Antibody-dependent Cellular Cytotoxity, J. of Biol. Chem., vol. 278, No. 5, Jan. 31, 2003, pp. 3466-3473.

Short et al., Complementary Combining Site Contact Residue Mutations of the Anti-digoxin Fab 26-10 Permit High Affinity Wild-type Binding, J. of Biol. Chem., vol. 277, May 10, 277, pp. 16365-16370.

Shu et al., Secretion of a single-gene-encoded immunoglobin from myeloma cells, PNAS, vol. 90, Sep. 1993, pp. 7995-7999.

Spring et al., Allotypic Markers on Fab Fragments of Mouse Immunoglodulins, J. of Immunol. vol. 113, 1974, pp. 470-478.

Stevenson et al., Preliminary Studies for an Immunotherapeutic Approach to the Treatment of Human Myeloma Using Chimeric Anti-CD38 Antibody, Blood, vol. 77, 1991, pp. 1071-1079.

Studnicka et al., Human-engineered monoclonal antibodies retain full specific binding activity by preserving non-CDR complementarity-modulating residues, Protein Engineering Design & Selection, vol. 7. No. 6, 1994, pp. 805-814.

Thompson et al., Affinity Maturation of a High-affinity Human Monoclonal Antibody Against the Thrid Hypervariable Loop, J. of Mol. Biol., vol. 256, Issue 1, Feb. 1996, pp. 77-88.

Thornton et al., Prediction of progress at last, Nature, vol. 354, 1991, pp. 105-106.

Todisco et al., CD38 ligation inhibits normal and leukemic myelopoiesis. Blood, vol. 15 2000. pp. 535-542.

Tozuka et al., Studies on Tomaymycin II, J. of Antibiotics, vol. 36, Mar. 1983, pp. 276-282.

Uckun, F.M., Regulation of Human B-Cell Ontogeny, Blood, vol. 76, 1990, pp. 1908-1923.

Van De Winkel et al., HuMax CD38, a Potential Novel Immunotherapy for the Treatment of Patients with Multiple Myeloma, 6th International Congress on Monoclonal Antibodies in Cancer, Aug. 2006, Washington DC.

Vaughan et al., Human antibodies by design, Nature Biotechnology, vol. 16, 1998, pp. 535-539.

Warpehoski et al., Stereoelectronic Factors Influencing the Biological Activity and DNA Interaction of Synthetic Antitumor Agents on CC-1065, J. of Medicinal Chemistry, vol. 31, 1988, pp. 590-603.

Winter et al., Man-made antibodies, Nature, vol. 349, 1991, pp. 293-299.

Wolff et al., Phase I Clinical and Pharmacokinetic Study of Carzelesin (U-80244) Given Daily for 5 Consecutive Days, Clin. Cancer Res. vol. 2, Oct. 1996, pp. 1717-1723.

Yang et al., CDR Walking Mutagenesis for the Affinity Maturation of a Potent Human Anti-HIV-1 Antibody into the Picomolar Range, J. Mol. Biol. vol. 254, 1995, pp. 392-403.

Zilber et al., CD38 expressed on human monocytes: A coaccessory molecule in the superantigen-induced proliferation, PNAS, vol. 97, 2000, pp. 2840-2845.

Zubiaur et al., CD38 Ligation Results in Activation of the Raf-1/Mitogen-Activated Protein Kinase and the CD3-S/S-Associated Protein-70 Signaling Pathways in Jurkat T Lymphocytes, J. of Immunol., vol. 159, 1997, pp. 193-205.

Zupo et al., CD38 signaling by agonistic monoclonal antibody prevents apoptosis of human germinal center B cells, Eur. J. of Immunol, vol. 24, 1994, pp. 1218-1222.

Oi et al., Chimeric Antibodies, BioTechniques, vol. 4, 1986, p. 214.

Skerra et al., Assembly of a Functional Immunoglobulin Fv Fragment in *Escherichia coli*, Science, vol. 240, 1988, pp. 1038-1040.

Konopleva et al., Stromal cells prevent apoptosis of AML cells by up-regulation of anti-apoptotic proteins, Leukemia, vol. 16, No. 9, Sep. 2002, pp. 1713-1724.

Erickson et al., Antibody-Maytaninoid Conjugates Are Activated in Targeted Cancel Cells by Lysosomal Degradation and Linker-Dependent Intracellular Processing, Cancer Research, Apr. 15, 2006, pp. 4426-4433.

Ojima et al., Tumor-specific novel taxoid-monoclonal antibody conjugates, J. of Med. Chem., vol. 45, No. 26, Dec. 19, 2002, pp. 5620-5623.

Clarke et al., Inter- and Intraional Diversity in the Antibody Response to Influenza Hemagglutinin, J. of Exp. Med. vol. 161, Apr. 1985, pp. 687-704.

Inoue et al, Anti-human IgE monoclonal antibody, Feb. 8, 2002, XP002442051, Database Accession No. E40596.

Chua et al., Germ-Line Affinity and Germ-Line Variable Region Genes in the B Cell Response. J. of Immunology, vol. 138, No. 4, Feb. 15, 1987 pp. 1281-1299.

Harvey et al., Antibodies with increased affinities for anthrax antigens, Aug. 31, 2006, XP002442063, Database Accession No. AR696413.

Lutz et al., Eradication of acute myeloid leukemia tumor xenografts by an anti-CD33-DM1 immunoconjugate, Proceedings of the Amer. Assoc For Cancer Research, vol. 43, Mar. 2002, p. 912.

Goldmacher et al., Anti-CD-38-blocked ricin: An immunotoxin for the treatment of multiple myeloma, Blood, vol. 84, No. 9, 1994, pp. 3017-3025.

Ellis et al., Engineered anti-CD38 monoclonal antibodies for immunotherapy of multiple myeloma, J. of Immunology, vol. 155, No. 2, 1995, pp. 925-937.

Fantasia et al., Electronic Properties of N-Heterocyclic Carbene (NHC) Ligands; Synthetic, Structural, and Spectroscopic Studies of (NHC) Platinum (II) Complexes, Organometallics, 2007, vol. 26, pp. 5880-5889.

Ferrara et al., The Carbohydrate at Fc RIIIa yAsn-162, An Element Reqiured for High Affinity Binding to Non-Fucosylated IgG Glycoforms, J. of Biol. Chem. Feb. 24, 2006, vol. 281, No. 8, pp. 5032-5036.

* cited by examiner

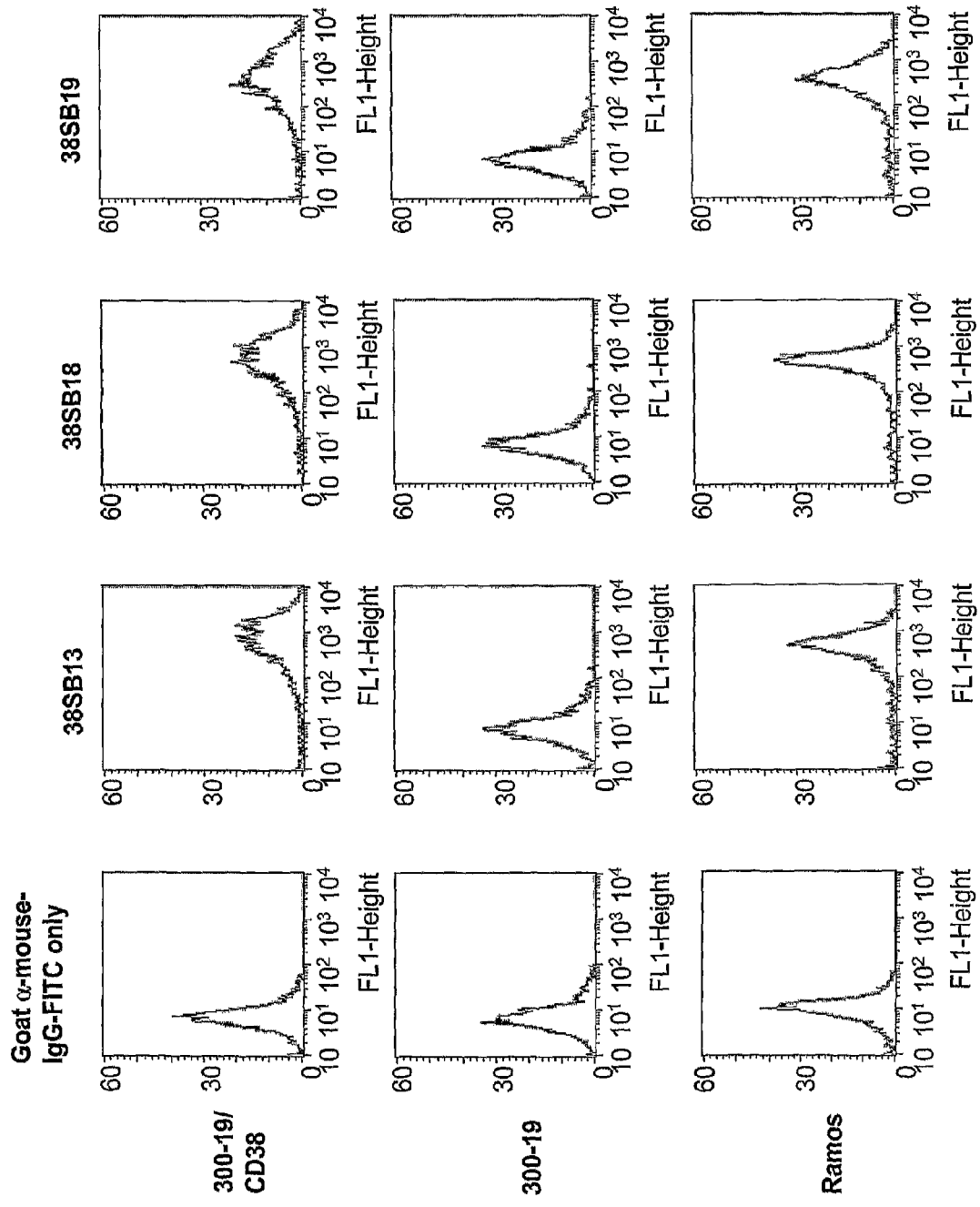

Relative Mean Fluorescence

Relative Mean Fluorescence

ANTI-CD38 ANTIBODIES FOR THE TREATMENT OF CANCER

BACKGROUND OF THE INVENTION

CD38 is a 45 kD type II transmembrane glycoprotein with a long C-terminal extracellular domain and a short N-terminal cytoplasmic domain. The CD38 protein is a bifunctional ectoenzyme that can catalyze the conversion of $NAD^+$ into cyclic ADP-ribose (cADPR) and also hydrolyze cADPR into ADP-ribose. During ontogeny, CD38 appears on $CD34^+$ committed stem cells and lineage-committed progenitors of lymphoid, erythroid and myeloid cells. CD38 expression persists mostly in the lymphoid lineage with varying expression levels at different stages of T and B cell development.

CD38 is upregulated in many hematopoeitic malignancies and in cell lines derived from various hematopoietic malignancies, including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). On the other hand, most primitive pluripotent stem cells of the hematopoietic system are $CD38^-$. CD38 expression in hematopoietic malignancies and its correlation with disease progression makes CD38 an attractive target for antibody therapy.

CD38 has been reported to be involved in $Ca^{2+}$ mobilization (M. Morra et al., 1998, *FASEB J.*, 12: 581-592; M. T. Zilber et al., 2000, *Proc Natl Acad Sci USA*, 97: 2840-2845) and in the signal transduction through tyrosine phosphorylation of numerous signaling molecules, including phospholipase C-γ, ZAP-70, syk, and c-cbl, in lymphoid and myeloid cells or cell lines (A. Funaro et al., 1993, *Eur J Immunol*, 23: 2407-2411; M. Morra et al., 1998, *FASEB J.*, 12: 581-592; A. Funaro et al., 1990, *J Immunol*, 145: 2390-2396; M. Zubiaur et al., 1997, *J Immunol*, 159: 193-205; S. Deaglio et al., 2003, *Blood* 102: 2146-2155; E. Todisco et al., 2000, *Blood*, 95: 535-542; M. Konopleva et al., 1998, *J Immunol*, 161: 4702-4708; M. T. Zilber et al., 2000, *Proc Natl Acad Sci USA*, 97: 2840-2845; A. Kitanaka et al., 1997, *J Immunol*, 159: 184-192; A. Kitanaka et al., 1999, *J Immunol*, 162: 1952-1958; R. Mallone et al., 2001, *Int Immunol*, 13: 397-409). On the basis of these observations, CD38 was proposed to be an important signaling molecule in the maturation and activation of lymphoid and myeloid cells during their normal development.

The exact role of CD38 in signal transduction and hematopoiesis is still not clear, especially since most of these signal transduction studies have used cell lines ectopically overexpressing CD38 and anti-CD38 monoclonal antibodies, which are non-physiological ligands. Because the CD38 protein has an enzymatic activity that produces cADPR, a molecule that can induce $Ca^{2+}$ mobilization (H. C. Lee et al., 1989, *J Biol Chem*, 264:1608-1615; H. C. Lee and R. Aarhus, 1991, *Cell Regul*, 2: 203-209), it has been proposed that CD38 ligation by monoclonal antibodies triggers $Ca^{2+}$ mobilization and signal transduction in lymphocytes by increasing production of cADPR (H. C. Lee et al., 1997, *Adv Exp Med Biol*, 419: 411-419). Contrary to this hypothesis, the truncation and point-mutation analysis of CD38 protein showed that neither its cytoplasmic tail nor its enzymatic activity is necessary for the signaling mediated by anti-CD38 antibodies (A. Kitanaka et al., 1999, *J Immunol*, 162: 1952-1958; F. E. Lund et al., 1999, *J Immunol*, 162: 2693-2702; S. Hoshino et al., 1997, *J Immunol*, 158, 741-747).

The best evidence for the function of CD38 comes from $CD38^{-/-}$ knockout mice, which have a defect in their innate immunity and a reduced T-cell dependent humoral response due to a defect in dendritic cell migration (S. Partida-Sanchez et al., 2004, *Immunity*, 20: 279-291; S. Partida-Sanchez et al., 2001, *Nat Med*, 7: 1209-1216). Nevertheless, it is not clear if the CD38 function in mice is identical to that in humans since the CD38 expression pattern during hematopoiesis differs greatly between human and mouse: a) unlike immature progenitor stem cells in humans, similar progenitor stem cells in mice express a high level of CD38 (T. D. Randall et al., 1996, *Blood*, 87: 4057-4067; R. N. Dagher et al., 1998, *Biol Blood Marrow Transplant*, 4: 69-74), b) while during the human B cell development, high levels of CD38 expression are found in germinal center B cells and plasma cells (F. M. Uckun, 1990, *Blood*, 76: 1908-1923; M. Kumagai et al., 1995, *J Exp Med*, 181: 1101-1110), in the mouse, the CD38 expression levels in the corresponding cells are low (A. M. Oliver et al., 1997, *J Immunol*, 158: 1108-1115; A. Ridderstad and D. M. Tarlinton 1998, *J Immunol*, 160: 4688-4695).

Several anti-human CD38 antibodies with different proliferative properties on various tumor cells and cell lines have been described in the literature. For example, a chimeric OKT10 antibody with mouse Fab and human IgG1 Fc mediates antibody-dependent cell-mediated cytotoxicity (ADCC) very efficiently against lymphoma cells in the presence of peripheral blood mononuclear effector cells from either MM patients or normal individuals (F. K. Stevenson et al., 1991, *Blood*, 77: 1071-1079). A CDR-grafted humanized version of the anti-CD38 antibody AT13/5 has been shown to have potent ADCC activity against CD38-positive cell lines (U.S. Ser. No. 09/797,941 A1). Human monoclonal anti-CD38 antibodies have been shown to mediate the in vitro killing of CD38-positive cell lines by ADCC and/or complement-dependent cytotoxicity (CDC), and to delay the tumor growth in SCID mice bearing MM cell line RPMI-8226 (WO2005/103083 A2). On the other hand, several anti-CD38 antibodies, IB4, SUN-4B7, and OKT10, but not IB6, AT1, or AT2, induced the proliferation of peripheral blood mononuclear cells (PBMC) from normal individuals (C. M. Ausiello et al. 2000, *Tissue Antigens*, 56: 539-547).

Some of the antibodies of the prior art have been shown to be able to trigger apoptosis in $CD38^+$ B cells. However, they can only do so in the presence of stroma cells or stroma-derived cytokines. An agonistic anti-CD38 antibody (IB4) has been reported to prevent apoptosis of human germinal center (GC) B cells (S. Zupo et al. 1994, *Eur J Immunol*, 24:1218-1222), and to induce proliferation of KG-1 and HL-60 AML cells (M. Konopleva et al. 1998, *J Immunol*, 161: 4702-4708), but induces apoptosis in Jurkat T lymphoblastic cells (M. Morra et al. 1998, *FASEB J*, 12: 581-592). Another anti-CD38 antibody T16 induced apoptosis of immature lymphoid cells and leukemic lymphoblast cells from an ALL patient (M. Kumagai et al. 1995, *J Exp Med*, 181: 1101-1110), and of leukemic myeloblast cells from AML patients (E. Todisco et al. 2000, *Blood*, 95: 535-542), but T16 induced apoptosis only in the presence of stroma cells or stroma-derived cytokines (IL-7, IL-3, stem cell factor).

On the other hand, some prior art antibodies induce apoptosis after cross-linking, but are totally devoid of any apoptotic activity when incubated alone (WO 2006/099875).

Because CD38 is an attractive target for antibody therapy for various hematopoietic malignancies, we generated and screened a large number of anti-human CD38 antibodies for high potency in the following three cytotoxic activities against CD38-positive malignant hematopoietic cells: induction of apoptosis, ADCC, and CDC. The present invention describes novel anti-CD38 antibodies capable of killing CD38+ cells by three different cytotoxic mechanisms: induction of apoptosis, ADCC, and CDC. Remarkably, the present invention discloses the first anti-CD38 antibodies that are able to directly induce apoptosis of CD38+ cells, even without the presence of stroma cells or stroma-derived cytokines.

SUMMARY OF THE INVENTION

It is an object of the invention to provide antibodies specifically binding CD38, and capable of killing CD38+ cells by apoptosis. Whereas some prior art antibodies are able to trigger apoptosis only when crosslinked, but are otherwise devoid of any apoptotic activity, the antibodies of the invention are capable of inducing apoptotic cell death of CD38+ cells even when incubated alone. In one aspect of the invention, the antibodies of the invention are capable of killing CD38+ B cells by ADCC or CDC. In yet another aspect, the antibodies of the invention are capable of killing CD38+ cell by at least two of the aforementioned mechanisms, i.e. apoptosis, ADCC, and CDC. Remarkably, the antibodies of the invention are the first anti-CD38 antibodies that have been demonstrated to kill CD38+ B cells by all three different mechanisms: apoptosis, ADCC, and CDC. In a further embodiment of the invention, said antibodies are capable of killing CD38+ B cells by apoptosis even in the absence of stroma cells or stroma-derived cytokines.

The antibodies of the invention are capable in particular of killing malignant CD38+ B cells, including lymphoma cells, leukemia cells, and multiple myeloma cells. In some embodiments, the CD38+ B cell is a NHL, BL, MM, B-CLL, ALL, TCL, AML, HCL, HL, or CML cell.

In one aspect of the invention, the antibodies of the invention are capable of killing at least 24% of Daudi lymphoma cells and/or at least 7% of Ramos lymphoma cells and/or 11% of MOLP-8 multiple myeloma cells and/or 36% of SU-DHL-8 lymphoma cells and/or 62% of DND-41 leukemia cells and/or 27% of NU-DUL-1 lymphoma cells and/or 9% of JVM-13 leukemia cells and/or 4% of HC-1 leukemia cells by apoptosis in the absence of stroma cells or stroma-derived cytokines.

Antibodies of the invention can be polyclonal or monoclonal. Preferred are monoclonal anti-CD38 antibodies. In a more preferred embodiment, there are provided murine antibodies selected from 38SB13, 38SB18, 38SB19, 38SB30, 38SB31, and 38SB39, which are fully characterized herein with respect to the amino acid sequences of both their light and heavy chain variable regions, the cDNA sequences of the genes for the light and heavy chain variable regions, the identification of their CDRs (complementarity-determining regions), the identification of their surface amino acids, and means for their expression in recombinant form.

The present invention includes chimeric versions of the murine anti-CD38 monoclonal antibody selected from 38SB13, 38SB18, 38SB19, 38SB30, 38SB31, and 38SB39. Also included are resurfaced or humanized versions of the 38SB13, 38SB18, 38SB19, 38SB30, 38SB31, and 38SB39 antibodies wherein surface-exposed residues of the variable region frameworks of the antibodies, or their epitope-binding fragments, are replaced in both light and heavy chains to more closely resemble known human antibody surfaces. The humanized antibodies and epitope-binding fragments thereof of the present invention have improved properties in that they are less immunogenic (or completely non-immunogenic) than murine versions in human subjects to which they are administered. Thus, the different versions of humanized 38SB13, 38SB18, 38SB19, 38SB30, 38SB31, and 38SB39 antibodies and epitope-binding fragments thereof of the present invention specifically recognize CD38 while not being immunogenic to a human.

The humanized versions of the 38SB13, 38SB18, 38SB19, 38SB30, 38SB31, and 38SB39 antibodies of the present invention are fully characterized herein with respect to their respective amino acid sequences of both light and heavy chain variable regions, the DNA sequences of the genes for the light and heavy chain variable regions, the identification of the complementarity determining regions (CDRs), the identification of their variable region framework surface amino acid residues, and disclosure of a means for their expression in recombinant form.

This invention also contemplates the use of conjugates between cytotoxic conjugates comprising (1) a cell binding agent that recognizes and binds CD38, and (2) a cytotoxic agent. In the cytotoxic conjugates, the cell binding agent has a high affinity for CD38 and the cytotoxic agent has a high degree of cytotoxicity for cells expressing CD38, such that the cytotoxic conjugates of the present invention form effective killing agents.

In a preferred embodiment, the cell binding agent is an anti-CD38 antibody (e.g., 38SB13, 38SB18, 38SB19, 38SB30, 38SB31, and 38SB39) or an epitope-binding fragment thereof, more preferably a humanized anti-CD38 antibody (e.g., 38SB13, 38SB18, 38SB19, 38SB30, 38SB31, and 38SB39) or an epitope-binding fragment thereof, wherein a cytotoxic agent is covalently attached, directly or via a cleavable or non-cleavable linker, to the antibody or epitope-binding fragment thereof. In more preferred embodiments, the cell binding agent is the humanized 38SB13, 38SB18, 38SB19, 38SB30, 38SB31, and 38SB39 antibodies or an epitope-binding fragment thereof, and the cytotoxic agent is a Taxol® (paclitaxel), a maytansinoid, a tomaymycin derivative, a leptomycin derivative, CC-1065 or a CC-1065 analog.

More preferably, the cell binding agent is the humanized anti-CD38 antibody 38SB13, 38SB18, 38SB19, 38SB30, 38SB31, and 38SB39, and the cytotoxic agent is a maytansine compound, such as DM1 or DM4.

The present invention also encompasses the use of fragments of anti-CD38 antibodies which retain the ability to bind CD38. In another aspect of the invention, the use of functional equivalents of anti-CD38 antibodies is contemplated.

The present invention also includes a method for inhibiting the growth of a cell expressing CD38. In preferred embodiments, the method for inhibiting the growth of the cell expressing CD38 takes place in vivo and results in the death of the cell, although in vitro and ex vivo applications are also included.

The present invention also provides a therapeutic composition comprising an anti-CD38 antibody or an anti-CD38 antibody-cytotoxic agent conjugate, and a pharmaceutically acceptable carrier or excipients. In some embodiments, the therapeutic composition comprises a second therapeutic agent. This second therapeutic agent can be chosen from the group comprising the antagonists of epithermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP) or vascular endothelial growth factor (VEGF), or an antagonist of a receptor for epidermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP), or vascular endothelial growth factor (VEGF), including HER2 receptor, HER3 receptor, c-MET, and other receptor tyrosine kinases. This second therapeutic agent can be also chosen from the group comprising of antibodies targeting clusters of differentiation (CD) antigens, including CD3, CD14, CD19, CD20, CD22, CD25, CD28, CD30, CD33, CD36, CD40, CD44, CD52, CD55, CD59, CD56, CD70, CD79, CD80, CD103, CD134, CD137, CD138, and CD152. This second therapeutic agent can be also chosen from the group of chemotherapeutic or immunomodulatory agents.

The present invention further includes a method of treating a subject having a cancer or an inflammatory disease, including autoimmune disease using the therapeutic composition. In some embodiments, the cancer is selected from a group consisting of NHL, BL, MM, B-CLL, ALL, TCL, AML, HCL, HL, and CML. In another embodiment, the autoimmune disease is selected from a group consisting of systemic lupus erythematosus, multiple sclerosis, rheumatoid arthritis, Crohn's disease, ulcerative colitis, gastritis, Hashimoto's thyroiditis, ankylosing spondylitis, hepatitis C-associated cryoglobulinemic vasculitis, chronic focal encephalitis, bullous pemphigoid, hemophilia A, membranoproliferative glomerulonephritis, Sjogren's syndrome, adult and juvenile dermatomyositis, adult polymyositis, chronic urticaria, primary biliary cirrhosis, idiopathic thrombocytopenic purpura, neuromyelitis optica, Graves' dysthyroid disease, bullous pemphigoid, membranoproliferative glomerulonephritis, Churg-Strauss syndrome, and asthma. In preferred embodiments, the cytotoxic conjugate comprises an anti-CD38 antibody and a cytotoxic agent. In more preferred embodiments, the cytotoxic conjugate comprises a humanized 38SB13, 38SB18, 38SB19, 38SB30, 38SB31, and 38SB39 antibody-DM1 conjugate, humanized 38SB13, 38SB18, 38SB19, 38SB30, 38SB31, and 38SB39 antibody-DM4 or a humanized 38SB13, 38SB18, 38SB19, 38SB30, 38SB31, and 38SB39 antibody-taxane conjugate, and the conjugate is administered along with a pharmaceutically acceptable carrier or excipients.

In another aspect of the invention, anti-CD38 antibodies are used to detect the CD38 protein in a biological sample. In a preferred embodiment, said antibodies are used to determine CD38 levels in tumor tissue.

The present invention also includes a kit comprising an anti-CD38 antibody or an anti-CD38 antibody-cytotoxic agent conjugate and instructions for use. In preferred embodiments, the anti-CD38 antibodies are the humanized 38SB13, 38SB18, 38SB19, 38SB30, 38SB31, and 38SB39 antibodies, the cytotoxic agent is a maytansine compound, such as DM1 or DM4, a tomaymycin derivative, a leptomycin derivative, or a taxane, and the instructions are for using the conjugates in the treatment of a subject having cancer. The kit may also include components necessary for the preparation of a pharmaceutically acceptable formulation, such as a diluent if the conjugate is in a lyophilized state or concentrated form, and for the administration of the formulation. Unless otherwise stated, all references and patents cited herein are incorporated by reference.

BRIEF DESCRIPTION OF THE FIGURES

FIG. 1A shows a FACS analysis of the specific binding of purified murine anti-CD38 antibodies, 38SB13, 38SB18, 38SB19, 38 to the 300-19 cells expressing human CD38 and CD38-positive Ramos lymphoma cells.

DETAILED DESCRIPTION OF THE INVENTION

Figure 1B:
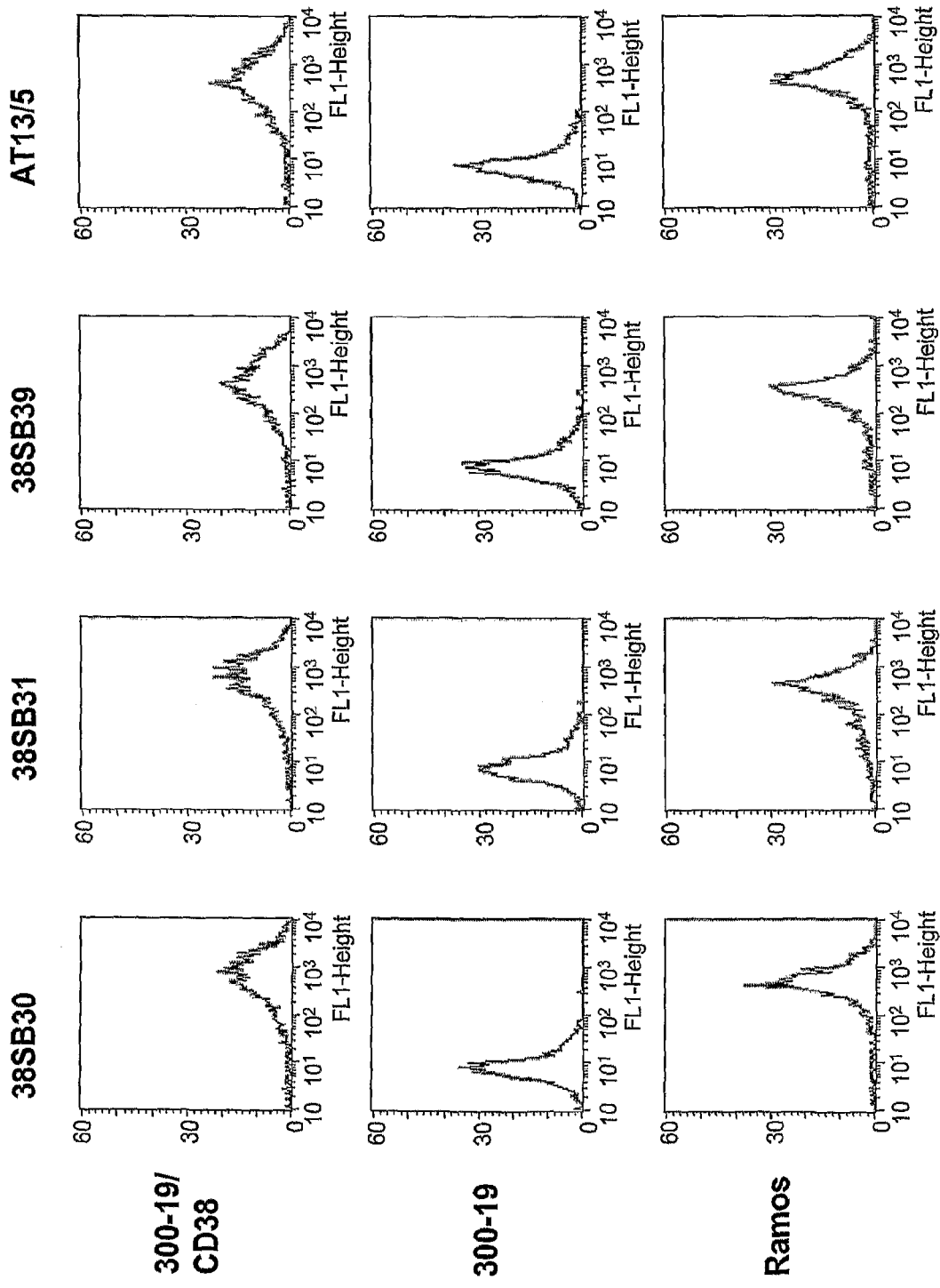
FIG. 1B shows a FACS analysis of the specific binding of purified murine anti-CD38 antibodies, 38SB30, 38SB31, 38SB39 and the control anti-CD38 antibody AT13/5 to the 300-19 cells expressing human CD38 and CD38-positive Ramos lymphoma cells.

New antibodies capable of specifically binding CD38 are herein provided. In particular, the present inventors have discovered novel antibodies that specifically bind to CD38 on the cell surface and kill CD38+ cells by apoptosis. In one aspect of the invention, the anti-CD38 antibodies are also capable of killing a CD38+ cell by antibody-dependent cytotoxicity (ADCC). In another aspect, the anti-CD38 antibodies of the invention are capable of killing a CD38+ cell by complement-dependent cytotoxicity (CDC). In yet another aspect, the anti-CD38 antibodies of the invention are capable of killing a CD38+ cell by at least two of the above mentioned mechanisms, apoptosis, ADCC, and CDC. In particular, in a preferred embodiment, the anti-CD38 antibodies of the invention are capable of killing a CD38+ cell by apoptosis, ADCC, and CDC. The invention thus provides the first anti-CD38 antibodies capable of killing a CD38+ cell by three different mechanisms.

Antibodies capable of binding CD38 and triggering apoptotic cell death in CD38+ cells have been previously described (M. Kumagai et al., 1995, *J Exp Med*, 181: 1101-1110; E. Todisco et al. 2000, *Blood*, 95: 535-542), but the antibodies of the invention are the first for which an apoptotic activity in the absence of stroma cells or stroma-derived cytokines is demonstrated. The term "stroma" as used herein refers to the nonmalignant supporting tissue of a tumor which includes connective tissue, blood vessels, and inflammatory cells. Stromal cells produce growth factors and other substances, including cytokines, that can influence the behavior of cancer cells. The term "cytokine", as used herein, refers to small secreted proteins (e.g. IL-1, IL-2, IL-4, IL-5, and IL-6, IFNg, IL-3, IL-7 and GM-CSF) which mediate and regulate immunity, inflammation, and hematopoiesis. It is shown herein that the antibodies of the prior art are unable to trigger apoptotic cell death in the absence of stroma cells or stroma-derived cytokines. By contrast, the anti-CD38 antibodies of the invention display under the same conditions potent apoptotic activities.

In another aspect, the antibodies of the invention are capable of binding the CD38 protein with a $k_D$ of $3 \times 10^{-9}$ M or lower.

The term "CD38" as used herein refers to a type II transmembrane protein, comprising, for example, an amino acid sequence as in Genbank accession number NP_001766. A "CD38+ cell" is a cell expressing the CD38 protein. Preferably, the CD38+ cell is a mammalian cell.

In one embodiment of this invention, the CD38+ cell is a malignant cell. In another embodiment, the CD38+ cell is a B cell. In a preferred embodiment, the CD38+ cell is a tumor cell derived from a hemopoietic malignancy. In a more preferred embodiment, the CD38+ cell is a lymphoma cell, a leukemia cell, or a multiple myeloma cell. In a further preferred embodiment, the CD38+ cell is a NHL, BL, MM, B-CLL, ALL, TCL, AML, HCL, HL, or CML cell.

Thus, in one embodiment, this invention provides anti-CD38 antibodies capable of killing at least 24% of Daudi lymphoma cells in the absence of stroma cells or stroma-derived cytokines. In another embodiment, the anti-CD38 antibodies of the invention are capable of killing at least 7% of Ramos lymphoma cells in the absence of stroma cells or stroma-derived cytokines. In another embodiment, the anti-CD38 antibodies of the invention are capable of killing at least 11% of MOLP-8 multiple myeloma cells in the absence of stroma cells or stroma-derived cytokines. In another embodiment, the anti-CD38 antibodies of the invention are capable of killing at least 36% of SU-DHL-8 lymphoma cells in the absence of stroma cells or stroma-derived cytokines. In another embodiment, the anti-CD38 antibodies of the invention are capable of killing at least 27% of NU-DUL-1 lymphoma cells in the absence of stroma cells or stroma-derived cytokines. In another embodiment, the anti-CD38 antibodies of the invention are capable of killing at least 62% of DND-41 leukemia cells in the absence of stroma cells or stroma-derived cytokines. In another embodiment, the anti-CD38 antibodies of the invention are capable of killing at least 9% of JVM-13 leukemia cells in the absence of stroma cells or stroma-derived cytokines. In another embodiment, the anti-CD38 antibodies of the invention are capable of killing at least 4% of HC-1 leukemia cells in the absence of stroma cells or stroma-derived cytokines.

Antibodies

The term "antibody" is used herein in the broadest sense and specifically covers monoclonal antibodies (including full length monoclonal antibodies) of any isotype such as IgG, IgM, IgA, IgD and IgE, polyclonal antibodies, multispecific antibodies, chimeric antibodies, and antibody fragments. An antibody reactive with a specific antigen can be generated by recombinant methods such as selection of libraries of recombinant antibodies in phage or similar vectors, or by immunizing an animal with the antigen or an antigen-encoding nucleic acid.

A typical IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDR1, CDR2, and CDR3, numbered sequentially from the N-terminus. The more highly conserved portions of the variable regions are called the "framework regions".

As used herein, "$V_H$" or "VH" refers to the variable region of an immunoglobulin heavy chain of an antibody, including the heavy chain of an Fv, scFv, dsFv, Fab, Fab' or F(ab')2 fragment. Reference to "$V_L$" or "VL" refers to the variable region of the immunoglobulin light chain of an antibody, including the light chain of an Fv, scFv, dsFv, Fab, Fab' or F(ab')2 fragment.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

A "monoclonal antibody", as used herein, is an antibody obtained from a population of substantially homogeneous antibodies, i.e. the antibodies forming this population are essentially identical except for possible naturally occurring mutations which might be present in minor amounts. These antibodies are directed against a single epitope and are therefore highly specific.

An "epitope" is the site on the antigen to which an antibody binds. If the antigen is a polymer, such as a protein or polysaccharide, the epitope can be formed by contiguous residues or by non-contiguous residues brought into close proximity by the folding of an antigenic polymer. In proteins, epitopes formed by contiguous amino acids are typically retained on exposure to denaturing solvents, whereas epitopes formed by non-contiguous amino acids are typically lost under said exposure.

As used herein, the term "$K_D$" refers to the dissociation constant of a particular antibody/antigen interaction.

The present invention proceeds from novel murine anti-CD38 antibodies, herein 38SB13, 38SB18, 38SB19, 38SB30, 38SB31, and 38SB39 which are fully characterized with respect to the amino acid sequences of both light and heavy chains, the identification of the CDRs, the identification of surface amino acids, and means for their expression in recombinant form. The primary amino acid and DNA sequences of antibodies 38SB13, 38SB18, 38SB19, 38SB30, 38SB31, and 38SB39 light and heavy chains, and of humanized versions, are disclosed herein.

The hybridoma cell lines producing the 38SB13, 38SB18, 38SB19, 38SB30, 38SB31, and 38SB39 murine anti-CD38 antibodies have been deposited at the American Type Culture Collection (10801 University Bld, Manassas, Va., 20110-2209, USA), on Jun. 21, 2006, under the deposit numbers PTA-7667, PTA-7669, PTA-7670, PTA-7666, PTA-7668, and PTA-7671, respectively.

The scope of the present invention is not limited to antibodies and fragments comprising these sequences. Instead, all antibodies and fragments that specifically bind to CD38 and capable of killing CD38+ cells by apoptosis, ADCC, and/or CDC, fall within the scope of the present invention. Thus, antibodies and antibody fragments may differ from antibody 38SB13, 38SB18, 38SB19, 38SB30, 38SB31, and 38SB39 or the humanized derivatives in the amino acid sequences of their scaffold, CDRs, light chain and heavy chain, and still fall within the scope of the present invention.

In one embodiment, this invention provides antibodies or epitope-binding fragment thereof comprising one or more CDRs having an amino acid sequence selected from the group consisting of SEQ ID NOS: 1, 2, 3, 4, 5, 6, 7, 8, 9, 10, 11, 12, 13, 81, 15, 16, 17, 18, 19, 20, 21, 22, 23, 24, 25, 26, 27, 28, 29, 30, 31, 32, 33, 34, 35, and 36. In a preferred embodiment, the antibodies of the invention comprise at least one heavy chain and at least one light chain, and said heavy chain comprises three sequential CDRs having amino acid sequences selected from the group consisting of SEQ ID NOS: 1, 2, 3, 7, 8, 9, 13, 81, 15, 19, 20, 21, 25, 26, 27, 31, 32, and 33, and said light chain comprises three sequential CDRs having amino acid sequences selected from the group consisting of SEQ ID NOS: 4, 5, 6, 10, 11, 12, 16, 17, 18, 22, 23, 24, 28, 29, 30, 34, 35, and 36.

In a more preferred embodiment, the antibodies of the invention comprise three CDRs having amino acid sequences selected from the group of SEQ ID NOS: 1, 2, 3, 4, 6, and 6. In a further more preferred embodiment, there is provided a 38SB13 antibody, which comprises at least one heavy chain and at least one light chain, and said heavy chain comprises three sequential CDRs having amino acid sequences consisting of SEQ ID NOS: 1, 2, and 3, and said light chain comprises three sequential CDRs having amino acid sequences consisting of SEQ ID NOS: 4, 5, and 6.

In another more preferred embodiment, the antibodies of the invention comprise three CDRs having amino acid sequences selected from the group of SEQ ID NOS: 7, 8, 9, 10, 11, and 12. In a further more preferred embodiment, there is provided a 38SB18 antibody, which comprises at least one heavy chain and at least one light chain, and said heavy chain comprises three sequential CDRs having amino acid sequences consisting of SEQ ID NOS: 7, 8, and 9, and said light chain comprises three sequential CDRs having amino acid sequences consisting of SEQ ID NOS: 10, 11, and 12.

In another more preferred embodiment, the antibodies of the invention comprise three CDRs having amino acid sequences selected from the group of SEQ ID NOS: 13, 81, 15, 16, 17, and 18. In a further more preferred embodiment, there is provided a 38SB19 antibody, which comprises at least one heavy chain and at least one light chain, and said heavy chain comprises three sequential CDRs having amino acid sequences consisting of SEQ ID NOS: 13, 81, and 15, and said light chain comprises three sequential CDRs having amino acid sequences consisting of SEQ ID NOS: 16, 17, and 18.

In another more preferred embodiment, the antibodies of the invention comprise three CDRs having amino acid sequences selected from the group of SEQ ID NOS: 19, 20, 21, 22, 23, 24. In a further more preferred embodiment, there is provided a 38SB30 antibody, which comprises at least one heavy chain and at least one light chain, and said heavy chain comprises three sequential CDRs having amino acid sequences consisting of SEQ ID NOS: 19, 20, and 21, and said light chain comprises three sequential CDRs having amino acid sequences consisting of SEQ ID NOS: 22, 23, and 24.

In another more preferred embodiment, the antibodies of the invention comprise three CDRs having amino acid sequences selected from the group of SEQ ID NOS: 25, 26, 27, 28, 29, and 30. In a further more preferred embodiment, there is provided a 38SB31 antibody, which comprises at least one heavy chain and at least one light chain, and said heavy chain comprises three sequential CDRs having amino acid sequences consisting of SEQ ID NOS: 25, 26, and 27, and said light chain comprises three sequential CDRs having amino acid sequences consisting of SEQ ID NOS: 28, 29, and 30.

In another more preferred embodiment, the antibodies of the invention comprise three CDRs having amino acid sequences selected from the group of 31, 32, 33, 34, 35, and 36. In a further more preferred embodiment, there is provided a 38SB39 antibody, which comprises at least one heavy chain and at least one light chain, and said heavy chain comprises three sequential CDRs having amino acid sequences consisting of SEQ ID NOS: 31, 32, and 33, and said light chain comprises three sequential CDRs having amino acid sequences consisting of SEQ ID NOS: 34, 35, and 36.

In another embodiment, the anti-CD38 antibodies of the invention comprise a $V_L$ having an amino acid sequence selected from the group consisting of SEQ ID NOS: $V_L$ for 38, 40, 42, 44, 46, and 48. In a more preferred embodiment, there is provided a 38SB13 antibody comprising a $V_L$ having an amino acid sequence consisting of SEQ ID NO: 38. In a more preferred embodiment, there is provided a 38SB18 antibody comprising a $V_L$ having an amino acid sequence consisting of SEQ ID NO: 40. In a more preferred embodiment, there is provided a 38SB19 antibody comprising a $V_L$ having an amino acid sequence consisting of SEQ ID NO: 42. In a more preferred embodiment, there is provided a 38SB30 antibody comprising a $V_L$ having an amino acid sequence consisting of SEQ ID NO: 44. In a more preferred embodiment, there is provided a 38SB31 antibody comprising a $V_L$ having an amino acid sequence consisting of SEQ ID NO: 46. In a more preferred embodiment, there is provided a 38SB39 antibody comprising a $V_L$ having an amino acid sequence consisting of SEQ ID NO: 48.

In another embodiment, the antibodies of the invention comprise a $V_H$ having having an amino acid sequence selected from the group consisting of SEQ ID NOS: 50, 52, 54, 56, 58, and 60. In a more preferred embodiment, there is provided a 38SB13 antibody comprising a $V_H$ having an amino acid sequence consisting of SEQ ID NO: 50. In a more preferred embodiment, there is provided a 38SB18 antibody comprising a $V_H$ having an amino acid sequence consisting of SEQ ID NO: 52. In a more preferred embodiment, there is provided a 38SB19 antibody comprising a $V_H$ having an amino acid sequence consisting of SEQ ID NO: 54. In a more preferred embodiment, there is provided a 38SB30 antibody comprising a $V_H$ having an amino acid sequence consisting of SEQ ID NO: 56. In a more preferred embodiment, there is provided a 38SB31 antibody comprising a $V_H$ having an amino acid sequence consisting of SEQ ID NO: 58. In a more preferred embodiment, there is provided a 38SB39 antibody comprising a $V_H$ having an amino acid sequence consisting of SEQ ID NO: 60.

Chimeric and Humanized 38SB13, 38SB18, 38SB19, 38SB30, 38SB31, and 38SB39 Antibodies As used herein, a "chimeric antibody" is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass. Methods for producing chimeric antibodies are known in the art. See, e.g., Morrison, 1985, *Science*, 229: 1202; Oi et al., 1986, *BioTechniques*, 4: 214; Gillies et al., 1989, *J. Immunol. Methods*, 125: 191-202; U.S. Pat. Nos. 5,807,715; 4,816,567; and 4,816,397, which are incorporated herein by reference in their entireties.

In one embodiment of the invention, chimeric versions of 38SB13, 38SB18, 38SB19, 38SB30, 38SB31, and 38SB39 are provided. In particular, said chimeric versions contain at least one human constant region. In a more preferred embodiment, this human constant region is the human IgG1/Kappa constant region.

The term "humanized antibody", as used herein, refers to a chimeric antibody which contain minimal sequence derived from non-human immunoglobulin. The goal of humanization is a reduction in the immunogenicity of a xenogeneic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. As used herein, the resurfacing technology uses a combination of molecular modeling, statistical analysis and mutagenesis to alter the non-CDR surfaces of antibody variable regions to resemble the surfaces of known antibodies of the target host. The CDR grafting technology involves substituting the complementarity determining regions of, for example, a mouse antibody, into a human framework domain, e.g., see WO 92/22653. Humanized chimeric antibodies preferably have constant regions and variable regions other than the complementarity determining regions (CDRS) derived substantially or exclusively from the corresponding human antibody regions and CDRs derived substantially or exclusively from a mammal other than a human.

Strategies and methods for the resurfacing of antibodies, and other methods for reducing immunogenicity of antibodies within a different host, are disclosed in U.S. Pat. No. 5,639,641, which is hereby incorporated in its entirety by reference. Briefly, in a preferred method, (1) position alignments of a pool of antibody heavy and light chain variable regions is generated to give a set of heavy and light chain variable region framework surface exposed positions wherein the alignment positions for all variable regions are at least about 98% identical; (2) a set of heavy and light chain variable region framework surface exposed amino acid residues is defined for a rodent antibody (or fragment thereof); (3) a set of heavy and light chain variable region framework surface exposed amino acid residues that is most closely identical to the set of rodent surface exposed amino acid residues is identified; (4) the set of heavy and light chain variable region framework surface exposed amino acid residues defined in step (2) is substituted with the set of heavy and light chain variable region framework surface exposed amino acid residues identified in step (3), except for those amino acid residues that are within 5 Å of any atom of any residue of the complementarity-determining regions of the rodent antibody; and (5) the humanized rodent antibody having binding specificity is produced.

Antibodies can be humanized using a variety of other techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., 1991, *Molecular Immunology* 28(415): 489-498; Studnicka G. M. et al., 1994, *Protein Engineering*, 7(6): 805-814; Roguska M. A. et al., 1994, *PNAS*, 91: 969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties).

The present invention provides humanized antibodies or fragments thereof, which recognize CD38 and kill CD38+ cells by apoptosis, ADCC, and/or CDC. In a further embodiment, the humanized antibodies or epitope-binding fragments thereof have the ability to kill said CD38+ cells by all three mechanisms. In yet another further embodiment, the humanized antibodies or epitope-binding fragments thereof of the invention are capable of killing said CD38+ cells by apoptosis even in the absence of stroma cells or stroma-derived cytokines.

A preferred embodiment of such a humanized antibody is a humanized 38SB13, 38SB18, 38SB19, 38SB30, 38SB31, or 38SB39 antibody, or an epitope-binding fragment thereof.

In more preferred embodiments, there are provided resurfaced or humanized versions of the 38SB13, 38SB18, 38SB19, 38SB30, 38SB31, and 38SB39 antibodies wherein surface-exposed residues of the antibody or its fragments are replaced in both light and heavy chains to more closely resemble known human antibody surfaces. The humanized 38SB13, 38SB18, 38SB19, 38SB30, 38SB31, and 38SB39 antibodies or epitope-binding fragments thereof of the present invention have improved properties. For example, humanized 38SB13, 38SB18, 38SB19, 38SB30, 38SB31, and 38SB39 antibodies or epitope-binding fragments thereof specifically recognize the CD38 protein. More preferably, the humanized 38SB13, 38SB18, 38SB19, 38SB30, 38SB31, and 38SB39 antibodies or epitope-binding fragments thereof have the additional ability to kill a CD38+ cell, by apoptosis, ADCC, and/or CDC.

The humanized versions of the 38SB13, 38SB18, 38SB19, 38SB30, 38SB31, and 38SB39 antibodies are also fully characterized herein with respect to their respective amino acid sequences of both light and heavy chain variable regions, the DNA sequences of the genes for the light and heavy chain variable regions, the identification of the CDRs, the identification of their surface amino acids, and disclosure of a means for their expression in recombinant form. However, the scope of the present invention is not limited to antibodies and fragments comprising these sequences. Instead, all antibodies and fragments that specifically bind to CD38 and are capable of killing CD38+ cells by apoptosis, ADCC and/or CDC fall within the scope of the present invention. Preferably, such antibodies are capable of killing CD38+ cells by all three mechanisms. Thus, antibodies and epitope-binding antibody fragments of the present invention may differ from the 38SB13, 38SB18, 38SB19, 38SB30, 38SB31, and 38SB39 antibodies or the humanized derivatives thereof, in the amino acid sequences of their scaffold, CDRs, and/or light chain and heavy chain, and still fall within the scope of the present invention.

The CDRs of the 38SB13, 38SB18, 38SB19, 38SB30, 38SB31, and 38SB39 antibodies are identified by modeling and their molecular structures have been predicted. Again, while the CDRs are important for epitope recognition, they are not essential to the antibodies and fragments of the invention. Accordingly, antibodies and fragments are provided that have improved properties produced by, for example, affinity maturation of an antibody of the present invention.

The sequences of the heavy chain and light chain variable regions of the 38SB13, 38SB18, 38SB19, 38SB30, 38SB31, and 38SB39 antibodies, and the sequences of their CDRs were not previously known and are set forth in this application. Such information can be used to produce humanized versions of the 38SB13, 38SB18, 38SB19, 38SB30, 38SB31, and 38SB39 antibodies. These humanized anti-CD38 antibodies or their derivatives may also be used as the cell binding agent of the present invention.

Thus, in one embodiment, this invention provides humanized antibodies or epitope-binding fragment thereof comprising one or more CDRs having an amino acid sequence selected from the group consisting of SEQ ID NOS: 1, 2, 3, 4, 5, 6, 7, 8, 9, 10, 11, 12, 13, 81, 15, 16, 17, 18, 19, 20, 21, 22, 23, 24, 25, 26, 27, 28, 29, 30, 31, 32, 33, 34, 35, and 36. In a preferred embodiment, the humanized antibodies of the invention comprise at least one heavy chain and at least one light chain, and said heavy chain comprises three sequential CDRs having amino acid sequences selected from the group consisting of SEQ ID NOS: 1, 2, 3, 7, 8, 9, 13, 81, 15, 19, 20, 21, 25, 26, 27, 31, 32, and 33, and said light chain comprises three sequential CDRs having amino acid sequences selected from the group consisting of SEQ ID NOS: 4, 5, 6, 10, 11, 12, 16, 17, 18, 22, 23, 24, 28, 29, 30, 34, 35, and 36. In a further preferred embodiment, a humanized version of 38S813 is provided, which comprises at least one heavy chain and at least one light chain, wherein said heavy chain comprises three sequential complementarity-determining regions having amino acid sequences represented by SEQ ID NOS: 1, 2, and 3, and wherein said light chain comprises three sequential complementarity-determining regions having amino acid sequences represented by SEQ ID NOS: 4, 5, and 6. In another further preferred embodiment, a humanized version of 38S818 is provided, which comprises at least one heavy chain and at least one light chain, wherein said heavy chain comprises three sequential complementarity-determining regions having amino acid sequences represented by SEQ ID NOS: 7, 8, and 9, and wherein said light chain comprises three sequential complementarity-determining regions having amino acid sequences represented by SEQ ID NOS: 10, 11, and 12. In another further preferred embodiment, a humanized version of 38SB19 is provided, which comprises at least one heavy chain and at least one light chain, wherein said heavy chain comprises three sequential complementarity-determining regions having amino acid sequences represented by SEQ ID NOS: 13, 81, and 15, and wherein said light chain comprises three sequential complementarity-determining regions having amino acid sequences represented by SEQ ID NOS: 16, 17, and 18. In another further preferred embodiment, a humanized version of 38SB30 is provided, which comprises at least one heavy chain and at least one light chain, wherein said heavy chain comprises three sequential complementarity-determining regions having amino acid sequences represented by SEQ ID NOS: 19, 20, and 21, and wherein said light chain comprises three sequential complementarity-determining regions having amino acid sequences represented by SEQ ID NOS: 22, 23, and 24. In another further preferred embodiment, a humanized version of 38SB31 is provided, which comprises at least one heavy chain and at least one light chain, wherein said heavy chain comprises three sequential complementarity-determining regions having amino acid sequences represented by SEQ ID NOS: 25, 26, and 27, and wherein said light chain comprises three sequential complementarity-determining regions having amino acid sequences represented by SEQ ID NOS: 28, 29, and 30. In another further preferred embodiment, a humanized version of 38SB39 is provided, which comprises at least one heavy chain and at least one light chain, wherein said heavy chain comprises three sequential complementarity-determining regions having amino acid sequences represented by SEQ ID NOS: 31, 32, and 33, and wherein said light chain comprises three sequential complementarity-determining regions having amino acid sequences represented by SEQ ID NOS: 34, 35, and 36.

In one embodiment, this invention provides humanized antibodies or fragments thereof which comprise a $V_H$ having an amino acid sequence selected from the group of SEQ ID NOS: 66 and 72. In a preferred embodiment, a humanized 38SB19 antibody is provided which comprises a $V_H$ having an amino acid sequence represented by SEQ ID NO: 66. In another preferred embodiment, a humanized 38SB31 antibody is provided which comprises a $V_H$ having an amino acid sequence represented by SEQ ID NO: 72.

In another embodiment, this invention provides humanized antibodies or fragments thereof which comprise a $V_L$ having an amino acid sequence selected from the group of SEQ ID NOS: 62, 64, 68, and 70. In a preferred embodiment, a humanized 38SB19 antibody is provided which comprises a $V_L$ having an amino acid sequence chosen from the group of SEQ ID NOS: 62 and 64. In another preferred embodiment, a humanized 38SB31 antibody is provided which comprises a $V_L$ having an amino acid sequence chosen from the group of SEQ ID NOS: 68 and 70.

The humanized 38SB19 antibodies and epitope-binding fragments thereof of the present invention can also include substitutions in light and/or heavy chain amino acid residues at one or more positions defined by the grey residues in Table 1A and 1B which represent the murine surface framework residues that have been changed from the original murine residue to the corresponding framework surface residue in the human antibody, 28E4. The starred (*) residues in Table 1B correspond to the murine back mutations in the humanized 38SB19 heavy chain variant (SEQ ID NO:65). The residues for back mutations are proximal to CDR's and were chosen as described in U.S. Pat. No. 5,639,641 or in analogy to the selection of residues that had in previous humanization efforts resulted in a decrease in antigen binding affinity (Roguska et al., 1996, U.S. patent application publications 2003/0235582 and 2005/0118183).

Likewise, the humanized 38SB13, 38SB18, 38SB30, 38SB31, and 38SB39 antibodies and epitope-binding fragments thereof of the present invention can also include substitution in light and/or heavy chain amino acid residues.

Polynucleotides, Vectors, and Host Cells

Nucleic acids encoding anti-CD38 antibodies of the invention are provided. In one embodiment, the nucleic acid molecule encodes a heavy and/or a light chain of an anti-CD38 immunoglobulin. In a preferred embodiment, a single nucleic acid encodes a heavy chain of an anti-CD38 immunoglobulin and another nucleic acid molecule encodes the light chain of an anti-CD38 immunoglobulin.

In another aspect of this invention, there are provided polynucleotides encoding polypeptides having an amino acid sequence selected from the group of SEQ ID NOS: 1, 2, 3, 4, 5, 6, 7, 8, 9, 10, 11, 12, 13, 81, 15, 16, 17, 18, 19, 20, 21, 22, 23, 24, 25, 26, 27, 28, 29, 30, 31, 32, 33, 34, 35, 36, 38, 40, 42, 44, 46, 48, 50, 52, 54, 56, 58, 60, 62, 64, 66, 68, 70, and 72. In a preferred embodiment, the polynucleotide of the invention is selected from the group consisting of SEQ ID NOs: 37, 39, 41, 43, 45, 47, 49, 51, 53, 55, 57, 59, 61, 63, 65, 67, 69, and 71. The invention is not limited to said polynucleotides per se but also includes all polynucleotides displaying at least 80% identity with said polynucleotides.

The invention provides vectors comprising the polynucleotides of the invention. In one embodiment, the vector contains a polynucleotide encoding a heavy chain of an anti-CD38 immunoglobulin. In another embodiment, said polynucleotide encodes the light chain of an anti-CD38 immunoglobulin. The invention also provides vectors comprising polynucleotide molecules encoding, fusion proteins, modified antibodies, antibody fragments, and probes thereof.

In order to express the heavy and/or light chain of the anti-CD38 antibodies of the invention, the polynucleotides encoding said heavy and/or light chains are inserted into expression vectors such that the genes are operatively linked to transcriptional and translational sequences. Expression vectors include plasmids, YACs, cosmids, retrovirus, EBV-derived episomes, and all the other vectors that the skilled man will know to be convenient for ensuring the expression of said heavy and/or light chains. The skilled man will realize that the polynucleotides encoding the heavy and the light chains can be cloned into different vectors or in the same vector. In a preferred embodiment, said polynucleotides are cloned in the same vector.

Polynucleotides of the invention and vectors comprising these molecules can be used for the transformation of a suitable mammalian host cell. Transformation can be by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

Antibody Fragments

The antibodies of the present invention include both the full length antibodies discussed above, as well as epitope-binding fragments thereof. As used herein, "antibody fragments" include any portion of an antibody that retains the ability to bind to the epitope recognized by the full length antibody, generally termed "epitope-binding fragments." Examples of antibody fragments include, but are not limited to, Fab, Fab' and F(ab')2, Fd, single-chain Fvs (scFv), single-chain antibodies, disulfide-linked Fvs (dsFv) and fragments comprising either a VL or VH region. Epitope-binding fragments, including single-chain antibodies, may comprise the variable region(s) alone or in combination with the entirety or a portion of the following: hinge region, CH1, CH2, and CH3 domains.

Such fragments may contain one or both Fab fragments or the F(ab')2 fragment. Preferably, the antibody fragments contain all six CDRs of the whole antibody, although fragments containing fewer than all of such regions, such as three, four or five CDRs, are also functional. Further, the fragments may be or may combine members of any one of the following immunoglobulin classes: IgG, IgM, IgA, IgD, or IgE, and the subclasses thereof.

Fab and F(ab')2 fragments may be produced by proteolytic cleavage, using enzymes such as papain (Fab fragments) or pepsin (F(ab')2 fragments).

The "single-chain FVs" ("scFvs") fragments are epitope-binding fragments that contain at least one fragment of an antibody heavy chain variable region ($V_H$) linked to at least one fragment of an antibody light chain variable region ($V_L$). The linker may be a short, flexible peptide selected to assure that the proper three-dimensional folding of the $V_L$ and $V_H$ regions occurs once they are linked so as to maintain the target molecule binding-specificity of the whole antibody from which the single-chain antibody fragment is derived. The carboxyl terminus of the $V_L$ or $V_H$ sequence may be covalently linked by a linker to the amino acid terminus of a complementary $V_L$ or $V_H$ sequence.

Single-chain antibody fragments of the present invention contain amino acid sequences having at least one of the variable or complementarity determining regions (CDRs) of the whole antibodies described in this specification, but lack some or all of the constant domains of those antibodies. These constant domains are not necessary for antigen binding, but constitute a major portion of the structure of whole antibodies. Single-chain antibody fragments may therefore overcome some of the problems associated with the use of antibodies containing a part or all of a constant domain. For example, single-chain antibody fragments tend to be free of undesired interactions between biological molecules and the heavy-chain constant region, or other unwanted biological activity. Additionally, single-chain antibody fragments are considerably smaller than whole antibodies and may therefore have greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely to provoke an immune response in a recipient than whole antibodies.

Single-chain antibody fragments may be generated by molecular cloning, antibody phage display library or similar techniques well known to the skilled artisan. These proteins may be produced, for example, in eukaryotic cells or prokaryotic cells, including bacteria. The epitope-binding fragments of the present invention can also be generated using various phage display methods known in the art. In phage display methods, functional antibody domains are displayed on the surface of phage particles which carry the polynucleotide sequences encoding them. In particular, such phage can be utilized to display epitope-binding domains expressed from a repertoire or combinatorial antibody library (e.g., human or murine). Phage expressing an epitope-binding domain that binds the antigen of interest can be selected or identified with antigen, e.g., using labeled antigen bound or captured to a solid surface or bead. Phage used in these methods are typically filamentous phage including fd and M13 binding domains expressed from phage with Fab, Fv or disulfide-stabilized Fv antibody domains recombinantly fused to either the phage gene III or gene VIII protein.

Examples of phage display methods that can be used to make the epitope-binding fragments of the present invention include those disclosed in Brinkman et al., 1995, *J. Immunol. Methods*, 182: 41-50; Ames et al., 1995, *J. Immunol. Methods*, 184:177-186; Kettleborough et al., 1994, *Eur. J. Immunol.*, 24: 952-958; Persic et al., 1997, *Gene*, 187: 9-18; Burton et al., 1994, *Advances in Immunology*, 57: 191-280; WO/1992/001047; WO 90/02809; WO 91/10737; WO 92/01047; WO 92118619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

After phage selection, the regions of the phage encoding the fragments can be isolated and used to generate the epitope-binding fragments through expression in a chosen host, including mammalian cells, insect cells, plant cells, yeast, and bacteria, using recombinant DNA technology, e.g., as described in detail below. For example, techniques to recombinantly produce Fab, Fab' and F(ab')2 fragments can also be employed using methods known in the art such as those disclosed in WO 92/22324; Mullinax et al., 1992, *BioTechniques*, 12(6): 864-869; Sawai et al., 1995, *AJRI*, 34: 26-34; and Better et al., 1988, *Science*, 240:1041-1043; said references incorporated by reference in their entireties. Examples of techniques which can be used to produce single-chain Fvs and antibodies include those described in U.S. Pat. Nos. 4,946,778 and 5,258,498; Huston et al., 1991, *Methods in Enzymology*, 203: 46-88; Shu et al., 1993, *PNAS*, 90: 7995-7999; Skerra et al., 1988, *Science*, 240:1038-1040.

Functional Equivalents

Also included within the scope of the invention are functional equivalents of the anti-CD38 antibody and the humanized anti-CD38 receptor antibody. The term "functional equivalents" includes antibodies with homologous sequences, chimeric antibodies, artificial antibodies and modified antibodies, for example, wherein each functional equivalent is defined by its ability to bind to the CD38 protein. The skilled artisan will understand that there is an overlap in the group of molecules termed "antibody fragments" and the group termed "functional equivalents." Methods of producing functional equivalents are known to the person skilled in the art and are disclosed, for example, in WO 93/21319, EP 239,400; WO 89/09622; EP 338,745; and EP 332,424, which are incorporated in their respective entireties by reference.

Antibodies with homologous sequences are those antibodies with amino acid sequences that have sequence homology with amino acid sequence of an anti-CD38 antibody and a humanized anti-CD38 antibody of the present invention. Preferably homology is with the amino acid sequence of the variable regions of the anti-CD38 antibody and humanized anti-CD38 antibody of the present invention. "Sequence homology" as applied to an amino acid sequence herein is defined as a sequence with at least about 90%, 91%, 92%, 93%, or 94% sequence homology, and more preferably at least about 95%, 96%, 97%, 98%, or 99% sequence homology to another amino acid sequence, as determined, for example, by the FASTA search method in accordance with Pearson and Lipman, 1988, *Proc. Natl. Acad. Sci. USA*, 85: 2444-2448.

Artificial antibodies include scFv fragments, diabodies, triabodies, tetrabodies and mru (see reviews by Winter, G. and Milstein, C., 1991, *Nature*, 349: 293-299; Hudson, P. J., 1999, *Current Opinion in Immunology*, 11: 548-557), each of which has antigen-binding ability. In the single chain Fv fragment (scFv), the $V_H$ and VL domains of an antibody are linked by a flexible peptide. Typically, this linker peptide is about 15 amino acid residues long. If the linker is much smaller, for example 5 amino acids, diabodies are formed, which are bivalent scFv dimers. If the linker is reduced to less than three amino acid residues, trimeric and tetrameric structures are formed that are called triabodies and tetrabodies. The smallest binding unit of an antibody is a CDR, typically the CDR2 of the heavy chain which has sufficient specific recognition and binding that it can be used separately. Such a fragment is called a molecular recognition unit or mru. Several such mrus can be linked together with short linker peptides, therefore forming an artificial binding protein with higher avidity than a single mru.

The functional equivalents of the present application also include modified antibodies, e.g., antibodies modified by the covalent attachment of any type of molecule to the antibody. For example, modified antibodies include antibodies that have been modified, e.g., by glycosylation, acetylation, pegylation, phosphorylation, amidation, derivatization by known protecting/blocking groups, proteolytic cleavage, linkage to a cellular ligand or other protein, etc. The covalent attachment does not prevent the antibody from generating an anti-idiotypic response. These modifications may be carried out by known techniques, including, but not limited to, specific chemical cleavage, acetylation, formylation, metabolic synthesis of tunicamycin, etc. Additionally, the modified antibodies may contain one or more non-classical amino acids.

Functional equivalents may be produced by interchanging different CDRs on different chains within different frameworks. Thus, for example, different classes of antibody are possible for a given set of CDRs by substitution of different heavy chains, whereby, for example, IgG1-4, IgM, IgA1-2, IgD, IgE antibody types and isotypes may be produced. Similarly, artificial antibodies within the scope of the invention may be produced by embedding a given set of CDRs within an entirely synthetic framework.

Functional equivalents may be readily produced by mutation, deletion and/or insertion within the variable and/or constant region sequences that flank a particular set of CDRs, using a wide variety of methods known in the art. The antibody fragments and functional equivalents of the present invention encompass those molecules with a detectable degree of binding to CD38, when compared to the 38SB13, 38SB18, 38SB19, 38SB30, 38SB31, or 38SB39 antibody. A detectable degree of binding includes all values in the range of at least 10-100%, preferably at least 50%, 60% or 70%, more preferably at least 75%, 80%, 85%, 90%, 95% or 99% of the binding ability of the murine 38SB13, 38SB18, 38SB19, 38SB30, 38SB31, or 38SB39 antibody to CD38.

Improved Antibodies

The CDRs are of primary importance for epitope recognition and antibody binding. However, changes may be made to the residues that comprise the CDRs without interfering with the ability of the antibody to recognize and bind its cognate epitope. For example, changes that do not affect epitope recognition, yet increase the binding affinity of the antibody for the epitope may be made.

Thus, also included in the scope of the present invention are improved versions of both the murine and humanized antibodies, which also specifically recognize and bind CD38, preferably with increased affinity.

Several studies have surveyed the effects of introducing one or more amino acid changes at various positions in the sequence of an antibody, based on the knowledge of the primary antibody sequence, on its properties such as binding and level of expression (Yang, W. P. et al., 1995, *J. Mol. Biol.*, 254: 392-403; Rader, C. et al., 1998, *Proc. Natl. Acad. Sci. USA*, 95: 8910-8915; Vaughan, T. J. et al., 1998, *Nature Biotechnology*, 16: 535-539).

In these studies, equivalents of the primary antibody have been generated by changing the sequences of the heavy and light chain genes in the CDR1, CDR2, CDR3, or framework regions, using methods such as oligonucleotide-mediated site-directed mutagenesis, cassette mutagenesis, error-prone PCR, DNA shuffling, or mutator-strains of *E. coli* (Vaughan, T. J. et al., 1998, *Nature Biotechnology*, 16: 535-539; Adey, N. B. et al., 1996, Chapter 16, pp. 277-291, in "Phage Display of Peptides and Proteins", Eds. Kay, B. K. et al., Academic Press). These methods of changing the sequence of the primary antibody have resulted in improved affinities of the secondary antibodies (Gram, H. et al., 1992, *Proc. Natl. Acad. Sci. USA*, 89: 3576-3580; Boder, E. T. et al., 2000, *Proc. Natl. Acad. Sci. USA*, 97: 10701-10705; Davies, J. and Riechmann, L., 1996, *Immunotechnolgy*, 2: 169-179; Thompson, J. et al., 1996, *J. Mol. Biol.*, 256: 77-88; Short, M. K. et al., 2002, *J. Biol. Chem.*, 277: 16365-16370; Furukawa, K. et al., 2001, *J. Biol. Chem.*, 276: 27622-27628).

By a similar directed strategy of changing one or more amino acid residues of the antibody, the antibody sequences described in this invention can be used to develop anti-CD38 antibodies with improved functions, including improved affinity for CD38.

Preferred amino acid substitutions are those which: (1) reduce susceptibility to proteolysis, (2) reduce susceptibility to oxidation, (3) alter binding affinity for forming protein complexes, and (4) confer or modify other physico-chemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain (s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al., 1991, *Nature*, 354: 105, which are each incorporated herein by reference.

Improved antibodies also include those antibodies having improved characteristics that are prepared by the standard techniques of animal immunization, hybridoma formation and selection for antibodies with specific characteristics.

Improved antibodies according to the invention include in particular antibodies with enhanced functional properties. Of special interest are those antibodies with enhanced ability to mediate cellular cytotoxic effector functions such as ADCC. Such antibodies may be obtained by making single or multiple substitutions in the constant framework of the antibody, thus altering its interaction with the Fc receptors. Methods for designing such mutants can be found for example in Lazar et al., (2006, *Proc. Natl. Acad. Sci. U.S.A.* 103(11): 4005-4010) and Okazaki et al. (2004, *J. Mol. Biol.* 336(5):1239-49). See also WO 03/074679, WO 2004/029207, WO 2004/099249, WO2006/047350, WO 2006/019447, WO 2006/105338, WO 2007/041635. It is also possible to use cell lines specifically engineered for production of improved antibodies. In particular, these lines have altered regulation of the glycosylation pathway, resulting in antibodies which are poorly fucosylated or even totally defucosylated. Such cell lines and methods for engineering them are disclosed in e.g. Shinkawa et al. (2003, *J. Biol. Chem.* 278(5): 3466-3473), Ferrara et al. (2006, *J. Biol. Chem.* 281(8): 5032-5036; 2006, *Biotechnol. Bioeng.* 93(5): 851-61), EP 1331266, EP 1498490, EP 1498491, EP 1676910, EP 1792987, and WO 99/54342.

The present invention also includes cytotoxic conjugates. These cytotoxic conjugates comprise two primary components, a cell-binding agent and a cytotoxic agent.

As used herein, the term "cell binding agent" refers to an agent that specifically recognizes and binds the CD38 proteins on the cell surface. In one embodiment, the cell binding agent specifically recognizes CD38 such that it allows the conjugates to act in a targeted fashion with little side-effects resulting from non-specific binding.

In another embodiment, the cell binding agent of the present invention also specifically recognizes the CD38 protein so that the conjugates will be in contact with the target cell for a sufficient period of time to allow the cytotoxic drug portion of the conjugate to act on the cell, and/or to allow the conjugates sufficient time in which to be internalized by the cell.

In a preferred embodiment, the cytotoxic conjugates comprise an anti-CD38 antibody as the cell binding agent, more preferably the murine 38SB13, 38SB18, 38SB19, 38SB30, 38SB31, or 38SB39 anti-CD38 monoclonal antibody. In another preferred embodiment, the cell binding agent is a chimeric version of said anti-CD38 antibody. In a more preferred embodiment, the cytotoxic conjugate comprises a humanized 38SB13, 38SB18, 38SB19, 38SB30, 38SB31, and 38SB39 antibody or an epitope-binding fragment thereof. The 38SB13, 38SB18, 38SB19, 38SB30, 38SB31, and 38SB39 antibody is able to specifically recognize CD38, and directs the cytotoxic agent to an abnormal cell or a tissue, such as cancer cells, in a targeted fashion.

The second component of the cytotoxic conjugates of the present invention is a cytotoxic agent. The term "cytotoxic agent" as used herein refers to a substance that reduces or blocks the function, or growth, of cells and/or causes destruction of cells.

In preferred embodiments, the cytotoxic agent is a small drug, a prodrug, a taxoid, a maytansinoid such as DM1 or DM4, a tomaymycin derivative, a leptomycin derivative, CC-1065 or a CC-1065 analog. In preferred embodiments, the cell binding agents of the present invention are covalently attached, directly or via a cleavable or non-cleavable linker, to the cytotoxic agent.

The cell binding agents, cytotoxic agents, and linkers are discussed in more detail below.

Cell Binding Agents

The effectiveness of the compounds of the present invention as therapeutic agents depends on the careful selection of an appropriate cell binding agent. Cell binding agents may be of any kind presently known, or that become known, and includes peptides and non-peptides. The cell binding agent may be any compound that can bind a cell, either in a specific or non-specific manner. Generally, these can be antibodies (especially monoclonal antibodies), lymphokines, hormones, growth factors, vitamins, nutrient-transport molecules (such as transferrin), or any other cell binding molecule or substance.

More specific examples of cell binding agents that can be used include:
a) polyclonal antibodies;
b) monoclonal antibodies;
c) fragments of antibodies such as Fab, Fab', and F(ab')2, Fv (Parham, 1983, *J. Immunol.*, 131: 2895-2902; Spring et al., 1974, *J. Immunol.*, 113: 470-478; Nisonoff et al., 1960, *Arch. Biochem. Biophys.*, 89: 230-244);

In particular, an anti-CD38 monoclonal antibody selected from 38SB13, 38SB18, 38SB19, 38SB30, 38SB31, and 38SB39 can be used as a cell binding agent according to the present invention. Likewise, said cell binding agent can be a chimeric version of one of the 38SB13, 38SB18, 38SB19, 38SB30, 38SB31, and 38SB39 monoclonal antibodies. Preferably, a humanized anti-CD38 antibody is used as the cell binding agent of the present invention. More preferably the humanized anti-CD38 antibody is selected from humanized or resurfaced 38SB13, 38SB18, 38SB19, 38SB30, 38SB31, and 38SB39 antibodies.

Cytotoxic Agents

In another embodiment, the humanized antibody or an epitope-binding fragment thereof can be conjugated to a drug, such as a maytansinoid, to form a prodrug having specific cytotoxicity towards antigen-expressing cells by targeting the drug to the CD38 protein. Cytotoxic conjugates comprising such antibodies and a small, highly toxic drug (e.g., maytansinoids, taxanes, tomaymycin derivatives, leptomycin derivatives, and CC-1065 analogs) can be used as a therapeutic for treatment of tumors, such as lymphoma, leukemia, and multiple myeloma.

The cytotoxic agent used in the cytotoxic conjugate of the present invention may be any compound that results in the death of a cell, or induces cell death, or in some manner decreases cell viability. Preferred cytotoxic agents include, for example, maytansinoids and maytansinoid analogs, taxoids, tomaymycin derivatives, leptomycin derivatives, CC-1065 and CC-1065 analogs, dolastatin and dolastatin analogs, defined below. These cytotoxic agents are conjugated to the antibodies, antibodies fragments, functional equivalents, improved antibodies and their analogs as disclosed herein The cytotoxic conjugates may be prepared by in vitro methods. In order to link a drug or prodrug to the antibody, a linking group is used. Suitable linking groups are well known in the art and include disulfide groups, thioether groups, acid labile groups, photolabile groups, peptidase labile groups and esterase labile groups. Preferred linking groups are disulfide groups and thioether groups. For example, conjugates can be constructed using a disulfide exchange reaction or by forming a thioether bond between the antibody and the drug or prodrug.

Maytansinoids

Among the cytotoxic agents that may be used in the present invention to form a cytotoxic conjugate, are maytansinoids and maytansinoid analogs. Examples of suitable maytansinoids include maytansinol and maytansinol analogs. Maytansinoids are drugs that inhibit microtubule formation and that are highly toxic to mammalian cells.

Examples of suitable maytansinol analogues include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 6,333,410; 5,475,092; 5,585,499; and 5,846,545.

Specific examples of suitable analogues of maytansinol having a modified aromatic ring include:
(1) C-19-dichloro (U.S. Pat. No. 4,256,746) (prepared by LAH reduction of ansamytocin P2);
(2) C-20-hydroxy (or C-20-demethyl)+/−C-19-dichloro (U.S. Pat. Nos. 4,361,650 and 4,307,016) (prepared by demethylation using *Streptomyces* or *Actinomyces* or dechlorination using LAH); and
(3) C-20-demethoxy, C-20-acyloxy (—OCOR), +/−dichloro (U.S. Pat. No. 4,294,757) (prepared by acylation using acyl chlorides).

Specific examples of suitable analogues of maytansinol having modifications of other positions include:
(1) C-9-SH (U.S. Pat. No. 4,424,219) (prepared by the reaction of maytansinol with H2S or P2S5);
(2) C-14-alkoxymethyl (demethoxy/CH2OR) (U.S. Pat. No. 4,331,598);
(3) C-14-hydroxymethyl or acyloxymethyl (CH2OH or CH2OAc) (U.S. Pat. No. 4,450,254) (prepared from *Nocardia*);
(4) C-15-hydroxy/acyloxy (U.S. Pat. No. 4,364,866) (prepared by the conversion of maytansinol by *Streptomyces*);
(5) C-15-methoxy (U.S. Pat. Nos. 4,313,946 and 4,315,929) (isolated from *Trewia Nudiflora*);
(6) C-18-N-demethyl (U.S. Pat. Nos. 4,362,663 and 4,322, 348) (prepared by the demethylation of maytansinol by *Streptomyces*); and
(7) 4,5-deoxy (U.S. Pat. No. 4,371,533) (prepared by the titanium trichloride/LAH reduction of maytansinol).

In a preferred embodiment, the cytotoxic conjugates of the present invention utilize the thiol-containing maytansinoid (DM1), formally termed N2'-deacetyl-N2'-(3-mercapto-1-oxypropyl)-maytansine, as the cytotoxic agent. DM1 is represented by the following structural formula (I):

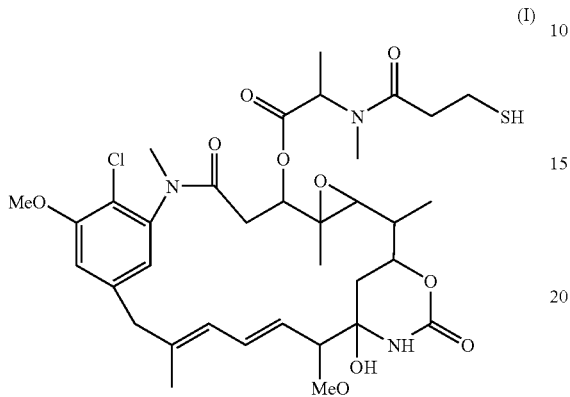

In another preferred embodiment, the cytotoxic conjugates of the present invention utilize the thiol-containing maytansinoid N2'-deacetyl-N-2'(4-methyl-4-mercapto-1-oxopentyl)-maytansine as the cytotoxic agent. DM4 is represented by the following structural formula (II):

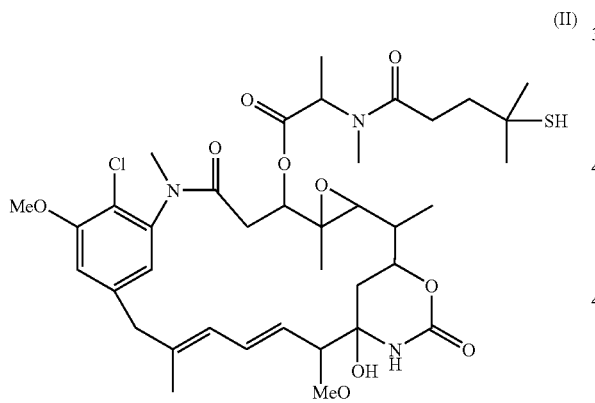

In further embodiments of the invention, other maytansines, including thiol and disulfide-containing maytansinoids bearing a mono or di-alkyl substitution on the carbon atom bearing the sulfur atom, may be used. These include a maytansinoid having, at C-3, C-14 hydroxymethyl, C-15 hydroxy, or C-20 desmethyl, an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Such additional maytansines include compounds represented by formula (III):

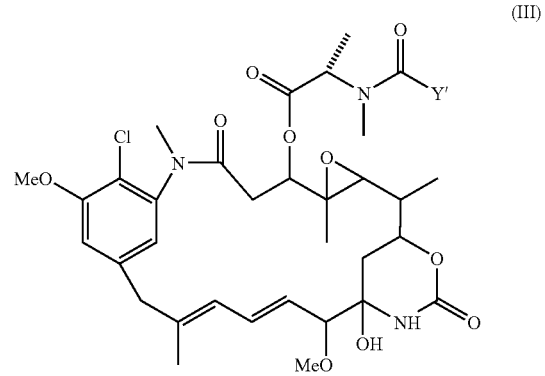

wherein:

Y' represents
$(CR_7R_8)_l(CR_9\!=\!CR_{10})_p(C\!\equiv\!C)_qA_o(CR_5R_6)_mD_u(CR_{11}\!=\!CR_{12})_r(C\!\equiv\!C)_sB_t(CR_3R_4)_nCR_1R_2SZ$, wherein:
$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition $R_2$ can be H;

A, B, D are cycloalkyl or cycloalkenyl having 3-10 carbon atoms, simple or substituted aryl or heterocyclic aromatic or heterocycloalkyl radical;

$R_3$, $R_4$, $R_5$, $R_6$, $R_7$, $R_8$, $R_9$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;

l, m, n, o, p, q, r, s, and t are each independently 0 or an integer of from 1 to 5, provided that at least two of l, m, n, o, p, q, r, s and t are not zero at any one time; and Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (III) include compounds of formula (III) wherein:

$R_1$ is H, $R_2$ is methyl and Z is H.
$R_1$ and $R_2$ are methyl and Z is H.
$R_1$ is H, $R_2$ is methyl, and Z is —$SCH_3$.
$R_1$ and $R_2$ are methyl, and Z is —$SCH_3$.

Such additional maytansines also include compounds represented by formula (IV-L), (IV-D), or (IV-D,L):

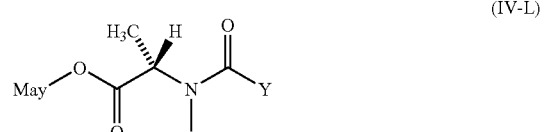

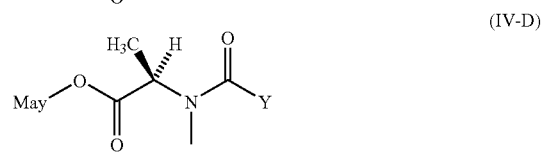

-continued

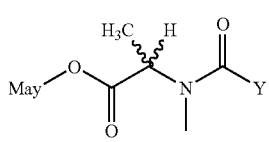
(IV-D,L)

wherein:
Y represents $(CR_7R_8)_l(CR_5R_6)_m(CR_3R_4)_nCR_1R_2SZ$,
wherein:
- $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, and in addition $R_2$ can be H;
- $R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical;
- l, m and n are each independently an integer of from 1 to 5, and in addition n can be 0;
- Z is H, SR or —COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocycloalkyl radical; and
- May represents a maytansinoid which bears the side chain at C-3, C-14 hydroxymethyl, C-15 hydroxy or C-20 desmethyl.

Preferred embodiments of formulas (IV-L), (IV-D) and (IV-D,L) include compounds of formulas (IV-L), (IV-D) and (IV-D,L) wherein:
$R_1$ is H, $R_2$ is methyl, $R_5$, $R_6$, $R_7$, and $R_8$ are each H, l and m are each 1, n is 0, and Z is H.
$R_1$ and $R_2$ are methyl, $R_5$, $R_6$, $R_7$, $R_8$ are each H, l and m are 1, n is 0, and Z is H.
$R_1$ is H, $R_2$ is methyl, $R_5$, $R_6$, $R_7$, $R_8$ are each H, l and m are each 1, n is 0, and Z is —$SCH_3$.
$R_1$ and $R_2$ are methyl, $R_5$, $R_6$, $R_7$, $R_8$ are each H, l and m are 1, n is 0, and Z is —$SCH_3$.

Preferably the cytotoxic agent is represented by formula (IV-L).

Such additional maytansines also include compounds represented by formula (V):

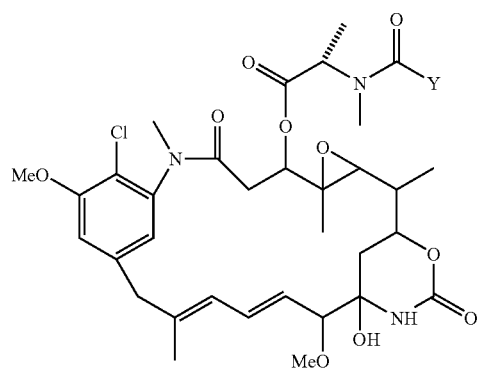
(V)

wherein:
Y represents $(CR_7R_8)_l(CR_5R_6)_m(CR_3R_4)_nCR_1R_2SZ$,
wherein:
- $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition $R_2$ can be H;
- $R_3$, $R_4$, $R_5$, $R_6$, $R_7$, and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical;
- l, m and n are each independently an integer of from 1 to 5, and in addition n can be 0; and
- Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (V) include compounds of formula (V) wherein:
$R_1$ is H, $R_2$ is methyl, $R_5$, $R_6$, $R_7$, and $R_8$ are each H; l and m are each 1; n is 0; and Z is H.
$R_1$ and $R_2$ are methyl, $R_5$, $R_6$, $R_7$, and $R_8$ are each H, l and m are 1; n is 0; and Z is H.
$R_1$ is H, $R_2$ is methyl, $R_5$, $R_6$, $R_7$, and $R_8$ are each H, l and m are each 1, n is 0, and Z is —$SCH_3$.
$R_1$ and $R_2$ are methyl, $R_5$, $R_6$, $R_7$, and $R_8$ are each H, l and m are 1, n is 0, and Z is —$SCH_3$.

Such additional maytansines further include compounds represented by formula (VI-L), (VI-D), or (VI-D,L):

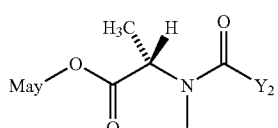
(VI-L)

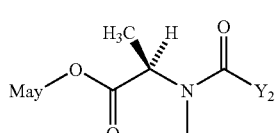
(VI-D)

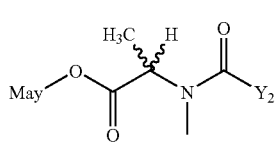
(VI-D, L)

wherein:
$Y_2$ represents $(CR_7R_8)_l(CR_5R_6)_m(CR_3R_4)_nCR_1R_2SZ_2$,
wherein:
- $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition $R_2$ can be H;
- $R_3$, $R_4$, $R_5$, $R_6$, $R_7$ and $R_8$ are each independently H, $CH_3$, $C_2H_5$, linear cyclic alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;
- l, m and n are each independently an integer of from 1 to 5, and in addition n can be 0;

$Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical; and May is a maytansinoid.

Such additional maytansines also include compounds represented by formula (VII):

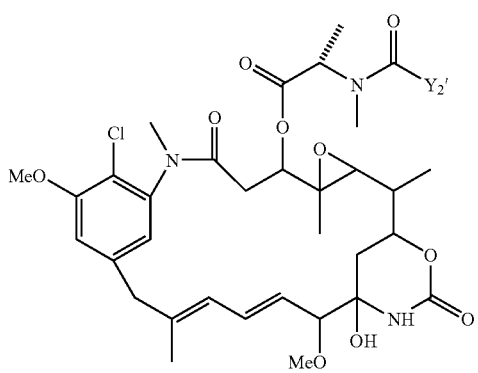

(VII)

wherein:

$Y_2'$ represents
$(CR_7R_8)_l(CR_9\!=\!CR_{10})_p(C\!\equiv\!C)_qA_r(CR_5R_6)_mD_u(CR_{11}\!=\!CR_{12})_r(C\!\equiv\!C)_sB_t(CR_3R_4)_nCR_1R_2SZ_2$, wherein:

$R_1$ and $R_2$ are each independently $CH_3$, $C_2H_5$, linear branched or alkyl or alkenyl having from 1 to 10 carbon atoms, cyclic alkyl or alkenyl having from 3 to 10 carbon atoms, phenyl, substituted phenyl or heterocyclic aromatic or heterocycloalkyl radical, and in addition $R_2$ can be H;

A, B, and D each independently is cycloalkyl or cycloalkenyl having 3 to 10 carbon atoms, simple or substituted aryl, or heterocyclic aromatic or heterocycloalkyl radical;

$R_3$, $R_4$, $R_5$, $R_6$, $R_7$, $R_8$, $R_9$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;

l, m, n, o, p, q, r, s, and t are each independently 0 or an integer of from 1 to 5, provided that at least two of l, m, n, o, p, q, r, s and t are not zero at any one time; and $Z_2$ is SR or —COR, wherein R is linear alkyl or alkenyl having from 1 to 10 carbon atoms, branched or cyclic alkyl or alkenyl having from 3-10 carbon atoms, or simple or substituted aryl or heterocyclic aromatic or heterocycloalkyl radical.

Preferred embodiments of formula (VII) include compounds of formula (VII) wherein: $R_1$ is H and $R_2$ is methyl.

The above-mentioned maytansinoids can be conjugated to anti-CD38 antibody 38SB13, 38SB18, 38SB19, 38SB30, 38SB31, or 38SB39 or a homologue or fragment thereof, wherein the antibody is linked to the maytansinoid using the thiol or disulfide functionality that is present on the acyl group of an acylated amino acid side chain found at C-3, C-14 hydroxymethyl, C-15 hydroxy or C-20 desmethyl of the maytansinoid, and wherein the acyl group of the acylated amino acid side chain has its thiol or disulfide functionality located at a carbon atom that has one or two substituents, said substituents being $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and in addition one of the substituents can be H, and wherein the acyl group has a linear chain length of at least three carbon atoms between the carbonyl functionality and the sulfur atom.

A preferred conjugate of the present invention is the one that comprises the anti-anti-CD38 antibody 38SB13, 38SB18, 38SB19, 38SB30, 38SB31, or 38SB39 or a homologue or fragment thereof, conjugated to a maytansinoid of formula (VIII):

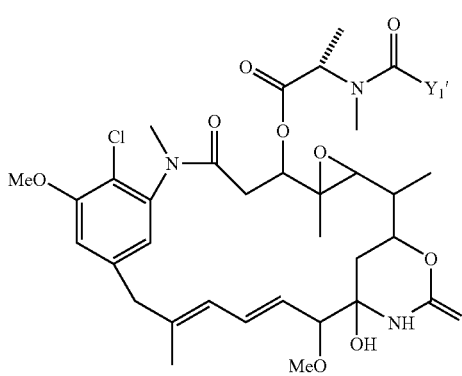

(VIII)

wherein:

$Y_1'$ represents
$(CR_7R_8)_l(CR_9\!=\!CR_{10})_p(C\!\equiv\!C)_qA_r(CR_5R_6)_mD_u(CR_{11}\!=\!CR_{12})_r(C\!\equiv\!C)_sB_t(CR_3R_4)_nCR_1R_2S\!-\!$, wherein:

A, B, and D, each independently is cycloalkyl or cycloalkenyl having 3-10 carbon atoms, simple or substituted aryl, or heterocyclic aromatic or heterocycloalkyl radical;

$R_3$, $R_4$, $R_5$, $R_6$, $R_7$, $R_8$, $R_9$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical; and l, m, n, o, p, q, r, s, and t are each independently 0 or an integer of from 1 to 5, provided that at least two of l, m, n, o, p, q, r, s and t are non-not zero at any one time.

Preferably, $R_1$ is H and $R_2$ is methyl or $R_1$ and $R_2$ are methyl.

An even more preferred conjugate of the present invention is the one that comprises the anti-CD38 antibody 38SB13, 38SB18, 38SB19, 38SB30, 38SB31, or 38SB39 or a homologue or fragment thereof, conjugated to a maytansinoid of formula (IX-L), (IX-D), or (IX-D,L):

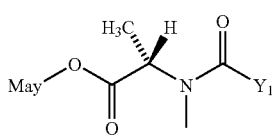

IX-L

-continued (IX-D)

[Chemical structure: May-O-C(=O)-CH(CH₃)(H)-N(CH₃)-C(=O)-Y₁]

(IX-D,L)

[Chemical structure: May-O-C(=O)-CH(CH₃)(H, wavy bond)-N(CH₃)-C(=O)-Y₁]

wherein:

$Y_1$ represents $(CR_7R_8)_l(CR_5R_6)_m(CR_3R_4)_nCR_1R_2S-$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, heterocyclic aromatic or heterocycloalkyl radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical;

l, m and n are each independently an integer of from 1 to 5, and in addition n can be 0; and May represents a maytansinol which bears the side chain at C-3, C-14 hydroxymethyl, C-15 hydroxy or C-20 desmethyl.

Preferred embodiments of formulas (IX-L), (IX-D) and (IX-D,L) include compounds of formulas (IX-L), (IX-D) and (IX-D,L) wherein:

$R_1$ is H and $R_2$ is methyl or $R_1$ and $R_2$ are methyl, $R_1$ is H, $R_2$ is methyl, $R_5$, $R_6$, $R_7$ and $R_8$ are each H; l and m are each 1; n is 0, $R_1$ and $R_2$ are methyl; $R_5$, $R_6$, $R_7$ and $R_8$ are each H; l and m are 1; n is 0.

Preferably the cytotoxic agent is represented by formula (IX-L).

An further preferred conjugate of the present invention is the one that comprises the anti-CD38 antibody 38SB13, 38SB18, 38SB19, 38SB30, 38SB31, or 38SB39 or a homologue or fragment thereof, conjugated to a maytansinoid of formula (X):

(X)

[Chemical structure of maytansinoid showing macrocyclic ring with MeO, Cl, N-Me, OMe, OH, NH, and ester linkage to Y₁]

wherein the substituents are as defined for formula (IX) above.

Especially preferred are any of the above-described compounds, wherein $R_1$ is H, $R_2$ is methyl, $R_5$, $R_6$, $R_7$ and $R_8$ are each H, l and m are each 1, and n is 0.

Further especially preferred are any of the above-described compounds, wherein $R_1$ and $R_2$ are methyl, $R_5$, $R_6$, $R_7$, $R_8$ are each H, l and m are 1, and n is 0

Further, the L-aminoacyl stereoisomer is preferred.

Each of the maytansinoids taught in pending U.S. patent application Ser. No. 10/849,136, filed May 20, 2004, may also be used in the cytotoxic conjugate of the present invention. The entire disclosure of U.S. patent application Ser. No. 10/849,136 is incorporated herein by reference.

Disulfide-Containing Linking Groups

In order to link the maytansinoid to a cell binding agent, such as the 38SB13, 38SB18, 38SB19, 38SB30, 38SB31, or 38SB39 antibody, the maytansinoid comprises a linking moiety. The linking moiety contains a chemical bond that allows for the release of fully active maytansinoids at a particular site. Suitable chemical bonds are well known in the art and include disulfide bonds, acid labile bonds, photolabile bonds, peptidase labile bonds and esterase labile bonds. Preferred are disulfide bonds.

The linking moiety also comprises a reactive chemical group. In a preferred embodiment, the reactive chemical group can be covalently bound to the maytansinoid via a disulfide bond linking moiety.

Particularly preferred reactive chemical groups are N-succinimidyl esters and N-sulfosuccinimidyl esters.

Particularly preferred maytansinoids comprising a linking moiety that contains a reactive chemical group are C-3 esters of maytansinol and its analogs where the linking moiety contains a disulfide bond and the chemical reactive group comprises a N-succinimidyl or N-sulfosuccinimidyl ester.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

While the synthesis of esters of maytansinol having a linking moiety is described in terms of disulfide bond-containing linking moieties, one of skill in the art will understand that linking moieties with other chemical bonds (as described above) can also be used with the present invention, as can other maytansinoids. Specific examples of other chemical bonds include acid labile bonds, photolabile bonds, peptidase labile bonds and esterase labile bonds. The disclosure of U.S. Pat. No. 5,208,020, incorporated herein, teaches the production of maytansinoids bearing such bonds.

The synthesis of maytansinoids and maytansinoid derivatives having a disulfide moiety that bears a reactive group is described in U.S. Pat. Nos. 6,441,163 and 6,333,410, and U.S. application Ser. No. 10/161,651, each of which is herein incorporated by reference.

The reactive group-containing maytansinoids, such as DM1, are reacted with an antibody, such as the 38SB13, 38SB18, 38SB19, 38SB30, 38SB31, or 38SB39 antibody, to produce cytotoxic conjugates. These conjugates may be purified by HPLC or by gel-filtration.

Several excellent schemes for producing such antibody-maytansinoid conjugates are provided in U.S. Pat. No. 6,333,410, and U.S. application Ser. Nos. 09/867,598, 10/161,651 and 10/024,290, each of which is incorporated herein in its entirety.

In general, a solution of an antibody in aqueous buffer may be incubated with a molar excess of maytansinoids having a disulfide moiety that bears a reactive group. The reaction mixture can be quenched by addition of excess amine (such as ethanolamine, taurine, etc.). The maytansinoid-antibody conjugate may then be purified by gel-filtration.

The number of maytansinoid molecules bound per antibody molecule can be determined by measuring spectrophotometrically the ratio of the absorbance at 252 nm and 280 nm. An average of 1-10 maytansinoid molecules/antibody molecule is preferred.

Conjugates of antibodies with maytansinoid drugs can be evaluated for their ability to suppress proliferation of various unwanted cell lines in vitro. For example, cell lines such as the human lymphoma cell line Daudi, the human lymphoma cell line Ramos, the human multiple myeloma cell line MOLP-8, and the human T acute lymphocytic leukemia line MOLT-4 can easily be used for the assessment of cytotoxicity of these compounds. Cells to be evaluated can be exposed to the compounds for 24 hours and the surviving fractions of cells measured in direct assays by known methods. IC50 values can then be calculated from the results of the assays.

Peg-Containing Linking Groups

Maytansinoids may also be linked to cell binding agents using PEG linking groups, as set forth in U.S. application Ser. No. 10/024,290. These PEG linking groups are soluble both in water and in non-aqueous solvents, and can be used to join one or more cytotoxic agents to a cell binding agent. Exemplary PEG linking groups include hetero-bifunctional PEG linkers that bind to cytotoxic agents and cell binding agents at opposite ends of the linkers through a functional sulfhydryl or disulfide group at one end, and an active ester at the other end.

As a general example of the synthesis of a cytotoxic conjugate using a PEG linking group, reference is again made to U.S. application Ser. No. 10/024,290 for specific details. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group.

Taxanes

The cytotoxic agent used in the cytotoxic conjugates according to the present invention may also be a taxane or derivative thereof.

Taxanes are a family of compounds that includes paclitaxel (Taxol®), a cytotoxic natural product, and docetaxel (Taxotere), a semi-synthetic derivative, two compounds that are widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell binding agents.

A preferred taxane for use in the preparation of cytotoxic conjugates is the taxane of formula (XI):

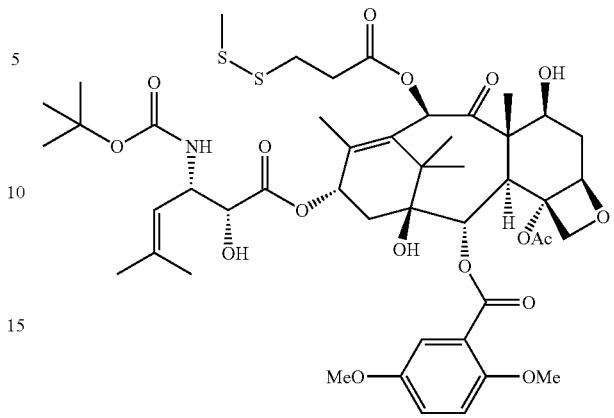

Methods for synthesizing taxanes that may be used in the cytotoxic conjugates of the present invention, along with methods for conjugating the taxanes to cell binding agents such as antibodies, are described in detail in U.S. Pat. Nos. 5,416,064, 5,475,092, 6,340,701, 6,372,738 and 6,436,931, and in U.S. application Ser. Nos. 10/024,290, 10/144,042, 10/207,814, 10/210,112 and 10/369,563.

Tomaymycin Derivatives

The cytotoxic according to the present invention may also a tomaymycin derivative. Tomaymycin derivatives are pyrrolo[1,4]benzodiazepines (PBDs), a known class of compounds exerting their biological properties by covalently binding to the N2 of guanine in the minor groove of DNA. PBDs include a number of minor groove binders such as anthramycin, neothramycin and DC-81.

Novel tomaymycin derivatives that retain high cytotoxicity and that can be effectively linked to cell binding agents are described in the International Application No. PCT/IB2007/000142, whose content is herein incorporated by reference. The cell binding agent-tomaymycin derivative complexes permit the full measure of the cytotoxic action of the tomaymycin derivatives to be applied in a targeted fashion against unwanted cells only, therefore avoiding side effects due to damage to non-targeted healthy cells.

The cytotoxic agent according to the present invention comprises one or more tomaymycin derivatives, linked to a cell binding agent, such as the 38SB13, 38SB18, 38SB19, 38SB30, 38SB31, or 38SB39 antibody, via a linking group. The linking group is part of a chemical moiety that is covalently bound to a tomaymycin derivative through conventional methods. In a preferred embodiment, the chemical moiety can be covalently bound to the tomaymycin derivative via a disulfide bond.

The tomaymycin derivatives useful in the present invention have the formula (XII) shown below:

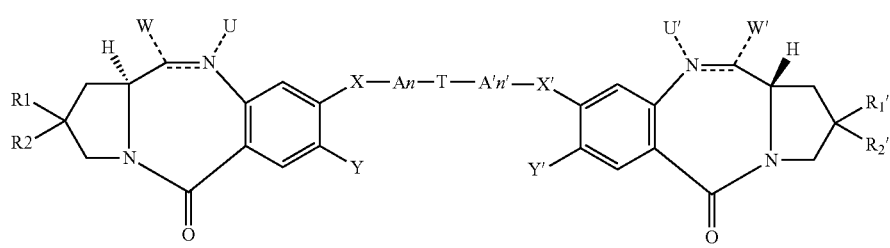

wherein
- - - represents an optional single bond;

≈ represents either a single bond or a double bond;

provided that when ≈ represents a single bond, U and U', the same or different, independently represent H, and W and W', the same or different, are independently selected from the group consisting of OH, an ether such as —OR, an ester (e.g. an acetate), such as —OCOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —SO3-, a sulfonamide such as —NR-SOOR, an amine such as —NRR', optionally cyclic amine such that N10 and C11 are a part of the cycle, a hydroxylamine derivative such as —NROR, an amide such as —NRCOR, an azido such as —N3, a cyano, a halo, a trialkyl or triarylphosphonium, an aminoacid-derived group; Preferably W and W' are the same or different and are OH, Ome, Oet, NHCONH$_2$, SMe;

and when ≈ represents a double bond, U and U' are absent and W and W' represent H;

R1, R2, R1', R2' are the same or different and independently chosen from Halide or Alkyl optionally substituted by one or more Hal, CN, NRR', CF$_3$, OR, Aryl, Het, S(O)$_q$R, or R1 and R2 and R1' and R2' form together a double bond containing group =B and =B' respectively.

Preferably, R1 and R2 and R1' and R2' form together a double bond containing group =B and =B' respectively.

B and B' are the same or different and independently chosen from Alkenyl being optionally substituted by one or more Hal, CN, NRR', CF$_3$, OR, Aryl, Het, S(O)$_q$R or B and B' represent an oxygen atom.

Preferably, B=B'.
More preferably, B=B'=CH$_2$ or =CH—CH$_3$,

X, X' are the same or different and independently chosen from one or more —O—, —NR—, —(C=O)—, —S(O)$_q$—.

Preferably, X=X'.
More preferably, X=X'=O.

A, A' are the same or different and independently chosen from Alkyl or Alkenyl optionally containing an oxygen, a nitrogen or a sulfur atom, each being optionally substituted by one or more Hal, CN, NRR', CF$_3$, OR, S(O)$_q$R, Aryl, Het, Alkyl, Alkenyl.

Preferably, A=A'.
More preferably, A=A'=linear unsubstituted alkyl.

Y, Y' are the same or different and independently chosen from H, OR;

Preferably, Y=Y'.
More preferably, Y=Y'=OAlkyl, more preferably OMethyl.

T is —NR—, —O—, —S(O)$_q$, or a 4 to 10-membered aryl, cycloalkyl, heterocyclic or heteroaryl, each being optionally substituted by one or more Hal, CN, NRR', CF$_3$, R, OR, S(O)$_q$R, and/or linker(s), or a branched Alkyl, optionally substituted by one or more Hal, CN, NRR', CF$_3$, OR, S(O)$_q$R and/or linker(s), or a linear Alkyl substituted by one or more Hal, CN, NRR', CF$_3$, OR, S(O)$_q$R and/or linker(s).

Preferably, T is a 4 to 10-membered aryl or heteroaryl, more preferably phenyl or pyridyl, optionally substituted by one or more linker(s).

Said linker comprises a linking group. Suitable linking groups are well known in the art and include thiol, sulfide, disulfide groups, thioether groups, acid labile groups, photolabile groups, peptidase labile groups and esterase labile groups. Preferred are disulfide groups and thioether groups.

When the linking group is a thiol-, sulfide (or so-called thioether —S—) or disulfide (—S—S—)-containing group, the side chain carrying the thiol, the sulfide or disulfide group can be linear or branched, aromatic or heterocyclic. One of ordinary skill in the art can readily identify suitable side chains.

Preferably, said linker is of formula:

-G-D-(Z)$p$-S—Z' where
G is a single or double bond, —O—, —S— or —NR—;
D is a single bond or -E-, -E-NR—, -E-NR—F—, -E-O—, -E-O—F—, -E-NR—CO—, -E-NR—CO—F—, -E-CO—, —CO-E-, -E-CO—F, -E-S—, -E-S—F—, -E-NR—C—S—, -E-NR—CS—F—;
where E and F are the same or different and are independently chosen from linear or branched —(OCH2CH2)iAlkyl (OCH2CH2)j-, -Alkyl(OCH2CH2)i-Alkyl-, —(OCH2CH2)i-, —(OCH2CH2)iCycloalkyl (OCH2CH2)j-, —(OCH2CH2)iHeterocyclic(OCH2CH2)j-, —(OCH2CH2)iAryl(OCH2CH2)j-, —(OCH2CH2)iHeteroaryli(OCH2CH2)j-, -Alkyl-(OCH2CH2)iAlkyl (OCH2CH2)j-, -Alkyl-(OCH2CH2)i-, -Alkyl-(OCH2CH2)iCycloalkyl(OCH2CH2)j-, -Alkyl (OCH2CH2)iHeterocyclic(OCH2CH2)j-, -Alkyl-(OCH2CH2)iAryl(OCH2CH2)j-, -Alkyl(OCH2CH2) iHeteroaryl(OCH2CH2)j-, -Cycloalkyl-Alkyl-, -Alkyl-Cycloalkyl-, -Heterocyclic-Alkyl-, -Alkyl-Heterocyclic-, -Alkyl-Aryl-, -Aryl-Alkyl-, -Alkyl-Heteroaryl-, -Heteroaryl-Alkyl-;
where i and j, identical or different are integers and independently chosen from 0, 1 to 2000;
Z is linear or branched -Alkyl-;
p is 0 or 1;
Z' represents H, a thiol protecting group such as COR, R20 or SR20, wherein R20 represents H, methyl, Alkyl, optionally substituted Cycloalkyl, aryl, heteroaryl or heterocyclic, provided that when Z' is H, said compound is in equilibrium with the corresponding compound formed by intramolecular cyclisation resulting from addition of the thiol group —SH on the imine bond —NH= of one of the PBD moieties.
n, n', equal or different are 0 or 1.
q is 0, 1 or 2.
R, R' are equal or different and independently chosen from H, Alkyl, Aryl, each being optionally substituted by Hal, CN, NRR', CF3, R, OR, S(O)qR, Aryl, Het;
or their pharmaceutically acceptable salts, hydrates, or hydrated salts, or the polymorphic crystalline structures of these compounds or their optical isomers, racemates, diastereomers or enantiomers.

The compounds of the general formula (XII) having geometrical and stereoisomers are also a part of the invention.

The N-10, C-11 double bond of tomaymycin derivatives of formula (XII) is known to be readily convertible in a reversible manner to corresponding imine adducts in the presence of water, an alcohol, a thiol, a primary or secondary amine, urea and other nucleophiles. This process is reversible and can easily regenerate the corresponding tomaymycin derivatives in the presence of a dehydrating agent, in a non-protic organic solvent, in vacuum or at high temperatures (Z. Tozuka, 1983, *J. Antibiotics*, 36: 276).

Thus, reversible derivatives of tomaymycin derivatives of general formula (XIII) can also be used in the present invention:

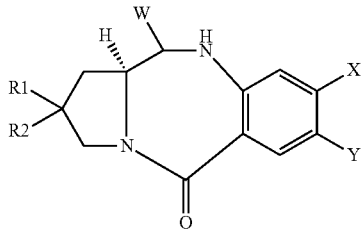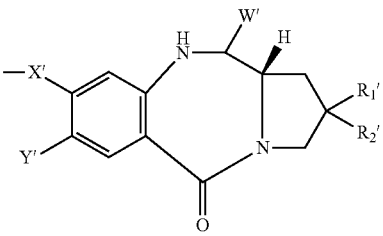

(XIII)

where A, X, Y, n, T, A', X', Y', n', R1, R2, R1', R2' are defined as in formula (XII) and W, W' are the same or different and are selected from the group consisting of OH, an ether such as —OR, an ester (e.g. an acetate), such as —OCOR, —COOR, a carbonate such as —OCOOR, a carbamate such as —OCONRR', a cyclic carbamate, such that N10 and C11 are a part of the cycle, a urea such as —NRCONRR', a thiocarbamate such as —OCSNHR, a cyclic thiocarbamate such that N10 and C11 are a part of the cycle, —SH, a sulfide such as —SR, a sulphoxide such as —SOR, a sulfone such as —SOOR, a sulphonate such as —SO3-, a sulfonamide such as —NRSOOR, an amine such as —NRR', optionally cyclic amine such that N10 and C11 are a part of the cycle, a hydroxylamine derivative such as —NROR', an amide such as —NRCOR, —NRCONRR', an azido such as —N3, a cyano, a halo, a trialkyl or triarylphosphonium, an aminoacid-derived group. Preferably, W and W' are the same or different and are OH, Ome, Oet, NHCONH2, SMe.

Compounds of formula (XIII) may thus be considered as solvates, including water when the solvent is water; these solvates can be particularly useful.

In a preferred embodiment, the tomaymycin derivatives of the invention are selected from the group consisting in:

8,8'-[1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-methoxy-1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-[1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[1,4-butanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[3-methyl-1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[2,6-pyridinediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[4-(3-tert-butoxycarbonylaminopropyloxy)-2,6-pyridinediylbis-(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-(3-aminopropyloxy)-1,3-benzenediylbis(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-(N-methyl-3-tert-butoxycarbonylaminopropyl)-1,3-benzenediylbis-(methylenoxy)]-bis[(S)-2-eth-(E)-ylidene-7-methoxy-1,2,3,11a-tetrahydro-5H-pyrrolo[2,1-c][1,4]benzodiazepin-5-one]

8,8'-{5-[3-(4-methyl-4-methyldisulfanyl-pentanoylamino)propyloxy]-1,3-benzenediylbis(methylenoxy)}-bis[(S)-2-eth-(E)-ylidene-7-methoxy-1,2,3,11a-tetrahydro-5H-pyrrolo[2,1-c][1,4]benzodiazepin-5-one]

8,8'-[5-acetylthiomethyl-1,3-benzenediylbis(methylenoxy)]-bis[(S)-2-methylene-7-methoxy-1,2,3,11a-tetrahydro-5H-pyrrolo[2,1-c][1,4]benzodiazepin-5-one]

bis-{2-[(S)-2-methylene-7-methoxy-5-oxo-1,3,11a-tetrahydro-5H-pyrrolo[2,1-c][1,4]benzodiazepin-8-yloxy]-ethyl}-carbamic acid tert-butyl ester 8,8'-[3-(2-acetylthioethyl)-1,5-pentanediylbis(oxy)]-bis[(S)-2-methylene-7-methoxy-1,2,3,11a-tetrahydro-5H-pyrrolo[2,1-c][1,4]benzodiazepin-5-one]

8,8'-[5-(N-4-mercapto-4,4-dimethylbutanoyl)amino-1,3-benzenediylbis(methylenoxy)]-bis[7-methoxy-2-methylene-1,2,3,11a-tetrahydro-5H-pyrrolo[2,1-c][1,4]benzodiazepin-5-one]

8,8'-[5-(N-4-methyldithio-4,4-dimethylbutanoyl)-amino-1,3-benzenediylbis(methylenoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-mercapto-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-methyldithio-2,2-dimethylethyl)amino-1,3-benzenediyl(methylenoxy)]-bis[7-methoxy-2-methylene-1,2,3,11a-tetrahydro-5H-pyrrolo[2,1-c][1,4]benzodiazepin-5-one]

8,8'-[4-(2-(4-mercapto-4-methyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-(4-methyl-4-methyldisulfanyl)-pentanamido-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-(4-methyl-4-methydisulfanyl)-pentanamido-propoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(4-(4-methyl-4-methyldisulfanyl)-pentanamido-butoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[4-(4-methyl-4-methyldisulfanyl-pentanoyl)-piperazin-1-yl]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(3-[4-(4-methyl-4-methyldisulfanyl-pentanoyl)-piperazin-1-yl]-propyl)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(4-methyl-4-methyldisulfanyl -pentanoylamino)-ethoxy]-ethoxy}-ethoxy)-pyridin-2,6-dimethyl)- dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{(2-[2-(2-{2-[2-(4-methyl-4-methyldisulfanyl-pentanoylamino)-ethoxy]-ethoxy}-ethoxy)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{2-[2-(4-methyl-4-methyldisulfanyl-pentanoylamino)-ethoxy]-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(2-{2-[2-(4-methyl-4-methyldisulfanyl-pentanoylamino)-ethoxy]-ethoxy}-ethoxy)-ethoxy]-ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-[methyl-(2-methyl-2-methyldisulfanyl-propyl)-amino]-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(4-methyl-4-methyldisulfanyl-pentanoyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(2-methyl-2-methyldisulfanyl-propyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(4-methyl-4-methyldisulfanyl)-pentanamido)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

as well as the corresponding mercapto derivatives, or their pharmaceutically acceptable salts, hydrates, or hydrated salts, or the polymorphic crystalline structures of these compounds or their optical isomers, racemates, diastereomers or enantiomers.

Preferred compounds are those of formula:

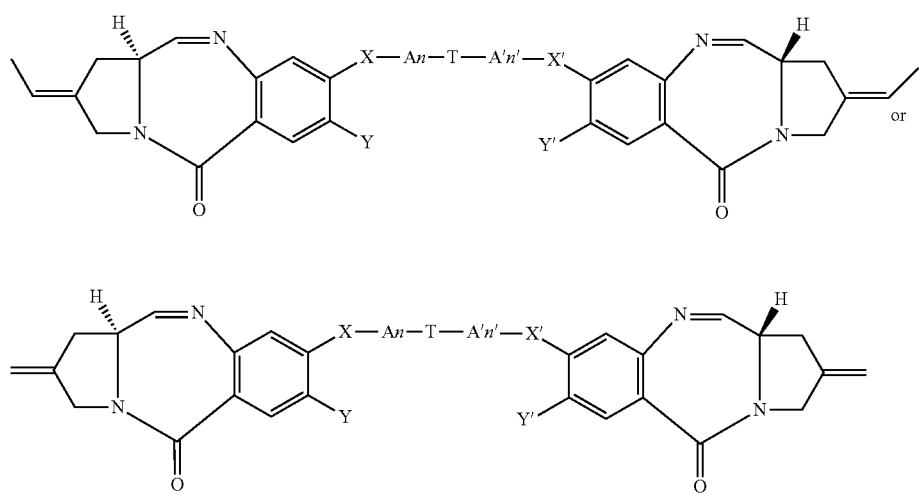

where X, X', A, A', Y, Y', T, n, n' are defined as above.

The compounds of formula (XII) may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art. In particular, such methods can be found in R. C. Larock, *Comprehensive Organic Transformations*, Wiley-VCH Publishers, 1999.

Methods for synthesizing the tomaymycin derivatives which may be used in the invention are described in the International Application No. PCT11B2007/000142. Compounds of the present invention may be prepared by a variety of synthetic routes. The reagents and starting materials are commercially available, or readily synthesized by well-known techniques by one of ordinary skill in the arts (see, for example, WO 00/12508, WO 00/12507, WO 2005/040170, WO 2005/085260, FR1516743, M. Mori et al., 1986, *Tetrahedron*, 42: 3793-3806).

The conjugate molecules of the invention may be formed using any techniques. The tomaymycin derivatives of the invention may be linked to an antibody or other cell binding agent via an acid labile linker, or by a photolabile linker. The derivatives can be condensed with a peptide having a suitable sequence and subsequently linked to a cell binding agent to produce a peptidase labile linker. The conjugates can be prepared to contain a primary hydroxyl group, which can be succinylated and linked to a cell binding agent to produce a conjugate that can be cleaved by intracellular esterases to liberate free derivative. Preferably, the derivatives are synthesized to contain a free or protected thiol group, and then one or more disulfide or thiol-containing derivatives are each covalently linked to the cell binding agent via a disulfide bond or a thioether link.

Numerous methods of conjugation are taught in U.S. Pat. Nos. 5,416,064 and 5,475,092. The tomaymycin derivatives can be modified to yield a free amino group and then linked to an antibody or other cell binding agent via an acid labile linker or a photolabile linker. The tomaymycin derivatives with a free amino or carboxyl group can be condensed with a peptide and subsequently linked to a cell binding agent to produce a peptidase labile linker. The tomaymycin derivatives with a free hydroxyl group on the linker can be succinylated and linked to a cell binding agent to produce a conjugate that can be cleaved by intracellular esterases to liberate free drug. Most preferably, the tomaymycin derivatives are treated to create a free or protected thiol group, and then the disulfide- or thiol containing tomaymycin dimers are linked to the cell binding agent via disulfide bonds.

Preferably, monoclonal antibody- or cell binding agent-tomaymycin derivative conjugates are those that are joined via a disulfide bond, as discussed above, that are capable of delivering tomaymycin derivatives. Such cell binding conjugates are prepared by known methods such as by modifying monoclonal antibodies with succinimidyl pyridyl-dithiopropionate (SPDP) (Carlsson et al., 1978, Biochem. J., 173: 723-737). The resulting thiopyridyl group is then displaced by treatment with thiol-containing tomaymycin derivatives to produce disulfide linked conjugates. Alternatively, in the case of the aryldithio-tomaymycin derivatives, the formation of the cell binding conjugate is effected by direct displacement of the aryl-thiol of the tomaymycin derivative by sulfhydryl groups previously introduced into antibody molecules. Conjugates containing 1 to 10 tomaymycin derivative drugs linked via a disulfide bridge are readily prepared by either method.

More specifically, a solution of the dithio-nitropyridyl modified antibody at a concentration of 2.5 mg/ml in 0.05 M potassium phosphate buffer, at pH 7.5 containing 2 mM EDTA is treated with the thiol-containing tomaymycin derivative (1.3 molar eq./dithiopyridyl group). The release of thio-nitropyridine from the modified antibody is monitored spectrophotometrically at 325 nm and is complete in about 16 hours. The antibody-tomaymycin derivative conjugate is purified and freed of unreacted drug and other low molecular weight material by gel filtration through a column of Sephadex G-25 or Sephacryl S300. The number of tomaymycin derivative moieties bound per antibody molecule can be determined by measuring the ratio of the absorbance at 230 nm and 275 nm. An average of 1-10 tomaymycin derivative molecules/antibody molecule can be linked via disulfide bonds by this method.

The effect of conjugation on binding affinity towards the antigen-expressing cells can be determined using the methods previously described by Liu et al., 1996, Proc. Natl. Acad. Sci. U.S.A., 93: 8618-8623. Cytotoxicity of the tomaymycin derivatives and their antibody conjugates to cell lines can be measured by back-extrapolation of cell proliferation curves as described in Goldmacher et al., 1985, J. Immunol., 135: 3648-3651. Cytotoxicity of these compounds to adherent cell lines can be determined by clonogenic assays as described in Goldmacher et al., 1986, J. Cell Biol., 102: 1312-1319.

Leptomycin Derivatives

The cytotoxic according to the present invention may also a leptomycin derivative.

According to the present invention, "leptomycin derivatives" refer to members of the leptomycin family as defined in Kalesse et al., (2002, Synthesis 8: 981-1003), and includes: leptomycins, such as leptomycin A and leptomycin B, callystatins, ratjadones such as ratjadone A and ratjadone B, anguinomycins such as anguinomycin A, B, C, D, kasusamycins, leptolstatin, leptofuranins, such as leptofuranin A, B, C, D. Derivatives of leptomycin A and B are preferred.

More specifically, the derivatives of the invention are of formula (I):

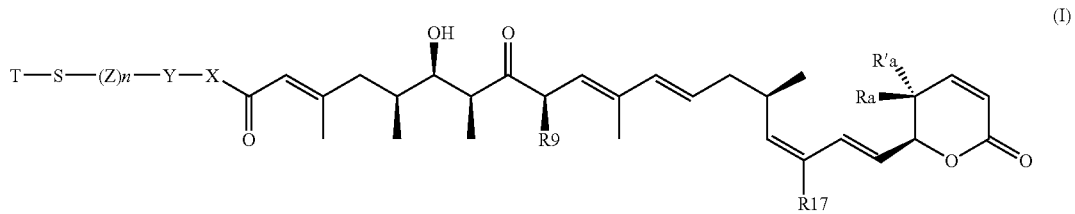

wherein

Ra and Ra' are H or -Alk; preferably Ra is -Alk, preferably methyl and Ra' is H;

R17 is alkyl optionally substituted by OR, CN, NRR', perfluoroalkyl; preferably, R17 is alkyl, more preferably methyl or ethyl;

R9 is alkyl optionally substituted by OR, CN, NRR', perfluoroalkyl; preferably, R9 is alkyl, more preferably methyl;

X is —O— or —NR—; preferably, X is —NR—;

Y is -U-, —NR-U-, —O-U-, —NR—CO-U-, -U-NR—CO—, -U-CO—, —CO-U-;

preferably, when X is —O—, Y is -U-, —NR-U-, -U-NR—CO—;

where U is chosen from linear or branched -Alk-, -Alk (OCH$_2$CH$_2$)$_m$—, —(OCH$_2$CH$_2$)$_m$-Alk-, -Alk (OCH$_2$CH$_2$)$_m$ -Alk-, —(OCH$_2$CH$_2$)$_m$—, -Cycloalkyl-, -Heterocyclic-, -Cycloalkyl-Alk-, -Alk-Cycloalkyl-, -Heterocyclic-Alk-, -Alk-Heterocyclic-;

where m is an integer chosen from 1 to 2000;

preferably, U is linear or branched -Alk-,

Z is -Alk-;

n is 0 or 1; preferably n is 0;

T represents H, a thiol protecting group such as Ac, R$_1$ or SR$_1$, wherein R$_1$ represents H, methyl, Alk, Cycloalkyl, optionally substituted aryl or heterocyclic, or T represents

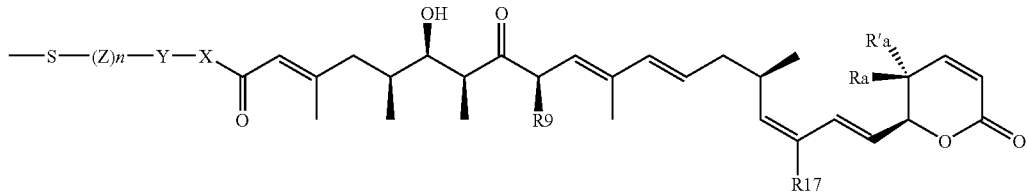

where:

Ra, Ra', R17, R9, X, Y, Z, n are defined as above;

preferably, T is H or SR$_1$, wherein R$_1$ represents Alk, more preferably methyl;

R, R' identical or different are H or alkyl;

Alk represents a linear or branched alkyl; preferably Alk represents —(CH$_{2-q}$(CH$_3$)$_q$)$_p$— where p represents an integer from 1 to 10; and q represents an integer from 0 to 2; preferably, Alk represents —(CH$_2$)— or —C(CH$_3$)$_2$—,
or their pharmaceutically acceptable salts, hydrates, or hydrated salts, or the polymorphic crystalline structures of these compounds or their optical isomers, racemates, diastereomers or enantiomers.

Preferred compounds may be chosen from:

(2-Methylsulfanyl-ethyl)-amid of (2E,10 E,12E,16Z,18E)-(R)-6-Hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid Bis-[(2-mercaptoethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid]

(2-Mercapto-ethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid (2-Methyldisulfanyl-ethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid (2-Methyl-2-methyldisulfanyl-propyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid (2-Mercapto-2-methyl-propyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid or their pharmaceutically acceptable salts, hydrates, or hydrated salts, or the polymorphic crystalline structures of these compounds or their optical isomers, racemates, diastereomers or enantiomers.

In order to link the derivative to a cell-binding agent, the derivative must include a moiety (linking group) that allows the derivatives to be linked to a cell binding agent via a linkage such as a disulfide bond, a sulfide (or called herein thioether) bond, an acid-labile group, a photo-labile group, a peptidase-labile group, or an esterase-labile group. The derivatives are prepared so that they contain a moiety necessary to link the leptomycin derivative to a cell binding agent via, for example, a disulfide bond, a thioether bond, an acid-labile group, a photo-labile group, a peptidase-labile group, or an esterase-labile group. In order to further enhance solubility in aqueous solutions, the linking group can contain a polyethylene glycol spacer. Preferably, a sulfide or disulfide linkage is used because the reducing environment of the targeted cell results in cleavage of the sulfide or disulfide and release of the derivatives with an associated increase in cytotoxicity.

Compounds of the present invention may be prepared by a variety of synthetic routes. The reagents and starting materials are commercially available, or readily synthesized by well-known techniques by one of ordinary skill in the art. Methods for synthesizing leptomycin derivatives that may be used in the cytotoxic conjugates of the present invention, along with methods for conjugating said leptomycin derivatives to cell binding agents such as antibodies, are described in detail in in European Patent Application No. 06290948.6, whose content is incorporated herein by reference.

CC-1065 Analogues

The cytotoxic agent used in the cytotoxic conjugates according to the present invention may also be CC-1065 or a derivative thereof.

CC-1065 is a potent anti-tumor antibiotic isolated from the culture broth of *Streptomyces zelensis*. CC-1065 is about 1000-fold more potent in vitro than are commonly used anti-cancer drugs, such as doxorubicin, methotrexate and vincristine (B. K. Bhuyan et al., 1982, *Cancer Res.*, 42, 3532-3537). CC-1065 and its analogs are disclosed in U.S. Pat. Nos. 6,372,738, 6,340,701, 5,846,545 and 5,585,499.

The cytotoxic potency of CC-1065 has been correlated with its alkylating activity and its DNA-binding or DNA-intercalating activity. These two activities reside in separate parts of the molecule. Thus, the alkylating activity is contained in the cyclopropapyrroloindole (CPI) subunit and the DNA-binding activity resides in the two pyrroloindole subunits.

Although CC-1065 has certain attractive features as a cytotoxic agent, it has limitations in therapeutic use. Administration of CC-1065 to mice caused a delayed hepatotoxicity leading to mortality on day 50 after a single intravenous dose of 12.5 μg/kg (V. L. Reynolds et al., 1986, *J. Antibiotics*, XXIX: 319-334). This has spurred efforts to develop analogs that do not cause delayed toxicity, and the synthesis of simpler analogs modeled on CC-1065 has been described (M. A. Warpehoski et al., 1988, *J. Med. Chem.*, 31: 590-603).

In another series of analogs, the CPI moiety was replaced by a cyclopropabenzindole (CBI) moiety (D. L. Boger et al., 1990, *J. Org. Chem.*, 55: 5823-5833; D. L. Boger et al., 1991, *BioOrg. Med. Chem. Lett.*, 1: 115-120). These compounds maintain the high in vitro potency of the parental drug, without causing delayed toxicity in mice. Like CC-1065, these compounds are alkylating agents that bind to the minor groove of DNA in a covalent manner to cause cell death. However, clinical evaluation of the most promising analogs, Adozelesin and Carzelesin, has led to disappointing results (B. F. Foster et al., 1996, *Investigational New Drugs*, 13: 321-326; I. Wolff et al., 1996, *Clin. Cancer Res.*, 2: 1717-1723). These drugs display poor therapeutic effects because of their high systemic toxicity.

The therapeutic efficacy of CC-1065 analogs can be greatly improved by changing the in vivo distribution through targeted delivery to the tumor site, resulting in lower toxicity to non-targeted tissues, and thus, lower systemic toxicity. In order to achieve this goal, conjugates of analogs and derivatives of CC-1065 with cell-binding agents that specifically target tumor cells have been described (U.S. Pat. Nos. 5,475,092; 5,585,499; 5,846,545). These conjugates typically display high target-specific cytotoxicity in vitro, and exceptional anti-tumor activity in human tumor xenograft models in mice (R. V. J. Chari et al., 1995, *Cancer Res.*, 55: 4079-4084).

Recently, prodrugs of CC-1065 analogs with enhanced solubility in aqueous medium have been described (European Patent Application No. 06290379.4). In these prodrugs, the phenolic group of the alkylating portion of the molecule is protected with a functionality that renders the drug stable upon storage in acidic aqueous solution, and confers increased water solubility to the drug compared to an unprotected analog. The protecting group is readily cleaved in vivo at physiological pH to give the corresponding active drug. In the prodrugs described in EP 06290379.4, the phenolic substituent is protected as a sulfonic acid containing phenyl carbamate which possesses a charge at physiological pH, and thus has enhanced water solubility. In order to further enhance water solubility, an optional polyethylene glycol spacer can be introduced into the linker between the indolyl subunit and the cleavable linkage such as a disulfide group. The introduction of this spacer does not alter the potency of the drug.

Methods for synthesizing CC-1065 analogs that may be used in the cytotoxic conjugates of the present invention, along with methods for conjugating the analogs to cell binding agents such as antibodies, are described in detail in EP 06290379.4 (whose content is incorporated herein by reference) and U.S. Pat. Nos. 5,475,092, 5,846,545, 5,585,499, 6,534,660 and 6,586,618 and in U.S. application Ser. Nos. 10/116,053 and 10/265,452.

Other Drugs

Drugs such as methotrexate, daunorubicin, doxorubicin, vincristine, vinblastine, melphalan, mitomycin C, chlorambucil, calicheamicin, tubulysin and tubulysin analogs, duocarmycin and duocarmycin analogs, dolastatin and dolastatin analogs are also suitable for the preparation of conjugates of the present invention. The drug molecules can also be linked to the antibody molecules through an intermediary carrier molecule such as serum albumin. Doxarubicin and Danorubicin compounds, as described, for example, in U.S. Ser. No. 09/740,991, may also be useful cytotoxic agents.

Therapeutic Composition

The invention also relates to a therapeutic composition for the treatment of a hyperproliferative disorder or inflammatory disease or an autoimmune disease in a mammal which comprises a therapeutically effective amount of a compound of the invention and a pharmaceutically acceptable carrier. In one embodiment said pharmaceutical composition is for the treatment of cancer, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoctanthoma, seminoma, thyroid follicular cancer and teratocarcinoma, and other cancers yet to be determined in which CD38 is expressed predominantly. In a preferred embodiment, the pharmaceutical compositions of the invention are used for the treatment of a cancer such as non-Hodgkin's lymphoma, Hodgkin's lymphoma, hairy cell leukemia, multiple myeloma, chronic lymphocytic leukemia, chronic myeloid leukemia, acute myeloid leukemia, or acute lymphocytic leukemia, in which CD38 is expressed, and other cancers yet to be determined in which CD38 is expressed predominantly. In another embodiment, the pharmaceutical composition of the invention can be used to treat autoimmune diseases, such as systemic lupus erythematosus, rheumatoid arthritis, multiple sclerosis, Crohn's disease, ulcerative colitis, gastritis, Hashimoto's thyroiditis, ankylosing spondylitis, hepatitis C-associated cryoglobulinemic vasculitis, chronic focal encephalitis, bullous pemphigoid, hemophilia A, membranoproliferative glomerulonephritis, Sjogren's syndrome, adult and juvenile dermatomyositis, adult polymyositis, chronic urticaria, primary biliary cirrhosis, idiopathic thrombocytopenic purpura, neuromyelitis optica, Graves' dysthyroid disease, bullous pemphigoid, membranoproliferative glomerulonephritis, Churg-Strauss syndrome, and asthma. In another embodiment, said pharmaceutical composition relates to other disorders such as, for example, graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.; and parasite infections, such as giardiasis, amoebiasis, schistosomiasis, and others as determined by one of ordinary skill in the art.

The instant invention provides pharmaceutical compositions comprising:

a) an effective amount of an antibody, antibody fragment or antibody conjugate of the present invention, and;

b) a pharmaceutically acceptable carrier, which may be inert or physiologically active.

As used herein, "pharmaceutically-acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH~7.4, containing or not containing about 1 mg/ml to 25 mg/ml human serum albumin, (2) 0.9% saline (0.9% w/v sodium chloride (NaCl)), and (3) 5% (w/v) dextrose; and may also contain an antioxidant such as tryptamine and a stabilizing agent such as Tween 20.

The compositions herein may also contain a further therapeutic agent, as necessary for the particular disorder being treated. Preferably, the antibody, antibody fragment or antibody conjugate of the present invention, and the supplementary active compound will have complementary activities, that do not adversely affect each other. In a preferred embodiment, the further therapeutic agent is an antagonist of epidermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP) or vascular endothelial growth factor (VEGF), or an antagonist of a receptor for epidermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP), or vascular endothelial growth factor (VEGF), including HER2 receptor, HER3 receptor, c-MET, and other receptor tyrosine kinases. In a preferred embodiment, the further therapeutic agent is an agent targeting clusters of differentiation (CD) antigens, including CD3, CD14, CD19, CD20, CD22, CD25, CD28, CD30, CD33, CD36, CD40, CD44, CD52, CD55, CD59, CD56, CD70, CD79, CD80, CD103, CD134, CD137, CD138, and CD152. In a preferred embodiment, the further therapeutic agent is a chemotherapeutic or immunomodulatory agent.

The compositions of the invention may be in a variety of forms. These include for example liquid, semi-solid, and solid dosage forms, but the preferred form depends on the intended mode of administration and therapeutic application. Typical preferred compositions are in the form of injectable or infusible solutions. The preferred mode of administration is parenteral (e.g. intravenous, intramuscular, intraperitoneal, subcutaneous). In a preferred embodiment, the compositions of the invention are administered intravenously as a bolus or by continuous infusion over a period of time. In another preferred embodiment, they are injected by intramuscular, subcutaneous, intra-articular, intrasynovial, intratumoral, peritumoral, intralesional, or perilesional routes, to exert local as well as systemic therapeutic effects.

Sterile compositions for parenteral administration can be prepared by incorporating the antibody, antibody fragment or antibody conjugate of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for parenteral administration may also be prepared in the form of sterile solid compositions which may be dissolved at the time of use in sterile water or any other injectable sterile medium.

The antibody, antibody fragment or antibody conjugate of the present invention may also be orally administered. As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablet) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

The doses depend on the desired effect, the duration of the treatment and the route of administration used; they are generally between 5 mg and 1000 mg per day orally for an adult with unit doses ranging from 1 mg to 250 mg of active substance. In general, the doctor will determine the appropriate dosage depending on the age, weight and any other factors specific to the subject to be treated.

Therapeutic Methods of Use

In another embodiment, the present invention provides a method for killing a $CD38^+$ cell by administering to a patient in need thereof an antibody which binds said CD38 and is able to kill said $CD38^+$ cell by apoptosis, ADCC, and/or CDC. Any of the type of antibodies, antibody fragments, or cytotoxic conjugates of the invention, may be used therapeutically. The invention thus includes the use of anti-CD38 monoclonal antibodies, fragments thereof, or cytotoxic conjugates thereof as medicaments.

In a preferred embodiment, antibodies, antibody fragments, or cytotoxic conjugates of the invention are used for the treatment of a hyperproliferative disorder or inflammatory disease or autoimmune disease in a mammal. In a more preferred embodiment, one of the pharmaceutical compositions disclosed above, and which contains an antibody, antibody fragment, or cytotoxic conjugate of the invention, is used for the treatment of a hyperproliferative disorder in a mammal. In one embodiment, the disorder is a cancer. In particular, the cancer is a metastatic cancer.

Accordingly, the pharmaceutical compositions of the invention are useful in the treatment or prevention of a variety of cancers, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyosarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoctanthoma, seminoma, thyroid follicular cancer and teratocarcinoma, and other cancers yet to be determined in which CD38 is expressed. Preferably, the disorder is NHL, BL, MM, B-CLL, ALL, TCL, AML, HCL, HL, or CML, in which CD38 is expressed, and other cancers yet to be determined in which CD38 is expressed predominantly. In another embodiment, the pharmaceutical composition of the invention can be used to treat autoimmune diseases, such as systemic lupus erythematosus, rheumatoid arthritis, multiple sclerosis, Crohn's disease, ulcerative colitis, gastritis, Hashimoto's thyroiditis, ankylosing spondylitis, hepatitis C-associated cryoglobulinemic vasculitis, chronic focal encephalitis, bullous pemphigoid, hemophilia A, membranoproliferative glomerulonephritis, Sjogren's syndrome, adult and juvenile dermatomyositis, adult polymyositis, chronic urticaria, primary biliary cirrhosis, idiopathic thrombocytopenic purpura, neuromyelitis optica, Graves' dysthyroid disease, bullous pemphigoid, membranoproliferative glomerulonephritis, Churg-Strauss syndrome, and asthma. In another embodiment, said pharmaceutical composition relates to other disorders such as, for example, graft rejections, such as renal transplant rejection, liver transplant rejection, lung transplant rejection, cardiac transplant rejection, and bone marrow transplant rejection; graft versus host disease; viral infections, such as mV infection, HIV infection, AIDS, etc.; and parasite infections, such as giardiasis, amoebiasis, schistosomiasis, and others as determined by one of ordinary skill in the art.

Similarly, the present invention provides a method for inhibiting the growth of selected cell populations comprising contacting target cells, or tissue containing target cells, with an effective amount of an antibody, antibody fragment or antibody conjugate of the present invention, or an antibody, antibody fragment or a therapeutic agent comprising a cytotoxic conjugate, either alone or in combination with other cytotoxic or therapeutic agents. In a preferred embodiment, the further therapeutic agent is an antagonist of epidermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP) or vascular endothelial growth factor (VEGF), or an antagonist of a receptor for epidermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP), or vascular endothelial growth factor (VEGF), including HER2 receptor, HER3 receptor, c-MET, and other receptor tyrosine kinases. In a preferred embodiment, the further therapeutic agent is an agent targeting clusters of differentiation (CD)

antigens, including CD3, CD14, CD19, CD20, CD22, CD25, CD28, CD30, CD33, CD36, CD40, CD44, CD52, CD55, CD59, CD56, CD70, CD79, CD80, CD103, CD134, CD137, CD138, and CD152. In a preferred embodiment, the further therapeutic agent is a chemotherapeutic or immunomodulatory agent.

The method for inhibiting the growth of selected cell populations can be practiced in vitro, in vivo, or ex vivo. As used herein, "inhibiting growth" means slowing the growth of a cell, decreasing cell viability, causing the death of a cell, lysing a cell and inducing cell death, whether over a short or long period of time.

Examples of in vitro uses include treatments of autologous bone marrow prior to their transplant into the same patient in order to kill diseased or malignant cells; treatments of bone marrow prior to its transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogeneic bone marrow or tissue prior to transplant in order to prevent graft versus host disease (GVHD). Treatment can be carried out as follows. Bone marrow is harvested from the patient or other individual and then incubated in medium containing serum to which is added the cytotoxic agent of the invention. Concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient by i.v. infusion according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the antibody, the epitope-binding antibody fragment, or the cytotoxic conjugate of the invention will be supplied as solutions that are tested for sterility and for endotoxin levels. Examples of suitable protocols of cytotoxic conjugate administration are as follows. Conjugates are given weekly for 4 weeks as an i.v. bolus each week. Bolus doses are given in 50 to 100 ml of normal saline to which 5 to 10 ml of human serum albumin can be added. Dosages will be 10 μg to 100 mg per administration, i.v. (range of 100 ng to 1 mg/kg per day). More preferably, dosages will range from 50 μg to 30 mg. Most preferably, dosages will range from 1 mg to 20 mg. After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Diagnostic

The antibodies or antibody fragments of the invention can also be used to detect CD38 in a biological sample in vitro or in vivo. In one embodiment, the anti-CD38 antibodies of the invention are used to determine the level of CD38 in a tissue or in cells derived from the tissue. In a preferred embodiment, the tissue is a diseased tissue. In a preferred embodiment of the method, the tissue is a tumor or a biopsy thereof. In a preferred embodiment of the method, a tissue or a biopsy thereof is first excised from a patient, and the levels of CD38 in the tissue or biopsy can then be determined in an immunoassay with the antibodies or antibody fragments of the invention. In another preferred embodiment, the level of CD38 is determined on a sample of a tissue or biopsy thereof, which can be frozen or fixed. The same method can be used to determine other properties of the CD38 protein, such as its cell surface levels, or its cellular localization.

The above-described method can be used to diagnose a cancer in a subject known to or suspected to have a cancer, wherein the level of CD38 measured in said patient is compared with that of a normal reference subject or standard. Said method can then be used to determine whether a tumor expresses CD38, which may suggest that the tumor will respond well to treatment with the antibodies, antibody fragments or antibody conjugates of the present invention. Preferably, the tumor is a NHL, BL, MM, B-CLL, ALL, TCL, AML, HCL, HL, or CML, in which CD38 is expressed, and other cancers yet to be determined in which CD38 is expressed predominantly.

The present invention further provides for monoclonal antibodies, humanized antibodies and epitope-binding fragments thereof that are further labeled for use in research or diagnostic applications. In preferred embodiments, the label is a radiolabel, a fluorophore, a chromophore, an imaging agent or a metal ion.

A method for diagnosis is also provided in which said labeled antibodies or epitope-binding fragments thereof are administered to a subject suspected of having a cancer or an inflammatory disease or an autoimmune disease, and the distribution of the label within the body of the subject is measured or monitored.

Kit

The present invention also includes kits, e.g., comprising a described cytotoxic conjugate and instructions for the use of the cytotoxic conjugate for killing of particular cell types. The instructions may include directions for using the cytotoxic conjugates in vitro, in vivo or ex vivo.

Typically, the kit will have a compartment containing the cytotoxic conjugate. The cytotoxic conjugate may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the cytotoxic conjugate prior to administering to a patient, and tools that aid in administering the conjugate to a patient.

EXAMPLES

The invention is now described by reference to the following examples, which are illustrative only, and are not intended to limit the present invention.

Example 1

Mouse CD38 Antibodies 300-19 cells, a pre-B cell line derived from a Balb/c mouse (M. G. Reth et al. 1985, *Nature*, 317: 353-355), stably expressing a high level of human CD38 were used for immunization of Balb/c VAF mice. Mice were subcutaneously immunized with about $5 \times 10^6$ CD38-expressing 300-19 cells per mouse every 2-3 weeks by standard immunization protocols used at ImmunoGen, Inc. The immunized mice were boosted with another dose of antigen three days before being sacrificed for hybridoma generation. The spleen from the mouse was collected according to standard animal protocols and was ground between two sterile, frosted microscopic slides to obtain a single cell suspension in RPMI-1640 medium. The spleen cells were pelleted, washed, and fused with murine myeloma P3X63Ag8.653 cells (J. F. Kearney et al. 1979, *J Immunol*, 123: 1548-1550) by using polyethylene glycol-1500 (Roche 783 641). The fused cells were resuspended in RPMI-1640 selection medium containing hypoxanthine-aminopterin-thymidine (HAT) (Sigma H-0262) and selected for growth in 96-well flat-bottomed culture plates (Corning-Costar 3596, 200 µL of cell suspension per well) at 37° C. (5% CO2). After 5 days of incubation, 100 µL of culture supernatant were removed from each well and replaced with 100 µL of RPMI-1640 medium containing hypoxanthine-thymidine (HT) supplement (Sigma H-0137). Incubation at 37° C. (5% CO2) was continued until hydridoma clones were ready for antibody screening. Other techniques of immunization and hybridoma production can also be used, including those described in J. Langone and H. Vunakis (Eds., *Methods in Enzymology*, Vol. 121, "Immunochemical Techniques, Part I"; Academic Press, Florida) and E. Harlow and D. Lane ("Antibodies: A Laboratory Manual"; 1988; Cold Spring Harbor Laboratory Press, New York).

By fluorescence activated cell sorting (FACS) using a Becton Dickinson FACSCalibur or a FACSArray machine, culture supernatants from the hybridoma were screened (with FITC or PE-conjugated anti-mouse IgG antiserum) for secretion of mouse monoclonal antibodies that bind to the CD38-expressing 300-19 cells, but not to the parental 300-19 cells. The hybridoma clones that tested positive were subcloned, and the isotype of each secreted anti-CD38 antibody was identified using commercial isotyping reagents (Roche 1493027). A total of 29 antibodies that were positive for CD38 binding were purified by Protein A or G chromatography using a standard protocol and then characterized further.

Example 2

Binding Characterization of Anti-CD38 Antibodies

FACS histograms demonstrating the binding of anti-CD38 antibodies, 38SB13, 38SB18, 38SB19, 38SB30, 38SB31, and 38SB39 to CD38-expressing 300-19 cells and the absence of binding to the parental 300-19 cells are shown in FIG. 1. 38SB13, 38SB18, 38SB19, 38SB30, 38SB31, or 38SB39 antibody (10 nM) was incubated for 3 h with either CD38-expressing 300-19 cells or the parental 300-19 cells ($1\text{-}2\times10^5$ cells per sample) in 100 µL ice-cold RPMI-1640 medium supplemented with 2% normal goat serum. Then, the cells were pelleted, washed, and incubated for 1 h on ice with FITC-conjugated goat anti-mouse IgG-antibody (Jackson Laboratory, 100 µL, 6 µg/mL in cold RPMI-1640 medium supplemented with 2% normal goat serum). The cells were pelleted again, washed, resuspended in 200 µL of PBS containing 1% formaldehyde, and analyzed using a FACSCalibur flow cytometer with CellQuest software (BD Biosciences).

The FACS histograms of CD38-expressing 300-19 cells incubated with 38SB13, 38SB18, 38SB19, 38SB30, 38SB31, or 38SB39 showed a strong fluorescence shift, compared to that of the corresponding negative control (cells incubated only with FITC-conjugated, goat anti-mouse IgG-antibody) (FIG. 1). Also, no significant fluorescence shift was detected when parental 300-19 cells were incubated with any of these antibodies. Similar results were obtained when the positive control anti-CD38 antibody, AT13/5 (Serotec, MCA1019) was used.

Figure 2:
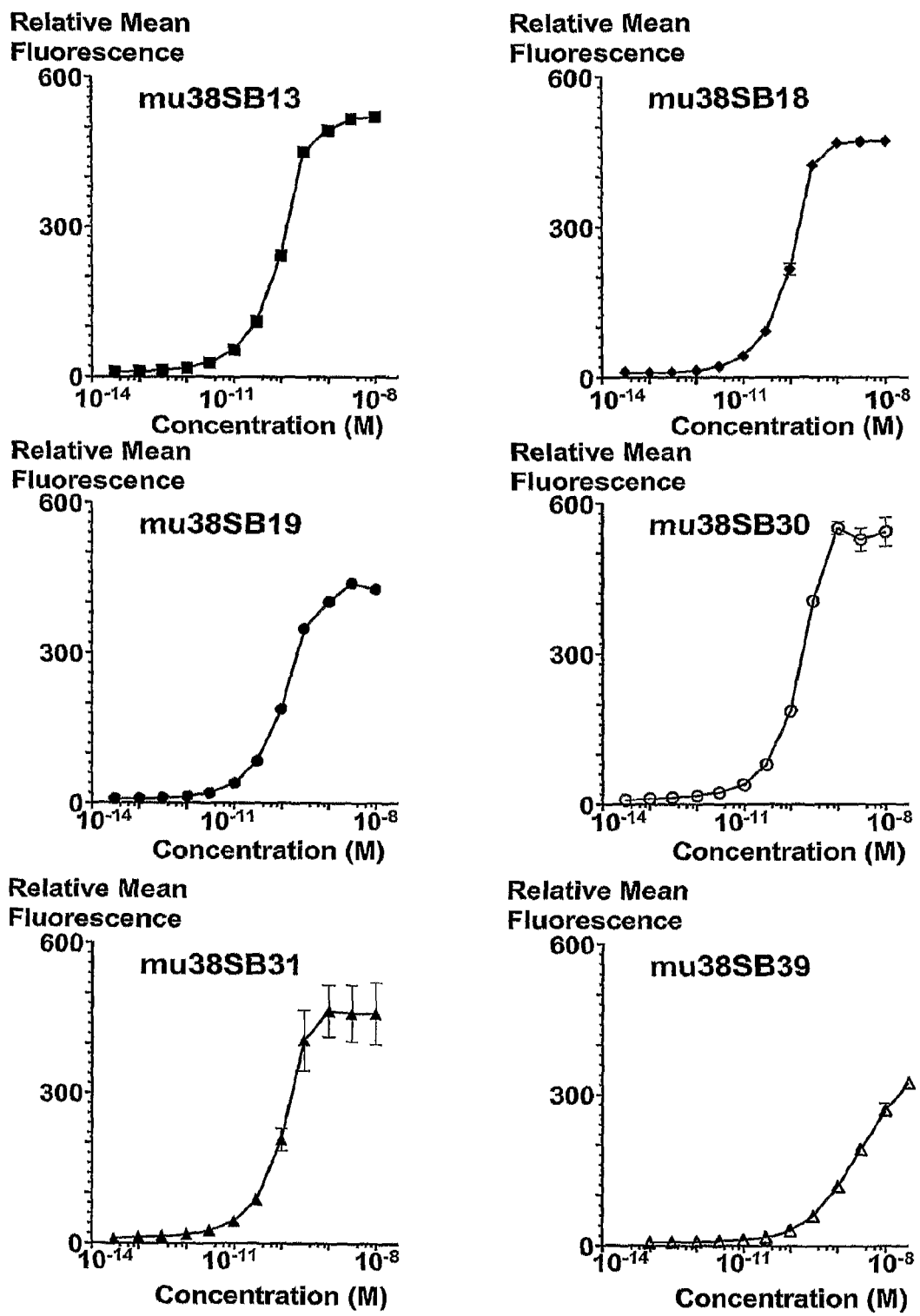
FIG. 2 shows the binding titration curves of 38SB13, 38SB18, 38SB19, 38SB30, 38SB31, and 38SB39 established with Ramos cells.

A strong fluorescence shift was also observed when Ramos (ATCC CRL 1596) lymphoma cells were incubated with 38SB13, 38SB18, 38SB19, 38SB30, 38SB31, or 38SB39 (FIG. 1). The values for the apparent dissociation constants (KD) of 38SB13, 38SB18, 38SB19, 38SB30, 38SB31, and 38SB39 for the binding to Ramos cells were estimated from the FACS analysis curves shown in FIG. 2, using the non-linear regression method for sigmoidal dose response curves (GraphPad Prizm, version 4, software, San Diego, Calif.). The values are as follows: 0.10 nM, 0.10 nM, 0.12 nM, 0.16 nM, 0.11 nM, and 3.03 nM, respectively.

Example 3

Induction of Apoptosis of Ramos and Daudi Lymphoma Cells, by 38SB13, 38SB18, 38SB19, 38SB30, 38SB31, and 38SB39 Antibodies The anti-CD38 antibodies, 38SB13, 38SB18, 38SB19, 38SB30, 38SB31, and 38SB39 induced apoptosis of Ramos and Daudi (ATCC CCL-213) lymphoma cell lines and the MOLP-8 multiple myeloma cell line (DSMZ ACC 569). The degree of apoptosis was measured by FACS analysis after staining with FITC conjugates of Annexin V (Biosource PHN1018) and with TO-PRO-3 (Invitrogen T3605). Annexin V binds phosphatidylserine on the outside but not on the inside of the cell membrane bilayer of intact cells. In healthy, normal cells, phosphatidylserine is expressed on the inside of the membrane bilayer, and the transition of phosphatidylserine from the inner to the outer leaflet of the plasma membrane is one of the earliest detectable signals of apoptosis. Binding of Annexin V is thus a signal for the induction of apoptosis. TO-PRO-3 is a monomeric cyanine nucleic acid stain that can only penetrate the plasma membrane when the membrane integrity is breached, as occurs in the later stages of apoptosis.

Exponentially growing cells were plated at about $2\times10^5$ cells/mL in 24-well plates in RMPI-1640 medium supplemented with 10% fetal bovine serum (FBS), 2 mM L-glutamine, and 50 µg/mL gentamycin (denoted below as complete RMPI-1640 medium). Cells were generally grown in complete RMPI-1640 medium, unless stated otherwise. Cells were incubated with anti-CD38 antibodies (10 nM) for 24 h at 37° C. in a humidified atmosphere containing 5% $CO_2$. The cells were then pelleted, washed twice with 500 µL PBS, resuspended in 100µL binding buffer (provided in the Annexin V-FITC kit), containing 5 µL of Annexin V-FITC, and incubated for 15 min on ice. Then, 400 µL of binding buffer and TO-PRO-3 (to a final concentration of 1 µM) was added to the mix, and the cell-associated fluorescence of FITC and TO-PRO-3 was immediately measured by FACS. Four thousand events were collected for each sample. The dot plots for fluorescence of TO-PRO-3 (FL4-H; y-axis) and fluorescence of Annexin V-FITC (FL1-H; x-axis) were generated using CellQuest software.

Figure 3:
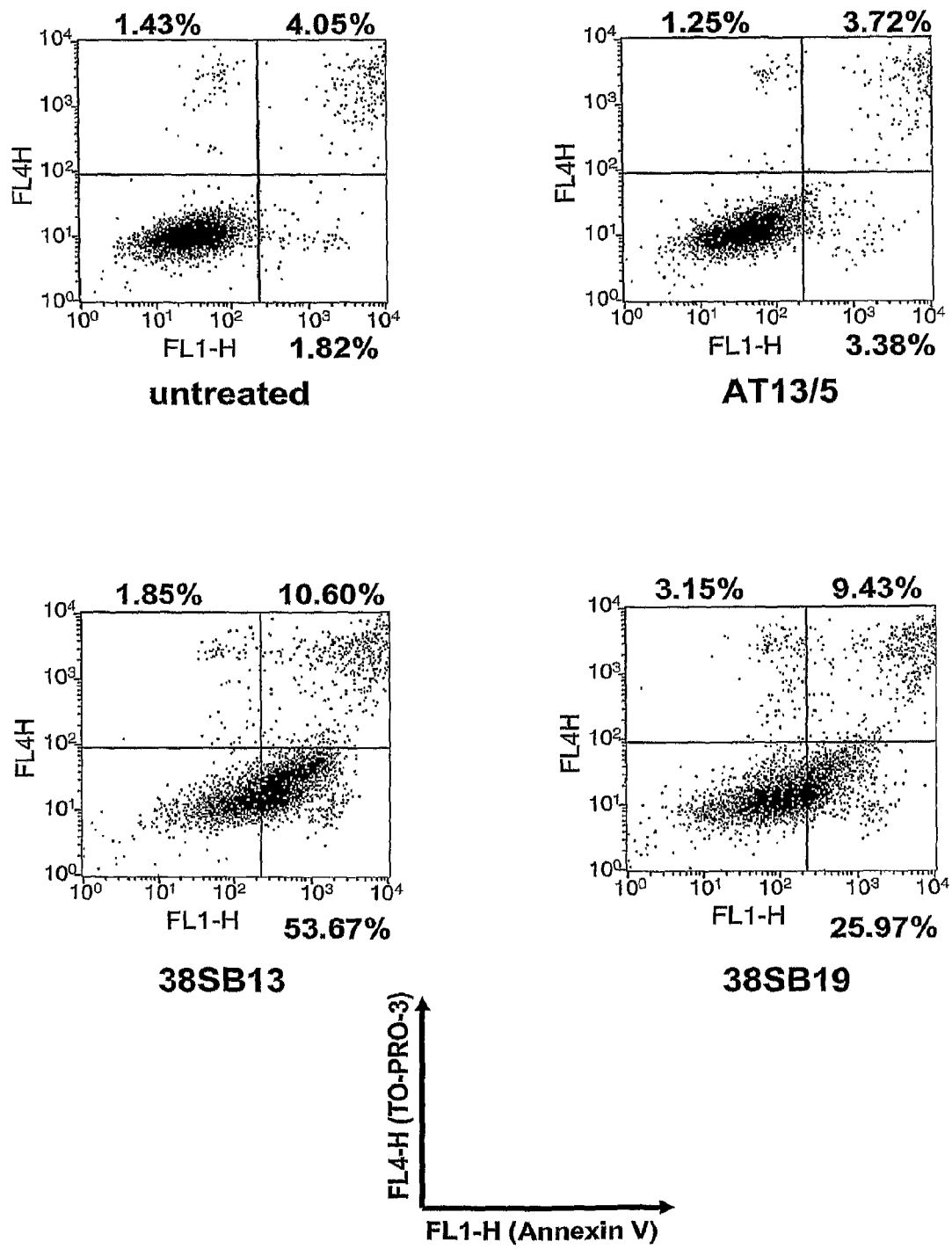
FIG. 3 shows FACS dot plots (FL4-H; TO-PRO-3 staining; y-axis and FL1-H; Annexin V-FITC staining; x-axis) of Ramos cells undergoing apoptosis after incubation with 38SB13, 38SB19, or AT13/5 (10 nM) for 24 h.
Figure 4A:
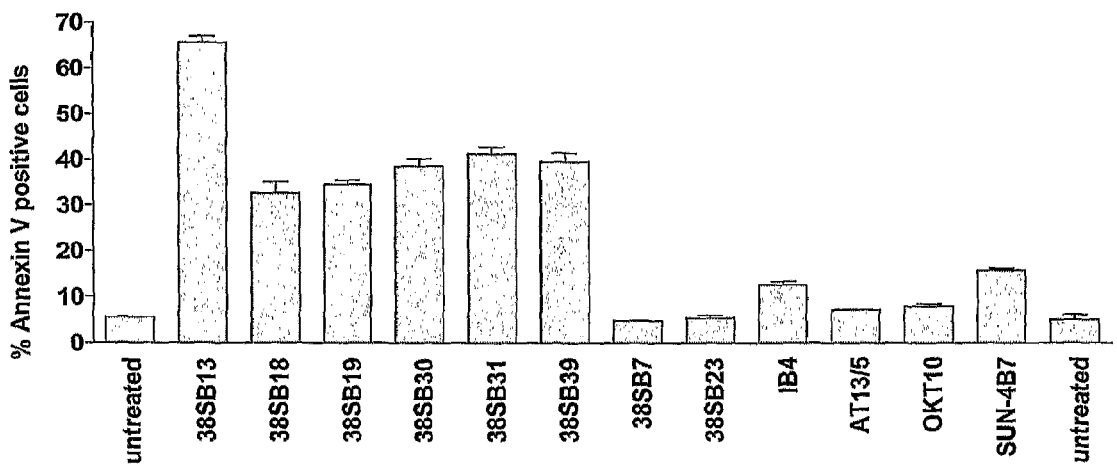
FIG. 4A shows the average percentages of Ramos cells undergoing apoptosis after a 24-h incubation with 38SB13, 38SB18, 38SB19, 38SB30, 38SB31, 38SB39, 38SB7, 38SB23, IB4, AT13/5, OKT10, or SUN-4B7. The average percentage of Annexin V-positive cells (y-axis; includes both TO-PRO-3 positive and negative cells) from duplicate samples were plotted.
Figure 4B:
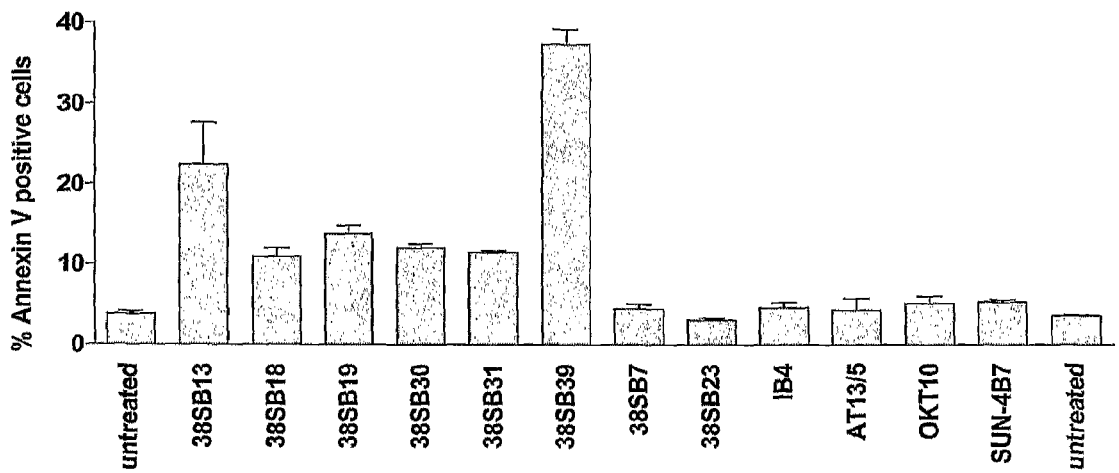
FIG. 4B shows the average percentages of Daudi cells undergoing apoptosis after a 24-h incubation with the same set of antibodies as in FIG. 4A.
Figure 4C:
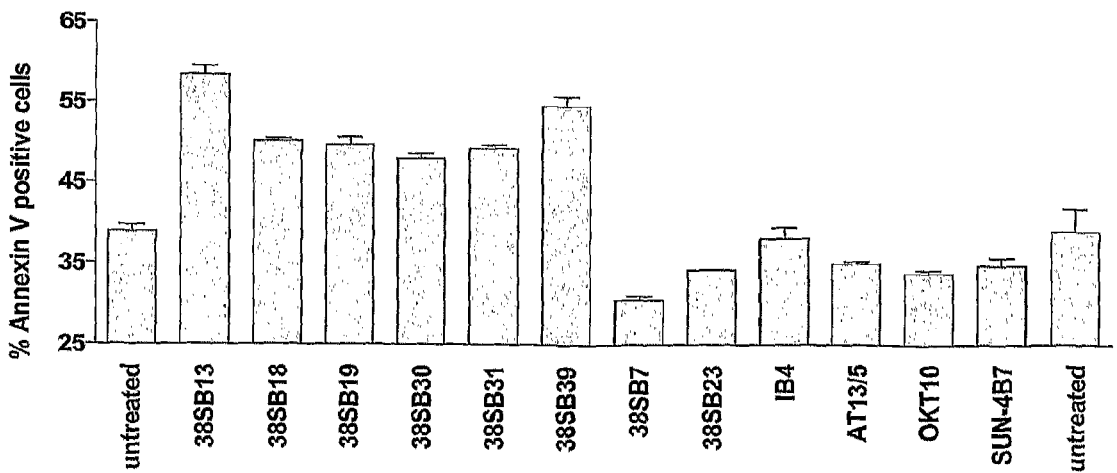
FIG. 4C shows the average percentages of Molp-8 cells undergoing apoptosis after a 24-h incubation with the same set of antibodies as in FIG. 4A.

The results are shown in FIGS. 3 and 4. FIG. 3 gives an example of such a dot plot for Daudi cells after a 24-h incubation with various anti-CD38 antibodies. The average percentages of Annexin V-positive cells (includes both TO-PRO-3 positive and negative cells) from duplicate samples were determined from these plots and are shown in FIG. 4. Unexpectedly, 38SB13, 38SB18, 38SB19, 38SB30, 38SB31, and 38SB39 showed strong apoptotic activities. Greater than 30% of Daudi cells exposed to any of these antibodies were Annexin V-positive, compared to only about 6% of untreated cells (FIGS. 3 and 4A). 38SB13, 38SB18, 38SB19, 38SB30, 38SB31, and 38SB39 showed at least 2.4-fold stronger apoptotic activities (24% after subtraction of the non-treated control value) than prior art murine CD38 antibodies tested at the same concentration of 10 nM, (AT13/5, OKT10, IB4, and SUN-4B7, less than 10% Annexin V-positive after subtraction of the non-treated control value) and two other anti-CD38 antibodies generated in our laboratory, (38SB7 and 38SB23, not higher than non-treated control, i.e. about 6% Annexin V-positive) (FIG. 4A). AT13/5 was purchased from Serotec (MCA1019), and OKT10 was produced and purified from hybridoma (ATCC CRL-8022). IB4 and SUN-4B7 was a gift from Prof. F. Malavasi, University of Turin, Italy. Similarly, 38SB13, 38SB18, 38SB19, 38SB30, 38SB31, and 38SB39 anti-CD38 antibodies displayed at least 3.5-fold stronger pro-apoptotic activity on another lymphoma cell line, Ramos (7% or more Annexin-V-positive after subtraction of the non-treated control value) than either prior art murine CD38 antibodies, AT13/5, OKT10, IB4, and SUN-4B7, or two other new anti-CD38 antibodies, 38SB7 and 38SB23 (less than 2% Annexin V-positive after subtracting the non-treated control value) (FIG. 4B). Finally, 38SB13, 38SB18, 38SB19, 38SB30, 38SB31, and 38SB39 anti-CD38 antibodies displayed strong pro-apoptotic activity on the multiple myeloma cell line MOLP-8 (FIG. 4C). Approximately 50% of MOLP-8 cells treated with these antibodies were Annexin V-positive, compared to about 39% of untreated cells. In contrast, treatment with any of the prior art murine CD38 antibodies, AT13/5, OKT10, IB4, and SUN-4B7, or two other new anti-CD38 antibodies, 38SB7 and 38SB23 resulted on no increase in the portion of apoptotic cells.

Example 4

Cloning and Sequencing of the Light and Heavy Chains of Anti-CD38 Antibodies 38SB19 Antibody RNA preparation from hybridoma cells that produces the 38SB19 antibody Preparations of total RNA were obtained from $5 \times 10^6$ hybridoma cells, which produce 38SB19 antibody, using Qiagen's RNeasy miniprep kit. Briefly, $5 \times 10^6$ cells were pelleted and resuspended in 350 µL RLT buffer (containing 1% β-mercaptoethanol). The suspension was homogenized by passing it through a 21.5 gauge needle and syringe roughly 10-20 times or until it was no longer viscous. Ethanol (350 µL of 70% aqueous ethanol) was added to the homogenate, which was mixed well. The solution was transferred to a spin column, placed in a 2-mL collection tube and spun at >8000×g for 15 seconds. The column was washed twice with 500 µL RPE buffer, then transferred to a fresh tube and eluted with 30 µL RNase free water and a 1-minute spin. The eluate (30 µL) was placed back on the column for a second 1-minute elution spin. An aliquot of the 30 µL eluate was diluted with water and used to measure the UV absorption at 260 nm for RNA quantitation cDNA Preparation with Reverse Transcriptase (RT) Reaction The variable region 38SB19 antibody cDNA was generated from the total RNA using Invitrogen's SuperscriptII kit. The kit protocols were followed closely, utilizing up to 5 µg of total RNA from the Qianeasy mini preps. Briefly, the RNA, 1 µL random primers, and 1 µL dNTP mix were brought up to 12 µL with RNase free sterile distilled water and incubated at 65° C. for 5 minutes. The mix was then put on ice for at least 1 minute. Next 4 µL of 5× reaction buffer, 2 µL 0.1 M DTT, and 1 µL RNaseOUT were added and the mix was incubated at 25° C. for 2 minutes in an MJ Research thermalcycler. The thermalcycler was paused so that 1 µL of SuperscriptII enzyme could be added and then restarted for an additional 10 minutes at 25° C. before shifting to 55° C. for 50 minutes. The reaction was heat inactivated by heating to 70° C. for 15 min and the RNA was removed by adding 1 µL RNase H and incubating at 37° C. for 20 minutes.

Degenerate PCR Reactions

The procedure for the first round degenerate PCR reaction on the cDNA derived from hybridoma cells was based on methods described in Wang et al. (2000) and Co et al. (1992). The primers for this round (Table 2) contain restriction sites to facilitate cloning into the pBluescriptII plasmids.

The PCR reaction components (Table 3) were mixed on ice in thin walled PCR tubes and then transferred to an MJ research thermalcycler preheated and paused at 94° C. The reactions were performed using a program derived from Wang et al., 2000 as follows:

Name: Wang45
94° C. 3:00 min
94° C. 0:15 sec
45° C. 1:00 min
72° C. 2:00 min
Goto 2 29 times
72° C. 6:00 min
4° C. for ever
end The PCR reaction mixtures were then run on a 1% low melt agarose gel, the 300 to 400 bp bands were excised, purified using Zymo DNA mini columns, and sent to Agencourt biosciences for sequencing. The respective 5' and 3' PCR primers were used as sequencing primers to generate the 38SB19 variable region cDNAs from both directions.

Cloning the 5' End Sequence

Since the degenerate primers used to clone the 38SB19 variable region light chain and heavy chain cDNA sequences alters the 5' end sequences, additional sequencing efforts were needed to decipher the complete sequences. The preliminary cDNA sequence from the methods described above were used to search the NCBI IgBlast site for the murine germline sequences from which the 38SB19 sequence is derived. PCR primers were designed (Table 3) to anneal to the leader sequence of the murine antibody so that a new PCR reaction could yield the complete variable region cDNA, unaltered by the PCR primers. The PCR reactions, band purifications, and sequencing were performed as described above.

Peptide Analysis for Sequence Confirmation

The cDNA sequence information for the variable region was combined with the germline constant region sequence to obtain full length antibody cDNA sequences. The molecular weights of the heavy chain and light chain were then calculated and compared with the molecular weights obtained by LC/MS analyses of the murine 38SB19 antibody.

Table 4 gives the calculated mass from the cDNA sequences for 38SB19 LC and HC together with the values measured by LC/MS. The molecular weight measurements are consistent with the cDNA sequences for both the 38SB19 light and heavy chain.

Example 5

Recombinant Expression of hu38SB19 Antibodies

Figure 5A:
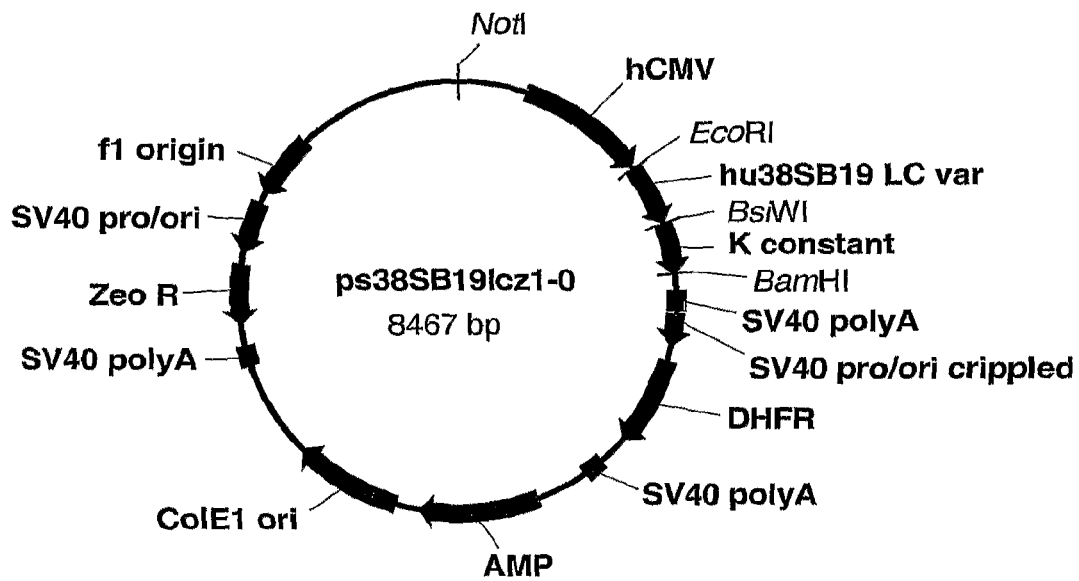
FIG. 5A shows a diagram of the human expression vector used to express hu38SB19-LC.
Figure 5B:
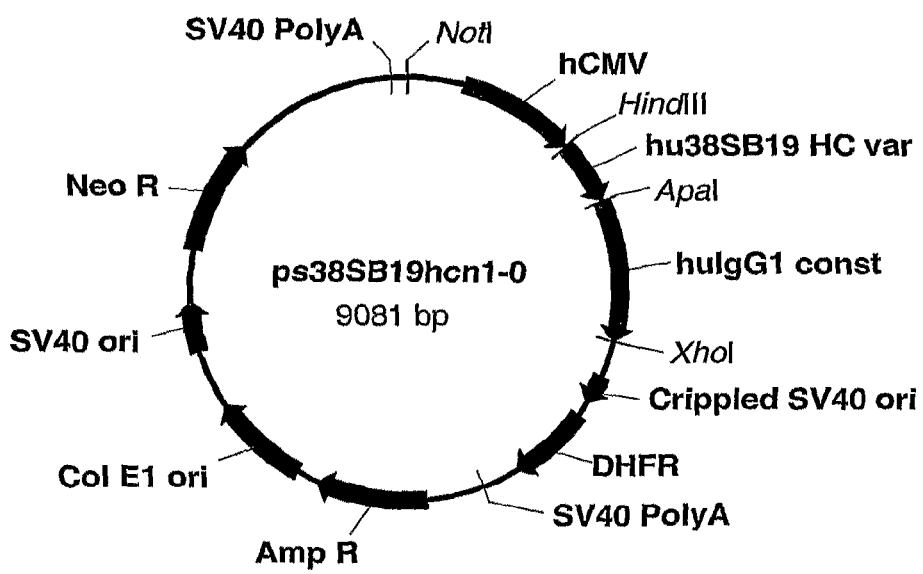
FIG. 5B shows a diagram of the human expression vector used to express hu38SB19-HC.
Figure 5C:
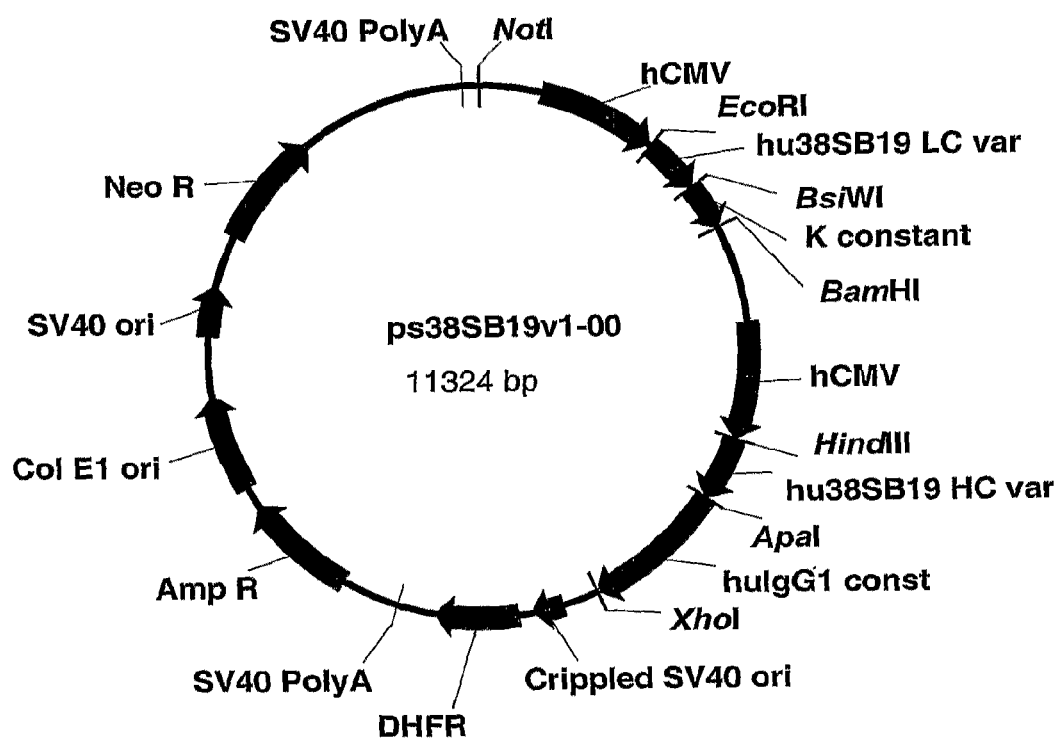
FIG. 5C shows a diagram of the human expression vector used to express both hu38SB19LC and hu38SB19HC.

The variable region sequences for hu38SB19 were codon-optimized and synthesized by Blue Heron Biotechnology. The sequences are flanked by restriction enzyme sites for cloning in-frame with the respective constant sequences in both single chain and the tandem dual chain mammalian expression plasmids. The light chain variable region is cloned into EcoRI and BsiWI sites in both the ps38SB19LCZv1.0 and ps38SB19v1.00 plasmids (FIGS. 5A and 5C). The heavy chain variable region is cloned into the HindIII and Apa1 sites in both the ps38SB19HCNv1.0 and ps38SB19v1.00 plasmids (FIGS. 5B and 5C). These plasmids can be used to express hu38SB19 in either transient or stable transfections in mammalian cells. Similar expression vector constructs were used to produce other chimeric and humanized antibodies.

Transient transfections to express hu38SB19 in HEK-293T cells were performed using $CaPO_4$ reagents from BD biosciences. The supplied protocols were slightly modified for enhanced expression yields. Briefly, $2\times10^6$ HEK-293T cells were plated on 10 cm tissue culture plates coated with polyethyleneimine (PEI) 24 h prior to transfection. The transfection began by washing the cells with PBS and replacing the media with 10 mL DMEM (Invitrogen) with 1% Ultra Low IgG FBS (Hyclone). Solution A (10 μg DNA, 86.8 μL $Ca^{2+}$ solution, and up to 500 μL with $H_2O$) was added drop wise to Solution B while vortexing. The mixture was incubated at RT for 1 min and 1 mL of the mixture was added drop wise to each 10 cm plate. Approximately 16 h post transfection, media was replaced with 10 mL fresh DMEM with 1% Ultra Low IgG FBS. Approximately 24 hours later 2 mM sodium butyrate was added to each 10 cm plate. The transfection was harvested 4 days later.

Supernatant was prepared for Protein A affinity chromatography by the addition of 1/10 volume of 1 M Tris/HCl buffer, pH 8.0. The pH-adjusted supernatant was filtered through a 0.22 μm filter membrane and loaded onto a Protein A Sepharose column (HiTrap Protein A HP, 1 mL, Amersham Biosciences) equilibrated with binding buffer (PBS, pH 7.3). A Q-Sepharose precolumn (10 mL) was connected upstream of the Protein A column during sample loading to reduce contamination from cellular material such as DNA. Following sample loading, the precolumn was removed and the Protein A column orientation was reversed for wash and elution. The column was washed with binding buffer until a stable baseline was obtained with no absorbance at 280 nm. Antibody was eluted with 0.1 M acetic acid buffer containing 0.15 M NaCl, pH 2.8, using a flow rate of 0.5 mL/min. Fractions of approximately 0.25 mL were collected and neutralized by the addition of 1/10 volume of 1 M Tris/HCl, pH 8.0. The peak fraction(s) was dialysed overnight twice against PBS and purified antibody was quantitated by absorbance at $OD_{280}$. Humanized and chimeric antibodies can also be purified using a Protein G column with slightly different procedures.

All the described chimeric and humanized anti-CD38 antibodies were expressed and purified in similar procedures as described above.

Example 6

Antibody-dependent Cell-mediated Cytotoxicity (ADCC) Activities of Chimeric Anti-CD38 Antibodies Since some anti-CD38 antibodies have been previously shown to have ADCC and/or CDC activity as chimeric or humanized antibodies with human IgG1 constant regions (J. H. Ellis et al. 1995, *J Immunol*, 155: 925-937; F. K. Stevenson et al. 1991, *Blood*, 77: 1071-1079; WO 2005/103083), the chimeric versions of 38SB13, 38SB18, 38SB19, 38SB30, 38SB31, and 38SB39, consisting of murine variable regions and the human IgG1/IgKappa constant region, were made and tested for ADCC and/or CDC activities. Ch38SB13, ch38SB18, ch38SB19, ch38SB30, ch38SB31, and ch38SB39 were first tested for ADCC using Ramos cells as target cells and human natural killer (NK) cells as effector cells. A lactate dehydrogenase (LDH) release assay was used to measure cell lysis (R. L. Shields et al., 2001, *J Biol Chem*, 276: 6591-6604).

The NK cells were first isolated from human blood (from a normal donor; purchased from Research Blood Components, Inc., Brighton, Mass.) using a modified protocol for NK Isolation Kit II (Miltenyi Biotech). Blood was diluted 2-3-fold with Hank's Balanced Salt Solution (HBSS). Twenty five mL of diluted blood was carefully layered over 25 mL of Ficoll Paque in a 50 mL conical tube and centrifuged at 400 g for 45 min at 19° C. The peripheral blood mononuclear cells (PBMC) were collected from the interface, transferred into a new conical 50 mL tube, and washed once with HBSS. The PBMC were resuspended in 2 mL of NK-isolation buffer, and then 500 μL of Biotin-Antibody Cocktail (from the NK-isolation kit, 130-091-152, Miltenyi Biotech) were added to the cell suspension. The Biotin-Antibody Cocktail contains biotinylated antibodies that bind to the lymphocytes, except for NK cells. The mixture was incubated at 4° C. for 10 min, and then 1.5 mL of NK-isolation buffer (PBS, 0.1% BSA, 1 mM EDTA) and 1 mL of Anti-Biotin Micro Beads was added. The cell-antibody mixture was incubated for another 15 min at 4° C. Next, cells were washed once with 50 mL of NK-isolation buffer and resuspended in 3 mL of NK-isolation buffer. Then, MACS LS column (on the MACS separator, Miltenyi Biotech) was pre-washed with 3 mL of NK-isolation Buffer. The cell suspension was then applied onto the LS column. The effluent (fraction with unlabeled cells) was collected into a new 50-mL conical tube. The column was washed 3 times with 3 mL of NK-isolation Buffer. The entire effluent was collected into the same tube and washed once with 50 mL of NK-isolation Buffer. NK cells were plated into 30 mL of RPMI-1640 supplemented with 5% fetal bovine serum, 50 μg/mL gentamycin.

Various concentrations of ch38SB13, ch38SB18, ch38SB19, ch38SB30, ch38SB31, and ch38SB39 antibodies in RPMI-1640 medium supplemented with 0.1% BSA, 20 mM HEPES, pH 7.4, and 50 μg/mL gentamycin (denoted below as RHBP medium) were aliquoted (50 μL/well) into a round bottom 96-well plate. The target Ramos cells were resuspended at $10^6$ cells/mL in RHBP medium and added to each well (100 μL/well) containing antibody dilutions. The plate containing target cells and antibody dilutions was incubated for 30 min at 37° C. NK cells (50 μL/well) were then added to the wells containing the target cells typically at a ratio of 1 target cell to 3-6 NK cells ratio. RHBP medium (50 μL/well) was added to the control wells with NK cells. Also, 20 μL of Triton X-100 solution (RPMI-1640 medium, 10% Triton X-100) was added to the 3 wells containing only target cells without antibody, to determine the maximum possible LDH release. The mixtures were incubated at 37° C. for 4 h, then centrifuged for 10 min at 1200 rpm, and 100 μL of the supernatant was carefully transferred to a new flat-bottom 96-well plate. LDH reaction mixture (100 μL/well) from Cytotoxicity Detection Kit (Roche 1 644 793) was added to each well and incubated at room temperature for 5-30 min. The optical density of samples was measured at 490 nm ($OD_{490}$). The percent specific lysis of each sample was determined by ascribing 100% lysis to the $OD_{490}$ value of Triton X-100-treated samples and 0% lysis to the $OD_{490}$ value of the untreated control sample containing only target cells. The samples containing only NK cells gave negligible $OD_{490}$ readings.

Figure 6A:
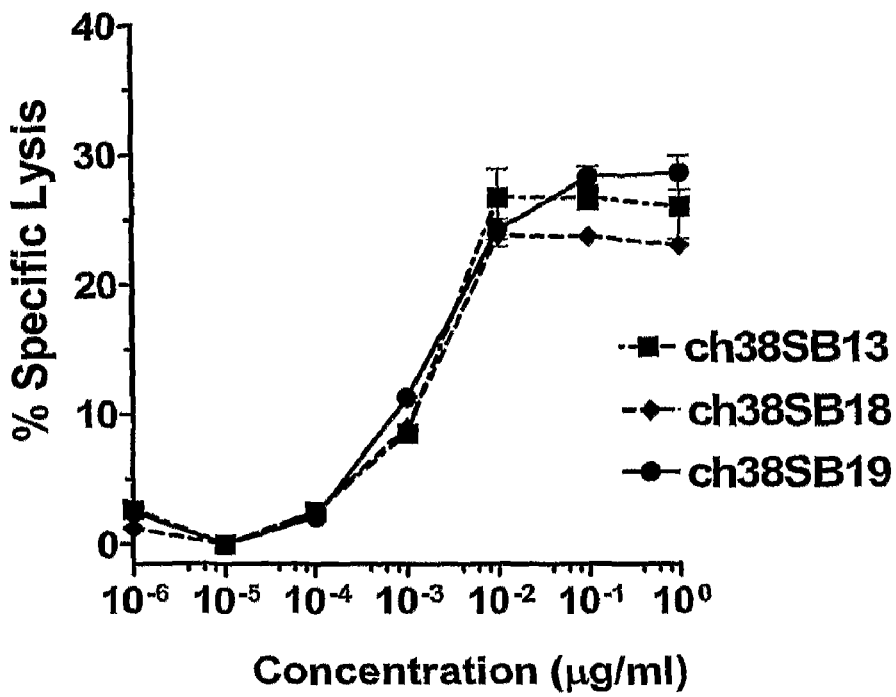
FIG. 6A shows ADCC activities mediated by the antibodies, ch38SB13, ch38SB18, and ch38SB19, towards Ramos cells.
Figure 6B:
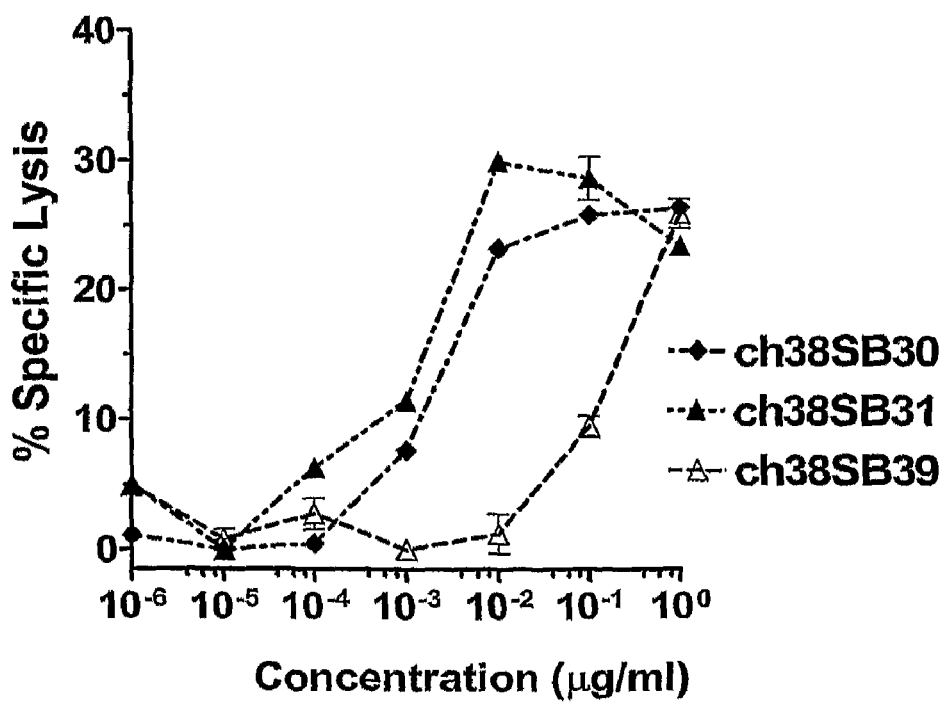
FIG. 6B shows ADCC activities mediated by the antibodies, ch38SB30, ch38SB31, and ch38SB39 towards Ramos cells.
Figure 7A:
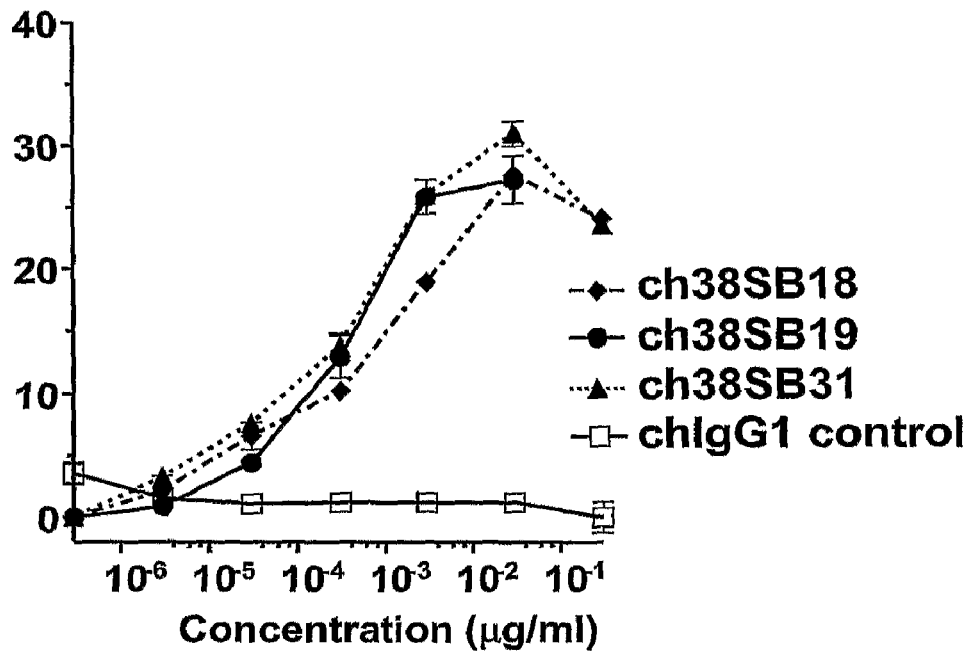
FIG. 7A) shows ADCC activities mediated by the antibodies ch38SB18, ch38SB19, ch38SB31, and non-binding chimeric human IgG1 control antibody towards LP-1 multiple myeloma cells.
Figure 7B:
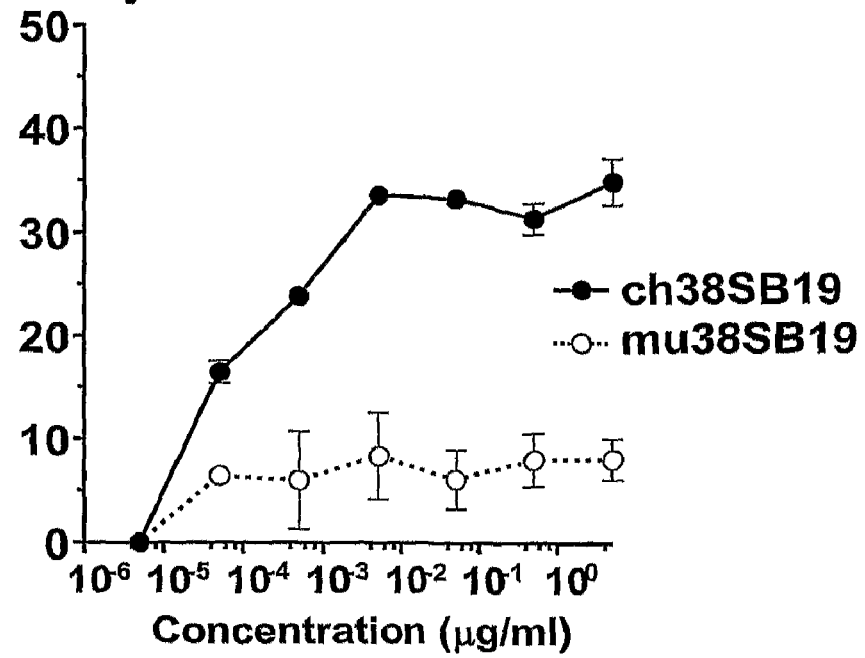
FIG. 7B) compares ADCC activities mediated by the antibodies ch38SB19 and murine 38SB19 towards Daudi cells.
Figure 8A:
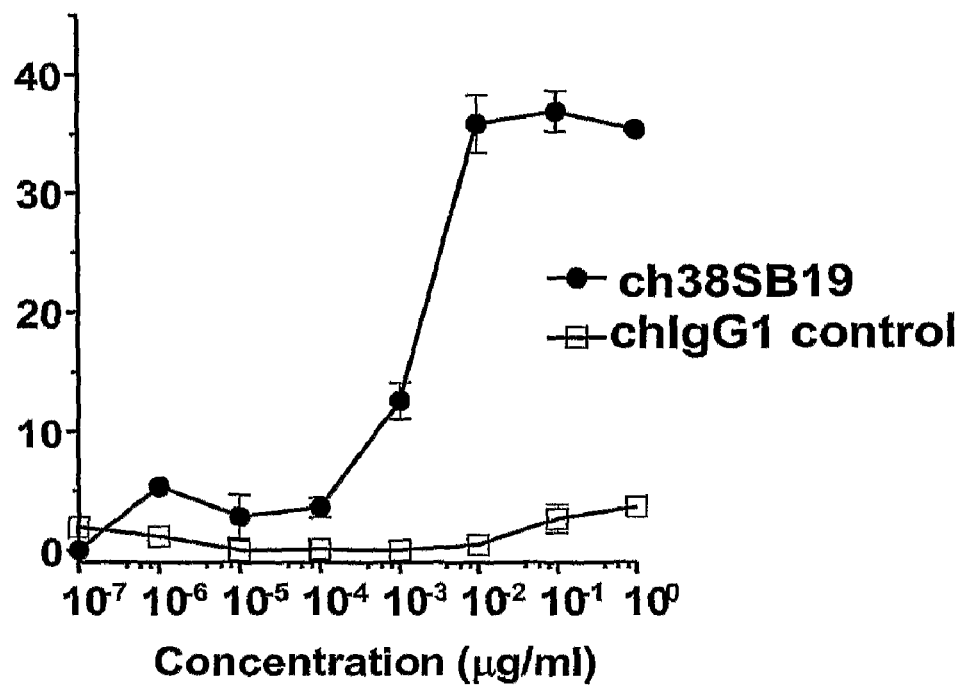
FIG. 8A shows ADCC activities mediated by the ch38SB19 antibody and by non-binding chimeric human IgG1 control antibody towards NALM-6 B-ALL cells.
Figure 8B:
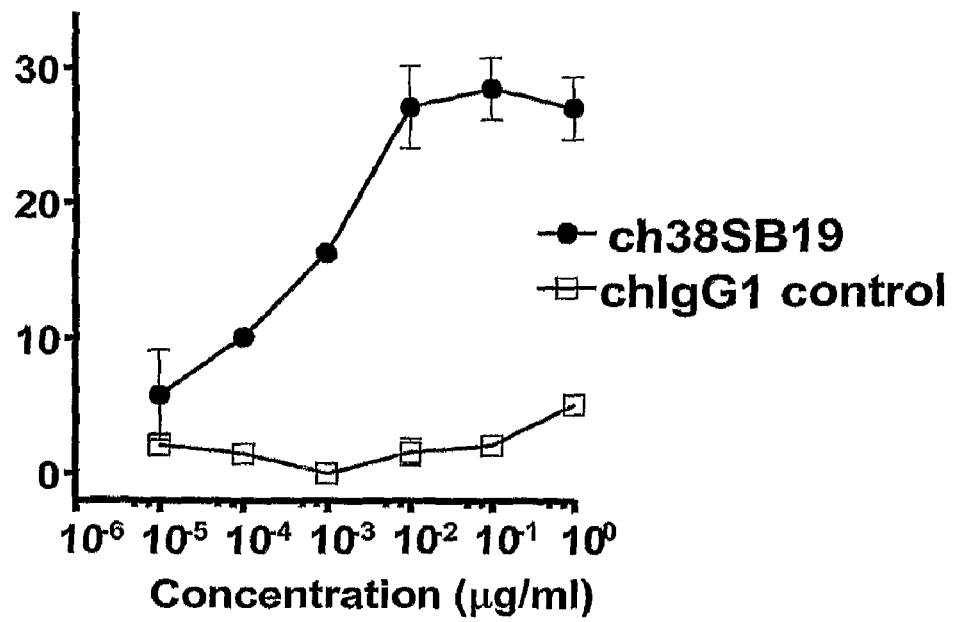
FIG. 8B shows ADCC activities mediated by the ch38SB19 antibody and by non-binding chimeric human IgG1 control antibody towards MOLT-4 T-ALL cells.

When tested with Ramos target cells and NK effector cells, chimeric anti-CD38 antibodies showed very potent ADCC activities (FIG. 6). The $EC_{50}$ values were estimated by a non-linear regression method with sigmoidal dose response curves and found to be as follows: 0.0013 µg/mL for ch38SB13, 0.0013 µg/mL for ch38SB18, 0.0018 µg/mL for ch38SB19, 0.0022 µg/mL for ch38SB30, 0.0012 µg/mL for ch38SB31, 0.1132 µg/mL for ch38SB39. Chimeric anti-CD38 antibodies also showed potent ADCC activity on LP-1 (DSMZ ACC 41) multiple myeloma cells ($EC_{50}$ values: 0.00056 µg/mL for ch38SB18; 0.00034 µg/mL for ch38SB19; 0.00024 µg/mL for ch38SB31) (FIG. 7A). Ch38SB19 also efficiently killed Daudi lymphoma cells (FIG. 7B), NALM-6 B-ALL cells (DSMZ ACC 128) (FIG. 8A), and MOLT-4 T-ALL cells (ATTC CRL-1582) (FIG. 8B) by ADCC, suggesting anti-CD38 antibodies with unusually potent apoptotic activity also have potent ADCC activity against various tumor cells derived from various hematopoietic malignancies. Also, a non-binding IgG1 control antibody (rituximab, Biogenidec) (FIGS. 7A, 8A, and 8B) or mu38SB19 (FIG. 7B) in the same experiment had no significant ADCC activity.

Example 7

CDC Activities of Chimeric Anti-CD38 Antibodies

The CDC activities of ch38SB13, ch38SB18, ch38SB19, ch38SB30, ch38SB31, and ch38SB39 were measured based on a method modified from (H. Gazzano-Santoro et al./1997, *J. Immunol. Methods*, 202: 163-171). Human complement was lyophilized human complement serum (Sigma-Aldrich S1764) that was reconstituted with sterile purified water as indicated by the manufacturer and then diluted five-fold with RHBP media immediately before the experiment. Target cells suspended at $10^6$ cells/mL in RHBP medium were aliquoted into wells of a flat-bottom 96-well tissue culture plate (50 µL/well). Then, 50 µL of various concentrations (from 10 nM to 0.001 nM) of the anti-CD38 antibodies in RHBP medium were added (one antibody per sample), which was followed by 50 µL/well of complement solution. The plate was then incubated for 2 h at 37° C. in a humidified atmosphere containing 5% $CO_2$, after which time 50 µL of 40% Alamar Blue reagent (Biosource DAL 1100) diluted in RHBP (10% final) was added to each well to measure the viability of the cells. Alamar Blue monitors the reducing capacity of the viable cells. The plate was incubated for 5-18 h at 37° C. before measuring the fluorescence (in relative fluorescence units, RFU) at 540/590 nm. The percentage of specific cell viability for each sample was determined by first correcting the experimental values for background fluorescence by subtracting the background RFU value (wells with medium only, without any cells) from the RFU values for each sample, and then, dividing the corrected RFU values by the corrected RFU value of untreated cell samples.

Figure 9:
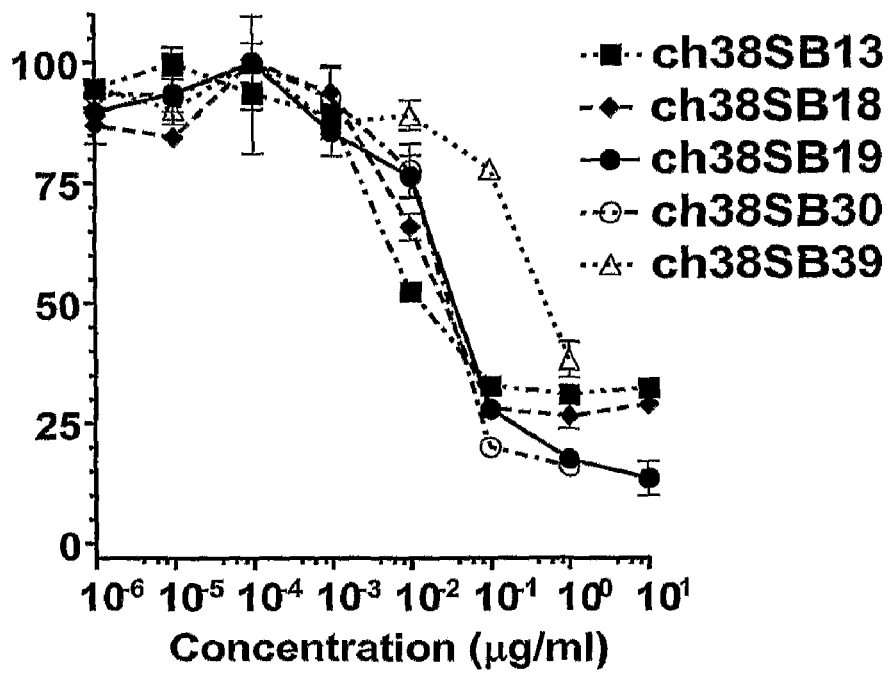
FIG. 9A shows CDC activities mediated by the antibodies ch38SB13, ch38SB18, ch38SB19, ch38SB30, and ch38SB39 towards Raji-IMG cells.
FIG. 9B shows CDC activities mediated by the antibodies ch38SB19 and ch38SB31 towards Raji-IMG cells.
Figure 9:
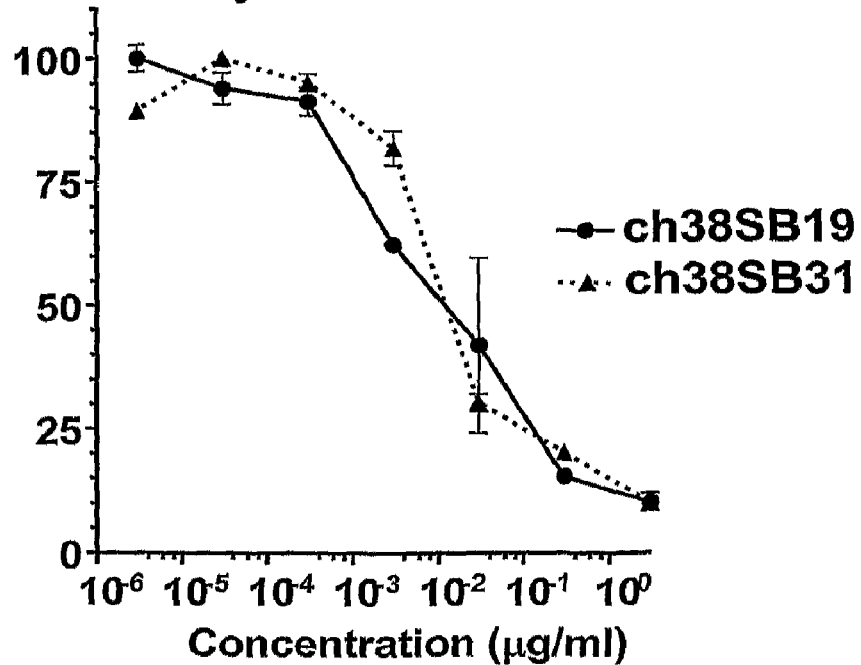
Figure 10:
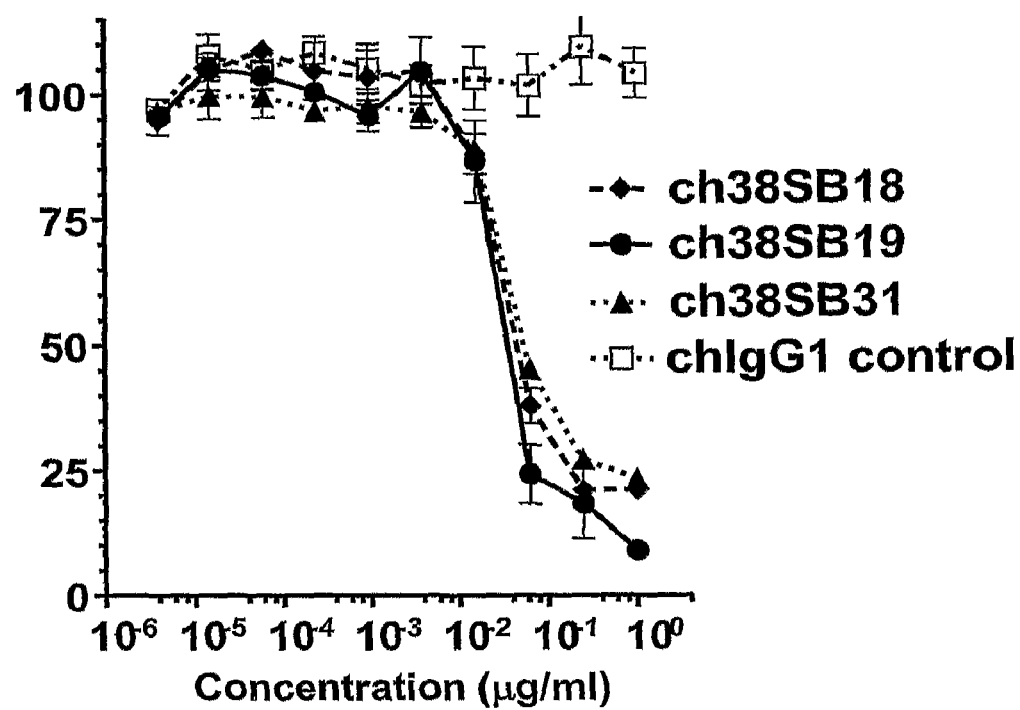
FIG. 10 shows CDC activities mediated by the antibodies ch38SB18, ch38SB19, ch38SB31, and by non-binding chimeric human IgG1 control antibody towards LP-1 multiple myeloma cells.
Figure 11A:
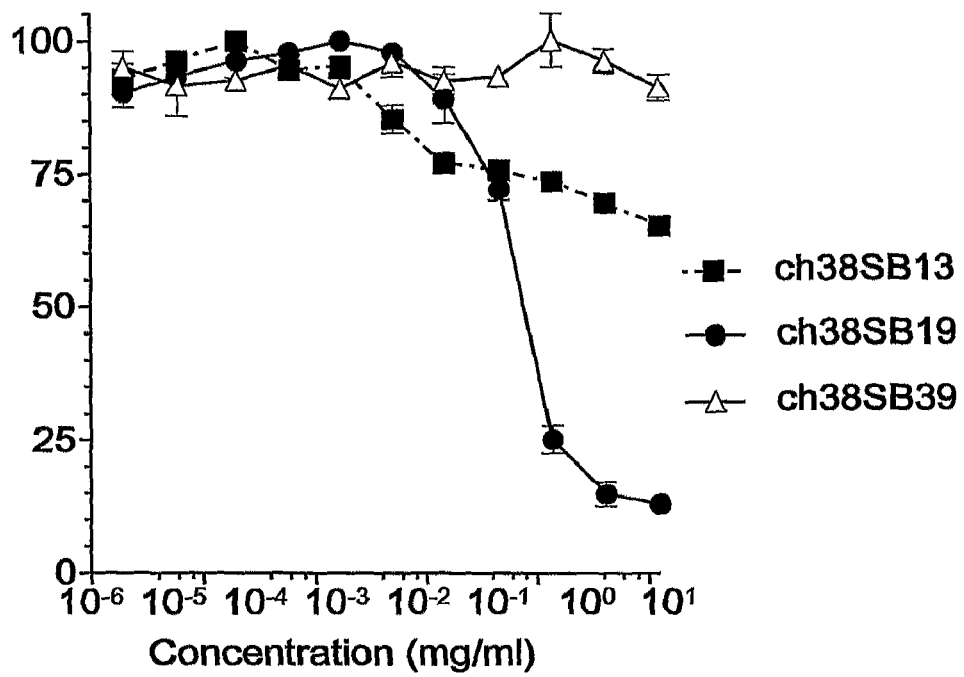
FIG. 11A shows CDC activities mediated by the antibodies ch38SB13, cch38SB19, and ch38SB39 towards Daudi cells.
Figure 11B:
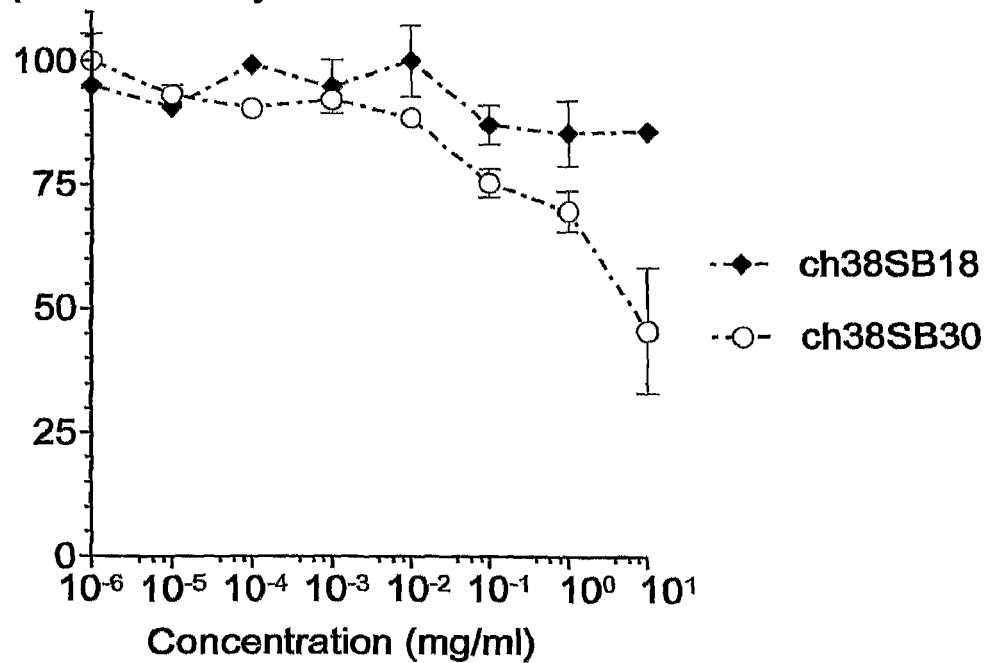
FIG. 11B shows CDC activities mediated by the antibodies ch38SB18 and ch38SB30 towards Daudi cells.
Figure 11C:
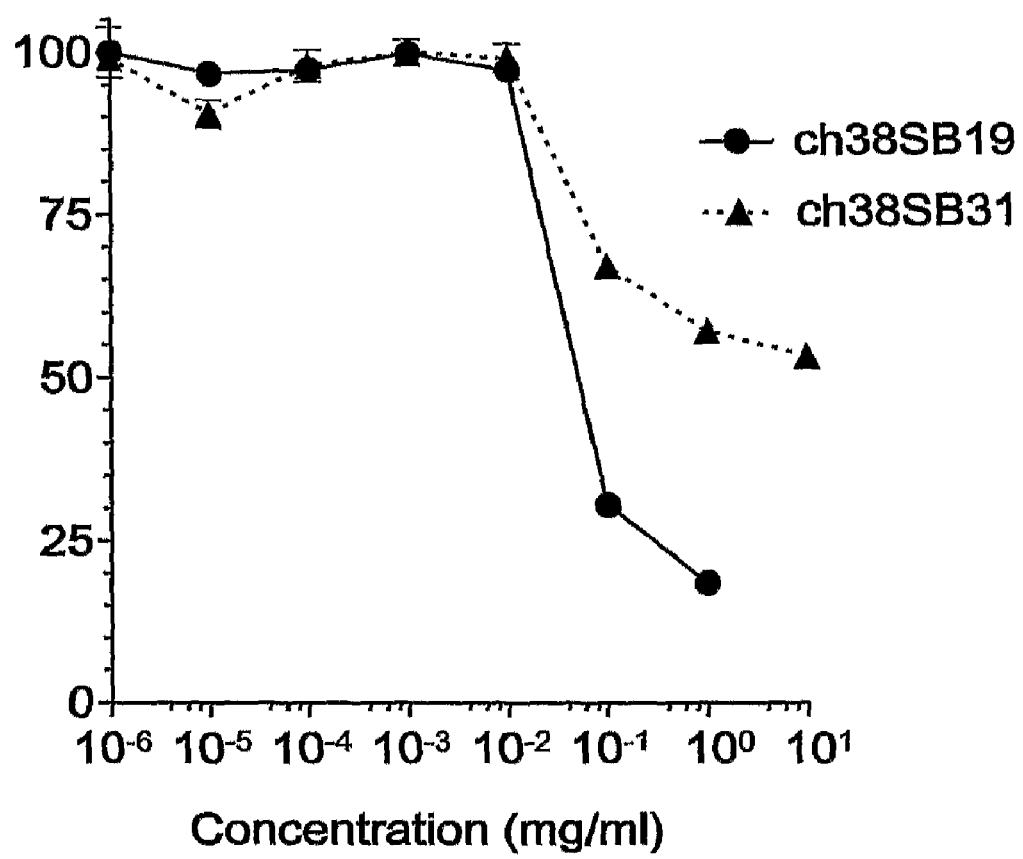
FIG. 11C shows CDC activities mediated by the antibodies ch38SB19 and ch38SB31 towards Daudi cells

When the CDC activities of the chimeric anti-CD38 antibody samples were tested with Raji-IMG cells using human complement at a final dilution of 5%, chimeric anti-CD38 antibodies showed very potent CDC activities (FIG. 9). Raji-IMG are cells derived from Raji cells (ATCC CCL-86) and express lower levels of the membrane complement inhibitors CD55 and CD59. The $EC_{50}$ values were estimated by non-linear regression from the sigmoidal dose response curve shown in FIG. 8. and are as follows: 0.005 µg/mL for ch38SB13, 0.0101 µg/mL for ch38SB18, 0.028 µg/mL for ch38SB19, 0.020 µg/mL for ch38SB30, 0.010 µg/mL for ch38SB31, and 0.400 µg/mL for ch38SB39. Chimeric anti-CD38 antibodies also showed potent CDC activity towards LP-1 multiple myeloma cells ($EC_{50}$ value: 0.032 µg/mL for ch38SB18; 0.030 µg/mL for ch38SB19; 0.043 µg/mL for ch38SB31), while a non-binding chimeric control IgG1 (rituximab, Biogenidec) did not have any CDC activity (FIG. 10). When chimeric CD38 antibodies were tested on Daudi lymphoma cells, different anti-CD38 antibodies differed in their CDC activities (FIG. 11). While the specific viability of Daudi cells was less than 15% following their incubation with 1.25 µg/mL of ch38SB19 in the presence of complement, there was only a marginal decrease in the specific viability of these cells following their incubation with ch38SB18 or ch38SB39 (1.25 µg/mL or higher concentration) in the presence of complement (the specific viability was 85% and 91%, respectively). Also, only a modest reduction of specific viability was observed when the Daudi cells were incubated with 1.25 µg/mL or higher concentration of ch38SB13, ch38SB30, and ch38SB31 in the presence of complement (the specific viability was 65%, 45%, and 53%, respectively).

Example 8

Figure 12A:
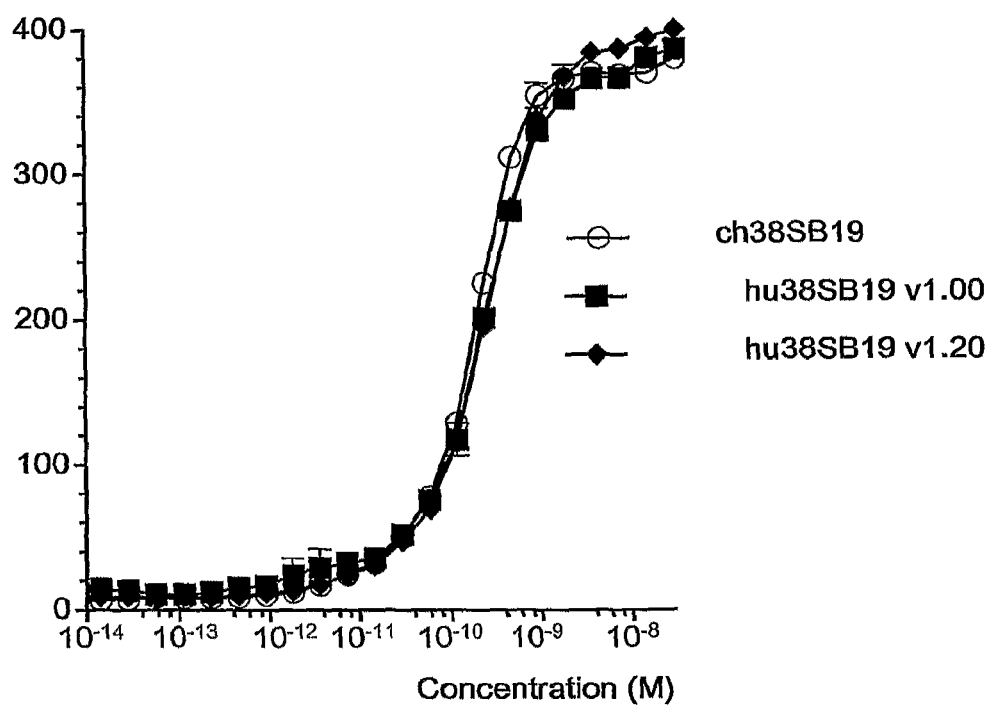
FIG. 12A shows the binding titration curves of ch38SB19, hu38SB19 v1.00, and hu38SB19 v1.20 for binding to Ramos cells.
Figure 12B:
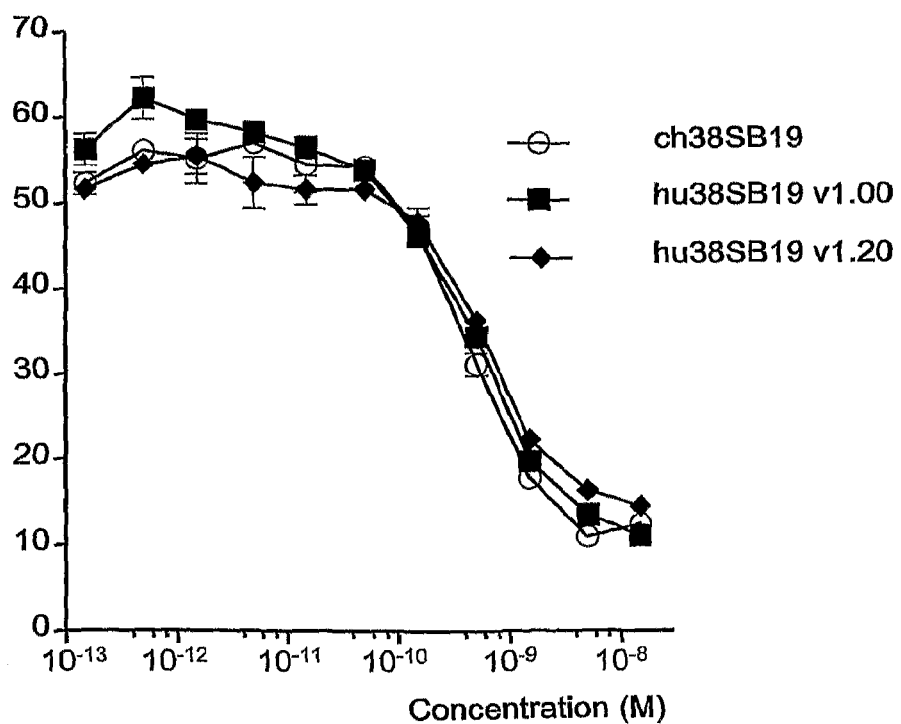
FIG. 12B shows the binding curves that compare ch38SB19, hu38SB19 v1.00, and hu38SB19 v1.00 for their ability to compete with binding of biotinylated murine 38SB19 antibody to Ramos cells.
Figure 13:
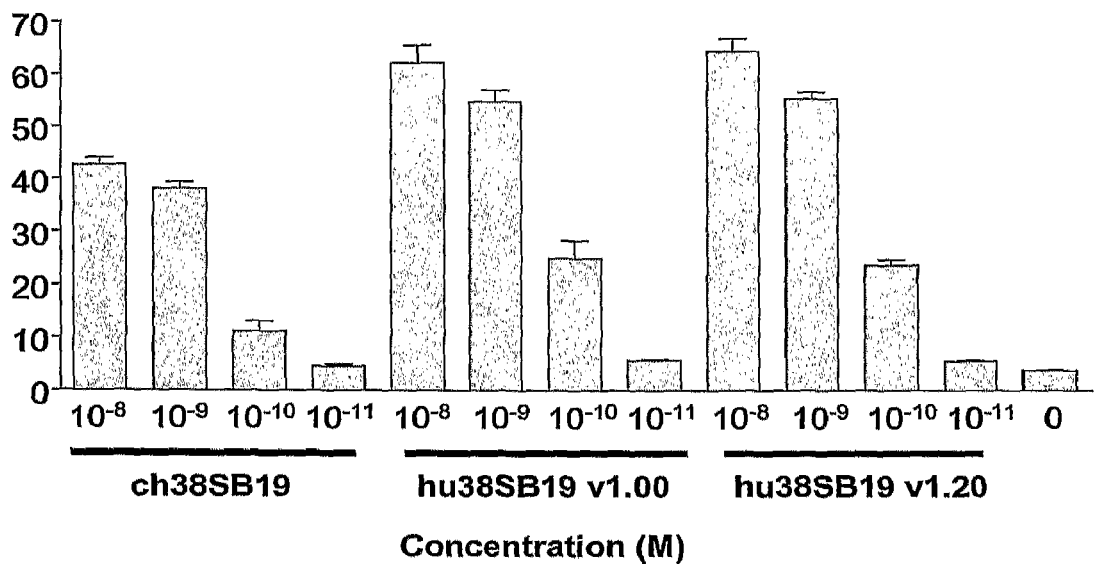
FIG. 13 shows the average percentages of Daudi cells undergoing apoptosis after 24 h of incubation with ch38SB19, hu38SB19 v1.00, or hu38SB19 v1.20 antibody.
Figure 14:
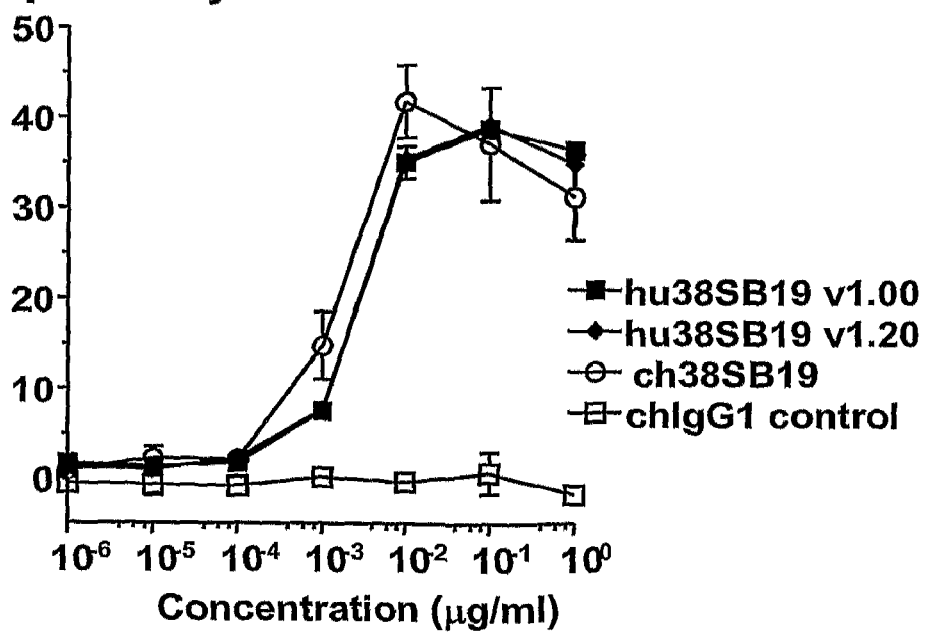
FIG. 14 shows ADCC activities mediated by the antibodies ch38SB19, hu38SB19 v1.00, hu38SB19 v1.20, and by non-binding chimeric human IgG1 control antibody towards LP-1 multiple myeloma cells.
Figure 15A:
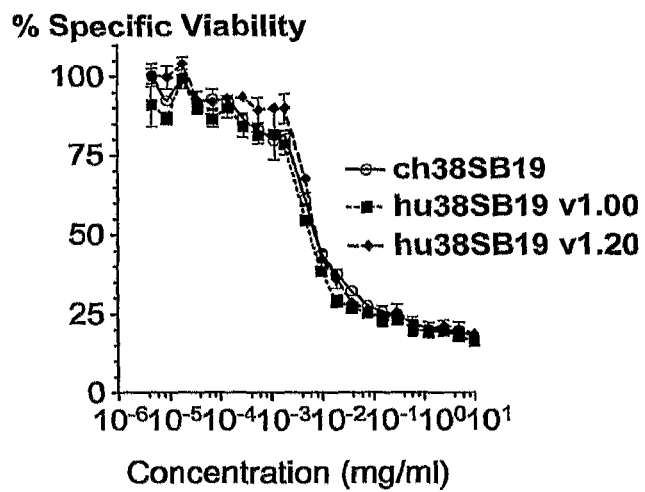
FIG. 15A shows CDC activities mediated by antibodies ch38SB19, hu38SB19 v1.00, and hu38SB19 v1.20 towards Raji-IMG lymphoma cells.
Figure 15B:
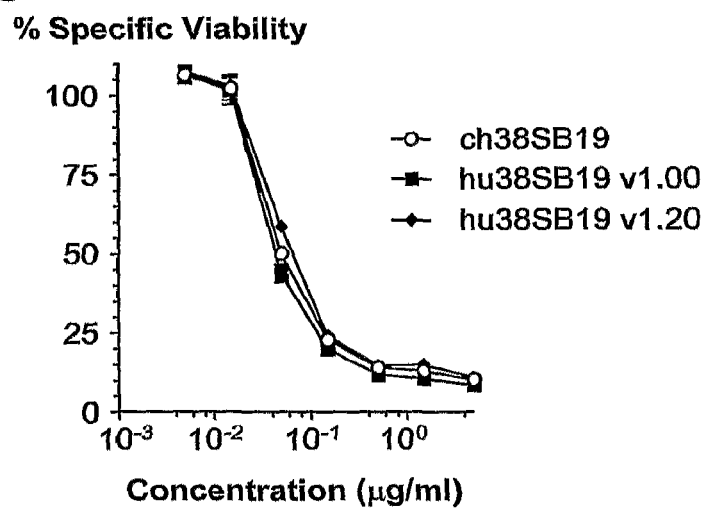
FIG. 15B shows CDC activities mediated by antibodies ch38SB19, hu38SB19 v1.00, and hu38SB19 v1.20 towards LP-1 multiple myeloma cells.
Figure 15C:
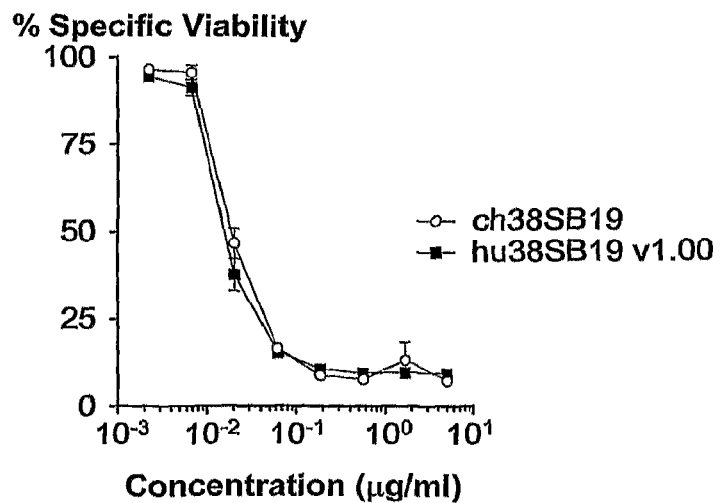
FIG. 15C shows CDC activities mediated by antibodies ch38SB19, hu38SB19 v1.00, and hu38SB19 v1.20 towards DND-41 T-cell acute lymphoblastic leukemia cells.
Figure 16:
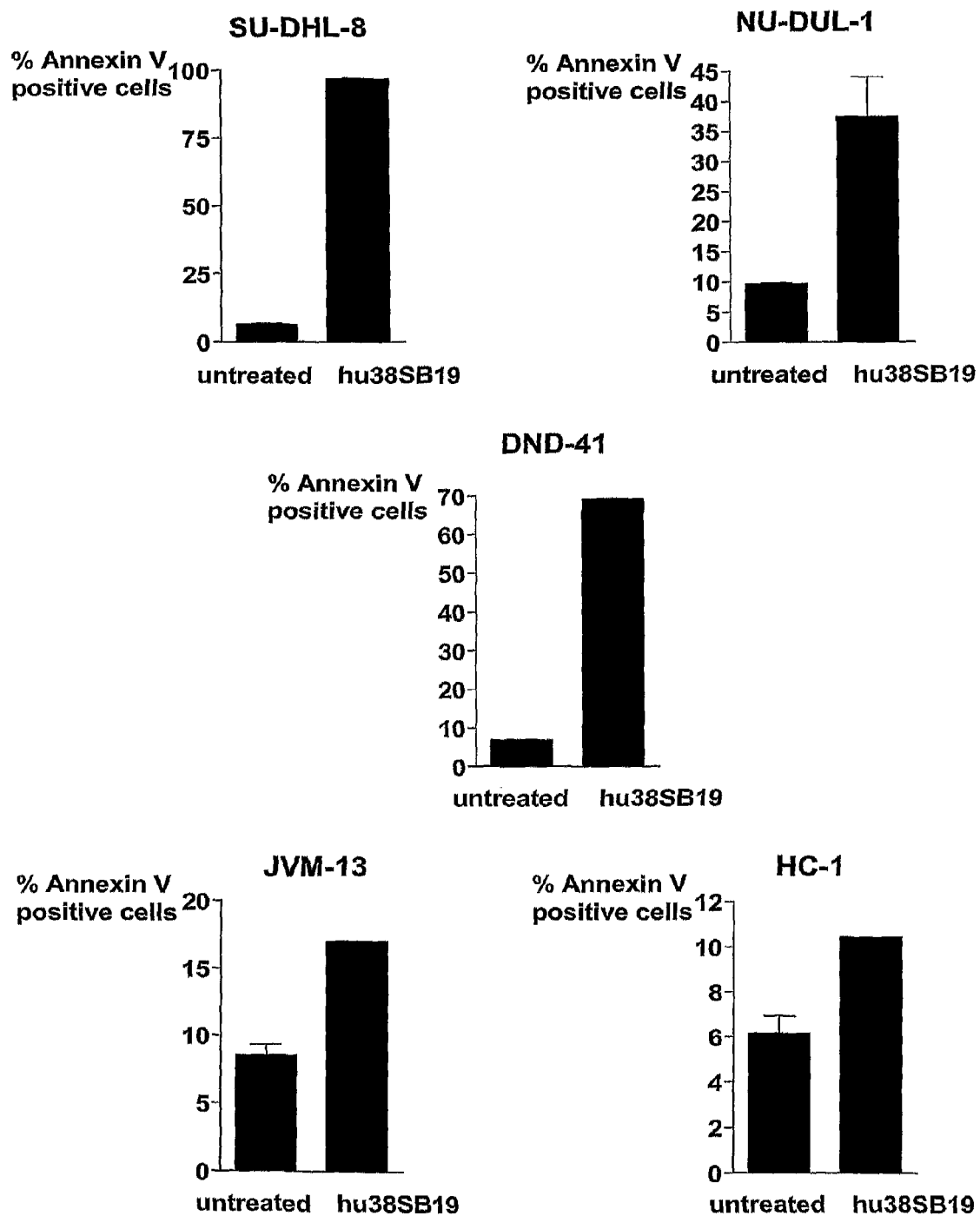
FIG. 16 shows the average percentages of Annexin V positive cells after 24 h of incubation with hu38SB19 v1.00 antibody for SU-DHL-8 diffuse large B cell lymphoma cells, NU-DUL-1 B-cell lymphoma cells, DND-41 T-cell acute lymphoblastic leukemia cells, JVM-13 B-cell chronic lymphocytic leukemia cells and HC-1 hairy cell leukemia cells.

Binding Affinity and Apoptotic, ADCC, and CDC Activities of Humanized Anti-CD38 Antibodies The two versions of humanized 38SB19 (hu38SB19 v1.00 and v1.20) and the chimeric 38SB19 showed similar binding affinities when tested with Ramos cells with $K_D$ values of 0.23 nM, 0.25 nM, and 0.18 nM, respectively (FIG. 12A). The binding affinities of chimeric and humanized 38SB19 antibodies were also compared in a competiton binding assay, where their ability to compete with the binding of biotinylated murine 38SB19 antibody is measured. Biotin-labeled murine 38SB19 antibody ($3\times10^{-10}$ M) was mixed with various concentrations of ch38SB19, hu38SB19 v1.00, or hu38SB19 v1.20. The antibody mixture was incubated with Ramos cells, and the amount of the biotinylated murine 38SB19 bound to the cells was measured with FITC-conjugated streptavidin by FACS analysis. Hu38SB19 v1.00, hu38SB19 v1.20, and ch38SB19 competed with the binding of biotinylated murine 38SB19 equally well (FIG. 12B), again indicating that the binding affinity was unaffected by the humanization. When ch38SB19, hu38SB19 v1.00 and hu38SB19 v1.20 ($10^{-8}$ to $10^{-11}$ M) were compared for their ability to induce apoptosis of Daudi cells, they showed similar apoptotic activities (FIG. 13). Moreover, hu38SB19 v1.00 and v1.20 also showed similar ADCC as ch38SB19 in LP-1 cells (FIG. 14) and similar CDC potencies as ch38SB19 in Raji-IMG and LP-1 cells (FIG. 15). Hu38SB19 v1.00 also showed similar CDC activity as ch38SB19 in the T-cell acute lymphoblastic leukemia cell line DND-41 (DSMZ 525) (FIG. 15). Hu38SB19 v1.00 was further tested for its ability to induce apoptosis in a diverse set of cell lines (FIG. 16). Treatment with hu38SB19 v1.00 ($10^{-8}$ M) resulted in a dramatic increase of Annexin V-positive cells in the B cell lymphoma cell lines SU-DHL-8 (DSMZ ACC 573) (from 7% in untreated control to 97% in hu38SB19-treated cells) and NU-DUL-1 (DSMZ ACC 579) (from 10% in untreated control to 37% in hu38SB19-treated cells) and the T-ALL cell line DND-41 (from 7% in untreated control to 69% in hu38SB19-treated cells). In addition, treatment with hu38SB19 v1.00 ($10^{-8}$ M) increased the portion of Annexin V-positive cells in the B-cell lymphocytic leukemia cell line JVM-13 (DSMZ ACC 19) (from 8% in untreated control to 17% in hu38SB19-treated cells) and in the hairy cell leukemia cell line HC-1 (DSMZ ACC 301) (from 6% in untreated control to 10% in hu38SB19-treated cells).

Similarly, two versions of humanized 38SB31 (hu38SB31 v1.1 and v1.2) and the chimeric 38SB31 showed similar binding affinities when tested with Ramos cells with $K_D$ values of 0.13 nM, 0.11 nM, and 0.12 nM, respectively. The binding affinities of chimeric and humanized 38SB31 antibodies were also compared in a competition binding assay, as described above and performed equally well. Hu38SB31v1.1 was further tested for its ability to induce apoptosis in several cell lines. The humanized antibody showed similar apoptotic activities as ch38SB31 towards Ramos, Daudi, Molp-8 and SU-DHL-8 cells. Moreover, hu38SB31 v1.1 also showed similar ADCC and CDC activities as ch38SB31 in these cell lines.

Example 9

In Vivo Efficacy of 38SB13, 38SB18, 38SB19, 38SB30, 38SB31, and 38SB39

Figure 17:
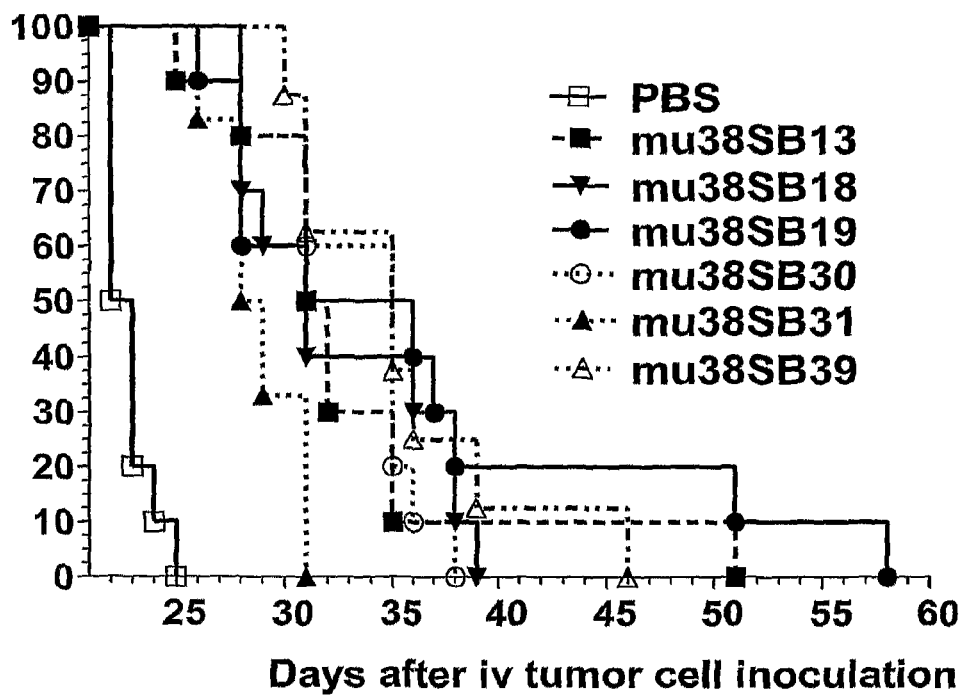
FIG. 17 shows the percent survival of SCID mice bearing established disseminated human Ramos tumors. Mice were treated with murine 38SB13, 38SB18, 38SB19, 38SB30, 38SB31, or 38SB39 antibody or PBS as indicated.

In vivo anti-tumor activities of 38SB13, 38SB18, 38SB19, 38SB30, 38SB31, and 38SB39 were investigated in a survival human xenograft tumor model in immunodeficient mice (female CB.17 SCID) established with Ramos lymphoma cells. Female CB.17 SCID mice were inoculated with $2\times10^6$ Ramos cells in 0.1 mL serum-free medium through a lateral tail vein. Seven days after tumor cell inoculation, mice were randomized into seven groups based on body weight. There were 10 mice per group, except for the 38SB31-treated group, which had 6 mice, and the 38SB39-treated group, which had 8 mice. Antibodies were given to mice intravenously at a dose of 40 mg/kg, twice per week, in three successive weeks, starting seven days after cell inoculation. Mice were sacrificed if one or both hind legs were paralyzed, the loss of body weight was more than 20% from the pre-treatment value, or the animal was too sick to reach food and water. The treatment with 38SB13, 38SB18, 38SB19, 38SB30, 38SB31, or 38SB39 significantly extended the survival of mice compared to that of PBS-treated mice (FIG. 17). The median survival of PBS-treated mice was 22 days and that of antibody-treated groups ranged from 28 to 33 days.

Figure 18:
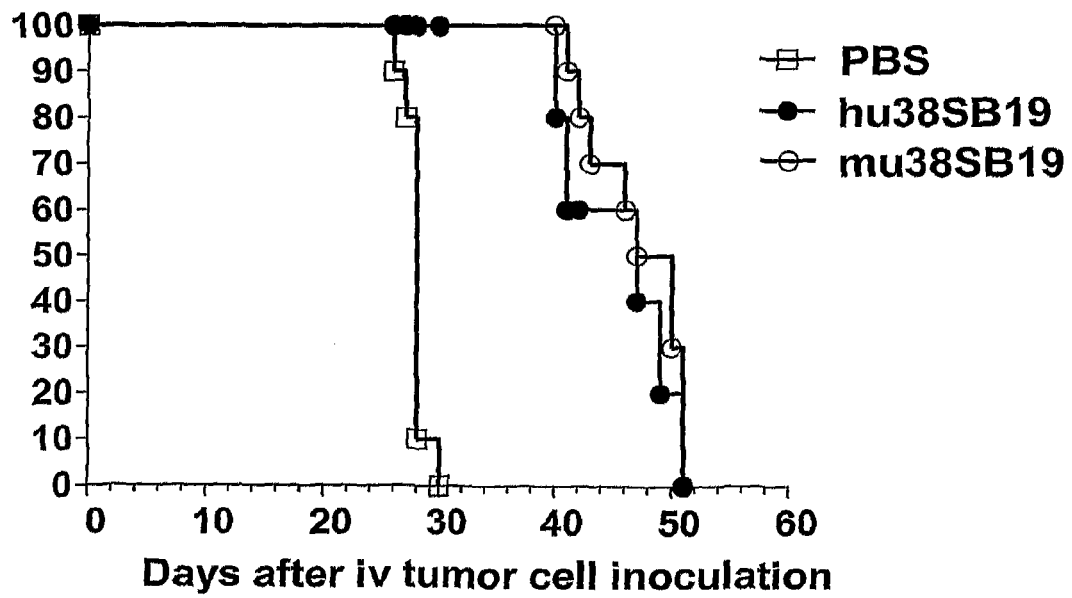
FIG. 18 shows the percent survival of SCID mice bearing established disseminated human Daudi tumors. Mice were treated with hu38SB19 or mu38SB19 antibody or PBS as indicated.

In vivo anti-tumor activities of mu38SB19 and hu38SB19 were further investigated in additional human xenograft tumor models in immunodeficient mice. For a Daudi lymphoma survival model, SCID mice were inoculated with $5\times10^6$ Daudi cells in 0.1 mL serum-free medium through a lateral tail vein. The study was carried out as described above. The treatment with either mu38SB19 or hu38SB19 significantly extended the survival of mice compared to that of PBS-treated mice (FIG. 18). The median survival of PBS-treated mice was 22 days, while the median survival of antibody-treated mice was 47 days.

Figure 19:
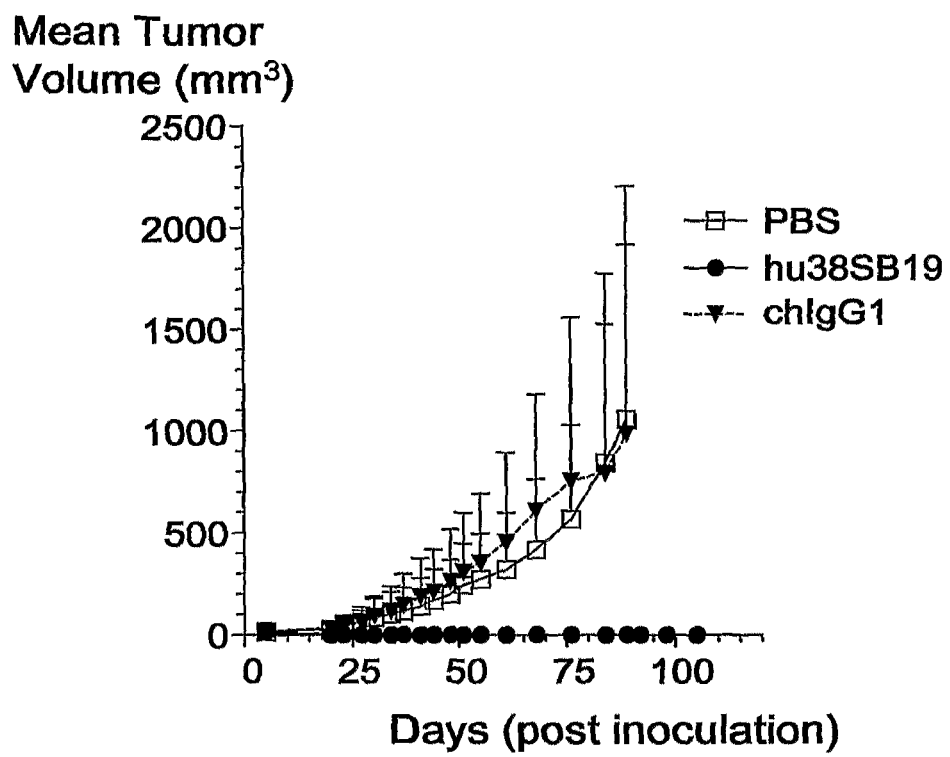
FIG. 19 shows the mean tumor volume of SCID mice bearing NCI-H929 multiple myeloma xenograft tumors. Mice were treated with hu38SB19, a non-binding control IgG1 antibody or PBS as indicated.

For a NCI-H929 multiple myeloma tumor model, SCID mice were inoculated subcutaneously with $10^7$ cells. When tumors were palpable on day 6, the animals were randomized into groups of 10 according to body weight and antibody treatment was started. The hu38SB19 antibody or a non-binding chimeric IgG1 control antibody (rituximab, Biogenidec) were given to mice intravenously at a dose of 40 mg/kg, twice per week, in three successive weeks. Tumor volume was monitored and animals were sacrificed if tumors reached 2000 mm³ in size or became necrotic. The PBS treated group reached a mean tumor volume of 1000 mmm³ on day 89, the chimeric IgG1 control antibody group on day 84 (FIG. 19). Treatment with hu38SB19 completely prevented tumor growth in all 10 animals. In contrast, only two animals in the PBS treated group and three animals in the chimeric IgG1 control antibody showed tumor regression.

Figure 20:
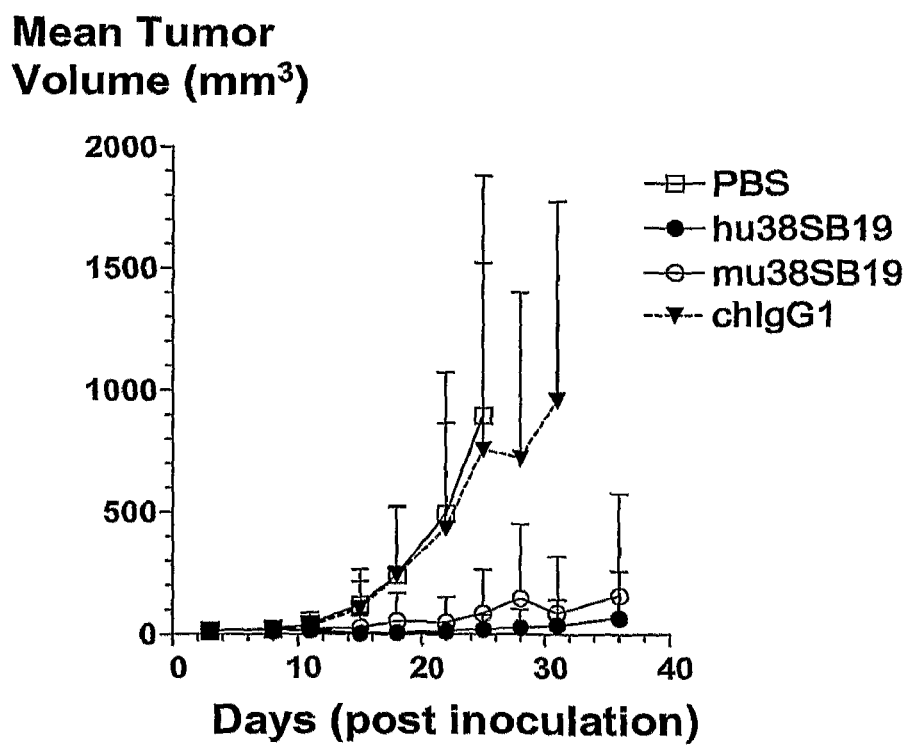
FIG. 20 shows the mean tumor volume of SCID mice bearing MOLP-8 multiple myeloma xenograft tumors. Mice were treated with hu38SB19, mu38SB19, a non-binding control IgG1 antibody or PBS as indicated.

For a MOLP-8 multiple myeloma tumor model, SCID mice were inoculated subcutaneously with $10^7$ cells. When tumors were palpable on day 4, the animals were randomized into groups of 10 according to body weight and antibody treatment was started. The hu38SB19 and mu38SB19 antibodies or a chimeric IgG1 control antibody were given to mice intravenously at a dose of 40 mg/kg, twice per week, in three successive weeks. Tumor volume was monitored and animals were sacrificed if tumors reached 2000 mm³ in size or became necrotic. The PBS treated group reached a mean tumor volume of 500 mmm³ on day 22, the chimeric IgG1 control antibody group on day 23 (FIG. 20). None of the tumors in these groups regressed. In contrast, treatment with hu38SB19 or mu38SB19 led to tumor regression in 8 of 10 or 6 of 10 animals, respectively.

Tables

TABLE 1A

The mu38SB19 light chain framework surface residues and corresponding residues at the same Kabat position in the human 1.69 antibody. The residues that are different and therefore changed in the hu38SB19 antibody are in grayed boxes. The starred (*) residues are back mutated to the mu38SB19 residue in one or more hu38SB19 variants.

| Kabat Position | mu38SB19 | 1.69 |
|---|---|---|
| 1 | D | D |
| 3 | V | V |
| 5* | T | A |
| 9 | L | K |
| 10 | S | F |
| 15 | L | V |
| 18 | P | R |
| 40 | P | P |
| 41 | G | G |
| 42 | Q | Q |
| 45 | R | K |
| 57 | G | G |
| 60 | D | D |
| 67 | A | S |
| 80 | A | A |
| 81 | E | E |
| 107 | K | K |
| 108 | R | R |

TABLE 1B

The mu38SB19 heavy chain framework surface residues and corresponding residues at the same Kabat position in the human 1.69 antibody. The residues that are different and therefore changed in the hu38SB19 antibody are in grayed boxes.

| Kabat Position | mu38SB19 | 1.69 |
|---|---|---|
| 1 | Q | Q |
| 3 | Q | Q |
| 5 | V | Q |
| 9 | A | A |
| 11 | V | L |
| 13 | K | R |
| 14 | P | P |
| 19 | K | K |
| 23 | K | K |
| 28 | T | T |
| 41 | P | P |
| 42 | G | G |
| 43 | Q | Q |
| 61 | Q | Q |
| 62 | K | K |
| 64 | Q | K |
| 65 | G | G |
| 73 | K | K |
| 74 | S | S |
| 82B | S | S |
| 84 | S | S |
| 85 | E | E |
| 106 | Q | Q |
| 113 | S | S |

TABLE 2

Primers used for the degenerate PCR reactions are based on those in Wang et al, 2000 except HindKL which is based on Co et el. 1992. Mixed bases are defined as follows: H = A + T + C, S = g + C, Y = C + T, K = G + T, M = A + C, R = A + g, W = A + T, V = A + C + G.

| Primer | Sequence |
|---|---|
| BamIgG1 (SEQ ID NO. 73) | GGAGGATCCATAGACAGATGGGGGTGTCGTTTTGGC |
| IgG2Abam (SEQ iD NO. 74) | GGAGGATCCCTTGACCAGGCATCCTAGAGTCA |
| EcoMH1 (SEQ ID NO. 75) | CTTCCGGAATTCSARGTNMAGCTGSAGSAGTC |
| EcoMH2 (SEQ ID NO. 76) | CTTCCGGAATTCSARGTNMAGCTGSAGSAGTCWGG |
| SacIMK (SEQ ID NO. 77) | GGAGCTCGAYATTGTGMTSACMCARWCTMCA |
| HindKL (SEQ ID NO. 78) | TATAGAGCTCAAGCTTGGATGGTGGGAAGATGGATACAGTTGGTGC |

TABLE 3

The light and heavy chain PCR reaction mixes for cloning of the 38SB19 variable region cDNA sequences.

| Light Chain Reaction Mix | |
|---|---|
| 5 μl | 10 × PCR reaction buffer (Roche) |
| 4 μl | 10 mM dNTP mix (2.5 mM each) |
| 2 μl | Template (RT reaction) |
| 5 μl | 10 μM SacIMK left primer |
| 5 μl | 10 μM HindKL right primer |
| 5 μl | DMSO |
| 0.5 μl | Taq Polymerase (Roche) |
| 23.5 μl | sterile distilled H₂O |
| 50 μl | Total |
| Heavy Chain Reaction Mix | |
| 5 μl | 10 × PCR reaction buffer (Roche) |
| 4 μl | 10 mM dNTP mix (2.5 mM each) |
| 2 μl | Template (RT reaction) |
| 2.5 μl | 10 μM EcoMH1 left primer |
| 2.5 μl | 10 μM EcoMH2 left primer |
| 5 μl | 10 μM BamIgG1 right primer |
| 5 μl | DMSO |
| 0.5 μl | Taq Polymerase (Roche) |
| 23.5 μl | sterile distilled H₂O |
| 50 μl | Total |

TABLE 4

The 5' end murine leader sequence primers used for the 38SB19 second round PCR reactions. The 3' end primers are identical to those used in the first round reactions since they prime to the respective constant region sequences.

| Primer | Sequence |
|---|---|
| Light Chain 38SB19 LC Leader (SEQ ID NO. 79) | ATGGAGTCACAGATTCAGGTC |
| Heavy Chain 38-19HCLead1 (SEQ ID NO. 80) | TTTTGAATTCCAGTAACTTCAGGTGTCCACTC |

TABLE 5 cDNA calculated and LC/MS measured molecular weights of the murine 38SB19 antibody light and heavy chains.

| | Light Chain | | | Heavy Chain | | |
|---|---|---|---|---|---|---|
| | cDNA | LC/MS | Difference | cDNA | LC/MS | Difference |
| Mu38SB19 | 23735 | 23736 | 1 | 48805 | 48826 | 21 |

The invention claimed is:

1. An isolated antibody or epitope-binding fragment thereof comprising CDRs identified in SEQ ID NOS: 13, 15, 16, 17, 18 and 81, wherein said antibody or fragment is capable of specifically binding CD38.

2. An antibody or epitope-binding fragment thereof according to claim 1, characterized in that said antibody or epitope-binding fragment thereof characterized in that said antibody or epitope-binding fragment thereof is capable of killing a CD38+ cell by apoptosis, antibody-dependent cell-mediated cytotoxicity (ADCC), and complement-dependent cytoxicity (CDC) wherein killing said CD38+ cell by apoptosis can occur in the absence of stroma cells or stroma-derived cytokines.

3. An antibody or epitope-binding fragment thereof according to claim 1, characterized in that said antibody or epitope-binding fragment thereof is a monoclonal antibody.

4. An antibody or epitope-binding fragment thereof according to claim 2, characterized in that said CD38+ cell is a lymphoma cell, a leukemia cell, or a multiple myeloma cell.

5. The antibody or epitope-binding fragment thereof of claim 2, characterized in that said CD38+ cell is a non-Hodgkin's lymphoma (NHL) cell, a Burkitt's lymphoma (BL) cell, a multiple myeloma (MM) cell, a B chronic lymphocytic leukemia (B-CLL) cell, a B and T acute lymphocytic leukemia (ALL) cell, a T cell lymphoma (TCL) cell, an acute myeloid leukemia (AML) cell, a hairy cell leukemia (HCL) cell, a Hodgkin's Lymphoma (HL) cell, or a chronic myeloid leukemia (CML) cell.

6. An antibody or epitope-binding fragment thereof according to claim 1, characterized in that said antibody or epitope-binding fragment thereof binds CD38 with a $k_D$ of $3 \times 10^{-9}$ M or lower.

7. An antibody or epitope-binding fragment thereof according to claim 1, characterized in that said antibody or epitope-binding fragment thereof is produced by a hybridoma cell line deposited at the American Type Culture Collection (10801 University Bld, Manassas, Va., 20110-2209, USA), on Jun. 21, 2006, under the deposit number PTA-7670.

8. An antibody or epitope-binding fragment thereof according to claim 1, characterized in that said antibody or epitope-binding fragment thereof comprises at least one human constant region.

9. An antibody or epitope-binding fragment thereof according to claim 8, characterized in that said constant region is the human IgG1/IgKappa constant region.

10. An antibody or epitope-binding fragment thereof according to claim 1, characterized in that said antibody is a humanized or resurfaced antibody.

11. A humanized or resurfaced antibody or epitope-binding fragment thereof according to claim 10, characterized in that said humanized or resurfaced antibody or epitope-binding fragment thereof comprises at least one heavy chain and at least one light chain, wherein said heavy chain comprises three sequential complementarity-determining regions having amino acid sequences represented by SEQ ID NOS: 13, 81, and 15, and wherein said light chain comprises three sequential complementarity-determining regions having amino acid sequences represented by SEQ ID NOS: 16, 17, and 18.

12. A humanized or resurfaced antibody or epitope-binding fragment thereof according to claim 11, characterized in that said humanized or resurfaced antibody or epitope-binding fragment thereof comprises a heavy chain variable region having an amino acid sequence represented by SEQ ID NO: 66.

13. A humanized or resurfaced antibody or epitope-binding fragment thereof according to claim 11, characterized in that said humanized or resurfaced antibody or epitope-binding fragment thereof comprises a light chain variable region having an amino acid sequence selected from the group of SEQ ID NOS: 62 and 64.

14. An antibody or epitope-binding fragment thereof according to claim 1, characterized in that said antibody or epitope-binding fragment thereof is a Fab, Fab', F(ab')2 or Fv fragment.

15. A conjugate comprising the antibody or epitope-binding fragment thereof according to claim 1 linked to a cytotoxic agent.

16. The conjugate of claim 15, characterized in that said cytotoxic agent is selected from the group consisting of a maytansinoid, a small drug, a tomaymycin derivative, a leptomycin derivative, a prodrug, a taxoid, CC-1065 and a CC-1065 analog.

17. The conjugate of claim 15, characterized in that said cytotoxic agent is the maytansine DM1 of formula:

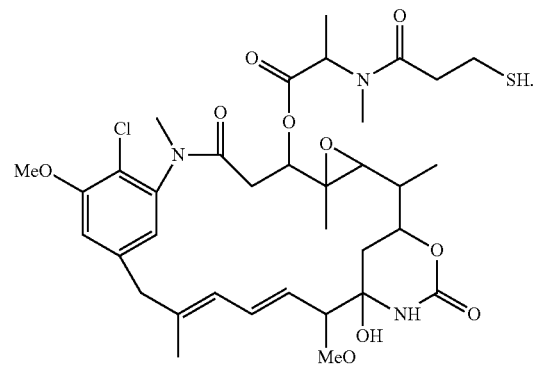

18. The conjugate of claim 15, characterized in that said cytotoxic agent is the maytansine DM4 of formula:

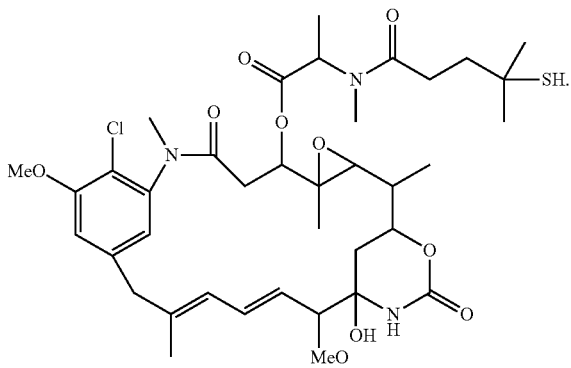

19. The conjugate of claim 15, characterized in that said cytotoxic agent is a tomaymycin derivative selected from the group consisting of:

8,8'-[1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-methoxy-1,3-benzenediylbis(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[1,4-butanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[3-methyl-1,5-pentanediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[2,6-pyridinediylbis(oxy)]-bis[(S)-2-eth-(E)-ylidene-7-methoxy-1,2,3,11a-tetrahydro-5H-pyrrolo[2,1-c][1,4]benzodiazepin-5-one]

8,8'-[4-(3-tert-butoxycarbonylaminopropyloxy)-2,6-pyridinediylbis-(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-[5-(3-aminopropyloxy)-1,3-benzenediylbis(methyleneoxy)]-bis[(S)-2-eth-(E)-ylidene- 8,8'-[5-(N-methyl-3-tert-butoxycarbonylaminopropyl)-1,3-benzenediylbis-(methyleneoxy)]-bis[(S)-2-eth-(E)-ylidene-7-methoxy-1,2,3,11a-tetrahydro-5H-pyrrolo[2,1-c][1,4]benzodiazepin-5-one]

8,8'-{5-[3-(4-methyl-4-methyldisulfanyl-pentanoylamino)propyloxy]-1,3-benzenediylbis(methyleneoxy)}-bis[(S)-2-eth-(E)-ylidene-7-methoxy-1,2,3,11a-tetrahydro-5H-pyrrolo[2,1-c][1,4]benzodiazepin-5-one]

8,8'-[5-acetylthiomethyl-1,3-benzenediylbis(methyleneoxy)]-bis[(S)-2-methylene-7-methoxy-1,2,3,11a-tetrahydro-5H-pyrrolo[2,1-c][1,4]benzodiazepin-5-one]

bis-{2-[(S)-2-methylene-7-methoxy-5-oxo-1,3,11a-tetrahydro-5H-pyrrolo[2,1-c][1,4]benzodiazepin-8-yloxy]ethyl}-carbamic acid tert-butyl ester 8,8'-[3-(2-acetylthioethyl)-1,5-pentanediylbis(oxy)]-bis[(S)-2-methylene-7-methoxy-1,2,3,11a-tetrahydro-5H-pyrrolo[2,1-c][1,4]benzodiazepin-5-one]

8,8'-[5-(N-4-mercapto-4,4-dimethylbutanoyl)amino-1,3-benzenediylbis(methyleneoxy)]-bis[7-methoxy-2-methylene-1,2,3,11a-tetrahydro-5H-pyrrolo[2,1-c][1,4]benzodiazepin-5-one]

8,8'-[5-(N-4-methyldithio-4,4-dimethylbutanoyl)-amino-1,3-benzenediylbis(methyleneoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-mercapto-2,2-dimethylethyl)amino-1,3-benzenediyl(methyleneoxy)]-bis[7-methoxy-2-methylene-1,2,3,11a-tetrahydro-5H-pyrrolo[2,1-c][1,4]benzodiazepin-5-one]

8,8'-[5-(N-methyl-N-(2-methyldithio-2,2-dimethylethypamino-1,3-benzenediyl(methyleneoxy)]-bis[7-methoxy-2-methylene-1,2,3,11a-tetrahydro-5H-pyrrolo[2,1-c][1,4]benzodiazepin-5-one]

8,8'-[(4-(2-(4-mercapto-4-methyl)-pentanamido-ethoxy)-pyridin-2,6-dimethyl)-dioxy]-bis[(S)-2-eth-(E)-ylidene-7-dimethoxy-1,2,3,11a-tetrahydro-pyrrolo[2,1-

8,8'-[(1-(2-(4-methyl-4-methyldisulfanyl)-pentanamido-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-(4-methyl-4-methyldisulfanyl)-pentanamidopropoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(4-(4-methyl-4-methyldisulfanyl)-pentanamidobutoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-(4-methyl-4-methyldisulfanyl-pentanoyl)-piperazin-1-yl]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(3-[4-(4-methyl-4-methyldisulfanyl-pentanoyl)-piperazin-1-yl]-propyl)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(4-methyl-4-methyldisulfanyl-pentanoylamino)-ethoxy]ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{2-[2-(2-{2[2-(4-methyl-4-methyldisulfanyl-pentanoylamino)-ethoxy]-ethoxy}-ethoxy)-ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-{-2[2-(4-methyl-4-methyldisulfanyl-pentanoylamino)-ethoxy]ethoxy}-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(2-{2-[2-(2-{2-[2(4-methyl-4-methyldisulfanyl-pentanoylamino)-ethoxy]ethoxy}-ethoxy)-ethoxy]ethoxy}-ethoxy)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(1-(2-[methyl-(2-methyl-2-methyldisulfanyl-propyl)-amino]-ethoxy)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(4-methyl-4-methyldisulfanyl-pentanoyl)-amino]-propyl)-pyridin-2,6-dimethyl)-dioxy]-bis[(S)-2-eth-(E)-ylidene-7-dimethoxy-1,2,3,11a-tetrahydro-pyrrolo[2,1-c][1,4]benzodiazepin-5-one]

8,8'-[(4-(3-[methyl-(2-methyl-2-methyldisulfanyl-propyl)-amino]-propyl)-pyridin-2,6-dimethyl)-dioxy]-bis

[(S)-2-eth-(E)-ylidene-7-dimethoxy-1,2,3,11a-tetrahydro-pyrrolo[2,1-c][1,4]benzodiazepin-5-one]and
8,8'-[(1-(4-methyl-4-methyldisulfanyl)-pentanamido)-benzene-3,5-dimethyl)-dioxy]-bis[(S)-2-eth-(E)-ylidene-7-dimethoxy-1,2,3,11a-tetrahydro-pyrrolo[2,1-c][1,4]benzodiazepin-5-one].

20. The conjugate of claim 15, characterized in that the cytotoxic agent is a leptomycin derivative selected from the group consisting of:
- (2-Methylsulfanyl-ethyl)-amid of (2E,10E,12E,16Z,18E)-(R)-6-Hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid (2-methylsulfanyl-ethyl)-amid
- Bis-[(2-mercaptoethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid]
- (2-Mercapto-ethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid
- (2-Methyldisulfanyl-ethyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid
- (2-Methyl-2-methyldisulfanyl-propyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid and
- (2-Mercapto-2-methyl-propyl)-amid of (2E,10E,12E,16Z,18E)-(R)-6-hydroxy-3,5,7,9,11,15,17-heptamethyl-19-((2S,3S)-3-methyl-6-oxo-3,6-dihydro-2H-pyran-2-yl)-8-oxo-nonadeca-2,10,12,16,18-pentaenoic acid.

21. A pharmaceutical composition containing an antibody or epitope-binding fragment thereof according to claim 1 and a pharmaceutically acceptable carrier or excipients.

22. The pharmaceutical composition of claim 21, characterized in that said composition contains a further therapeutic agent.

23. The pharmaceutical composition of claim 2, characterized in that the further therapeutic agent is selected from the group consisting of an antagonist of epidermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP), vascular endothelial growth factor (VEGF), a receptor for epidermal-growth factor (EGF), a receptor for fibroblast-growth factor (FGF), a receptor for hepatocyte growth factor (HGF), a receptor for tissue factor (TF), a receptor for protein C, a receptor for protein S, a receptor for platelet-derived growth factor (PDGF), a receptor for heregulin, a receptor for macrophage-stimulating protein (MSP), a receptor for vascular endothelial growth factor (VEGF); HER2 receptor, HER3 receptor, c-MET, and other receptor tyrosine kinases.

24. The pharmaceutical composition of claim 22, characterized in that the further therapeutic agent is an antibody directed against a cluster of differentiation antigen selected from a group comprising CD3, CD14, CD19, CD20, CD22, CD25, CD28, CD30, CD33, CD36, CD40, CD44, CD52, CD55, CD59, CD56, CD70, CD79, CD80, CD103, CD134, CD137, CD138, and CD152.

25. An isolated antibody or epitope-binding fragment thereof comprising the CDRs of the monoclonal antibody produced by PTA-7670, wherein said antibody or fragment is capable of specifically binding CD38.

26. An isolated antibody or epitope-binding fragment thereof comprising the CDRs of the humanized monoclonal antibody 38SB19, wherein said antibody or fragment is capable of specifically binding CD38.

27. A pharmaceutical composition containing an antibody or epitope-binding fragment thereof according to claim 15, and a pharmaceutically acceptable carrier or excipients.

28. The pharmaceutical composition of claim 27, characterized in that said composition contains a further therapeutic agent.

29. The pharmaceutical composition of claim 28, characterized in that the further therapeutic agent is selected from the group consisting of an antagonist of epidermal-growth factor (EGF), fibroblast-growth factor (FGF), hepatocyte growth factor (HGF), tissue factor (TF), protein C, protein S, platelet-derived growth factor (PDGF), heregulin, macrophage-stimulating protein (MSP), vascular endothelial growth factor (VEGF), a receptor for epidermal-growth factor (EGF), a receptor for fibroblast-growth factor (FGF), a receptor for hepatocyte growth factor (HGF), a receptor for tissue factor (TF), a receptor for protein C, a receptor for protein S, a receptor for platelet-derived growth factor (PDGF), a receptor for heregulin, a receptor for macrophage-stimulating protein (MSP), a receptor for vascular endothelial growth factor (VEGF); HER2 receptor, HER3 receptor, c-MET, and other receptor tyrosine kinases.

30. The pharmaceutical composition of claim 28, characterized in that the further therapeutic agent is an antibody directed against a cluster of differentiation antigen selected from a group comprising CD3, CD14, CD19, CD20, CD22, CD25, CD28, CD30, CD33, CD36, CD40, CD44, CD52, CD55, CD59, CD56, CD70, CD79, CD80, CD103, CD134, CD137, CD138, and CD152.

* * * * *

SEQUENCE LISTING

<160> NUMBER OF SEQ ID NOS: 81

<210> SEQ ID NO 1
<211> LENGTH: 5
<212> TYPE: PRT
<213> ORGANISM: Mus sp.

<400> SEQUENCE: 1

Ser Tyr Gly Met Asn
1               5

<210> SEQ ID NO 2
<211> LENGTH: 17
<212> TYPE: PRT
<213> ORGANISM: Mus sp.

<400> SEQUENCE: 2

Trp Ile Asn Thr Tyr Thr Gly Glu Pro Thr Tyr Ala Asp Asp Phe Lys

```
1               5                  10                 15
Gly

<210> SEQ ID NO 3
<211> LENGTH: 5
<212> TYPE: PRT
<213> ORGANISM: Mus sp.

<400> SEQUENCE: 3

Arg Gly Phe Ala Tyr
1               5

<210> SEQ ID NO 4
<211> LENGTH: 15
<212> TYPE: PRT
<213> ORGANISM: Mus sp.

<400> SEQUENCE: 4

Arg Ala Ser Glu Ser Val Glu Ile Tyr Gly Asn Gly Phe Met Asn
1               5                  10                 15

<210> SEQ ID NO 5
<211> LENGTH: 7
<212> TYPE: PRT
<213> ORGANISM: Mus sp.

<400> SEQUENCE: 5

Arg Ala Ser Asn Leu Glu Ser
1               5

<210> SEQ ID NO 6
<211> LENGTH: 9
<212> TYPE: PRT
<213> ORGANISM: Mus sp.

<400> SEQUENCE: 6

Gln Gln Ile Asn Glu Asp Pro Phe Thr
1               5

<210> SEQ ID NO 7
<211> LENGTH: 5
<212> TYPE: PRT
<213> ORGANISM: Mus sp.

<400> SEQUENCE: 7

Asn Ser Gly Met Asn
1               5

<210> SEQ ID NO 8
<211> LENGTH: 17
<212> TYPE: PRT
<213> ORGANISM: Mus sp.

<400> SEQUENCE: 8

Trp Ile Asn Thr Tyr Thr Gly Glu Pro Thr Tyr Ala Asp Asp Phe Lys
1               5                  10                 15

Gly

<210> SEQ ID NO 9
<211> LENGTH: 5
<212> TYPE: PRT
<213> ORGANISM: Mus sp.

<400> SEQUENCE: 9
```

```
Arg Gly Phe Val Tyr
1               5

<210> SEQ ID NO 10
<211> LENGTH: 15
<212> TYPE: PRT
<213> ORGANISM: Mus sp.

<400> SEQUENCE: 10

Arg Ala Ser Glu Ser Val Ala Ile Tyr Gly Asn Ser Phe Leu Lys
1               5                   10                  15

<210> SEQ ID NO 11
<211> LENGTH: 7
<212> TYPE: PRT
<213> ORGANISM: Mus sp.

<400> SEQUENCE: 11

Arg Ala Ser Asn Leu Glu Ser
1               5

<210> SEQ ID NO 12
<211> LENGTH: 9
<212> TYPE: PRT
<213> ORGANISM: Mus sp.

<400> SEQUENCE: 12

Gln Gln Ile Asn Glu Asp Pro Tyr Thr
1               5

<210> SEQ ID NO 13
<211> LENGTH: 5
<212> TYPE: PRT
<213> ORGANISM: Mus sp.

<400> SEQUENCE: 13

Asp Tyr Trp Met Gln
1               5

<210> SEQ ID NO 14
<211> LENGTH: 17
<212> TYPE: PRT
<213> ORGANISM: Mus sp.

<400> SEQUENCE: 14

Thr Ile Tyr Pro Gly Asp Gly Asp Thr Gly Tyr Ala Gln Lys Phe Lys
1               5                   10                  15

Gly

<210> SEQ ID NO 15
<211> LENGTH: 11
<212> TYPE: PRT
<213> ORGANISM: Mus sp.

<400> SEQUENCE: 15

Gly Asp Tyr Tyr Gly Ser Asn Ser Leu Asp Tyr
1               5                   10

<210> SEQ ID NO 16
<211> LENGTH: 11
<212> TYPE: PRT
<213> ORGANISM: Mus sp.

<400> SEQUENCE: 16

Lys Ala Ser Gln Asp Val Ser Thr Val Val Ala
```

```
                         1               5                   10

<210> SEQ ID NO 17
<211> LENGTH: 7
<212> TYPE: PRT
<213> ORGANISM: Mus sp.

<400> SEQUENCE: 17

Ser Ala Ser Tyr Arg Tyr Ile
1               5

<210> SEQ ID NO 18
<211> LENGTH: 9
<212> TYPE: PRT
<213> ORGANISM: Mus sp.

<400> SEQUENCE: 18

Gln Gln His Tyr Ser Pro Pro Tyr Thr
1               5

<210> SEQ ID NO 19
<211> LENGTH: 5
<212> TYPE: PRT
<213> ORGANISM: Mus sp.

<400> SEQUENCE: 19

Gly Ser Trp Met Asn
1               5

<210> SEQ ID NO 20
<211> LENGTH: 17
<212> TYPE: PRT
<213> ORGANISM: Mus sp.

<400> SEQUENCE: 20

Arg Ile Tyr Pro Gly Asp Gly Asp Ile Ile Tyr Asn Gly Asn Phe Arg
1               5                   10                  15

Asp

<210> SEQ ID NO 21
<211> LENGTH: 10
<212> TYPE: PRT
<213> ORGANISM: Mus sp.

<400> SEQUENCE: 21

Trp Gly Thr Phe Thr Pro Ser Phe Asp Tyr
1               5                   10

<210> SEQ ID NO 22
<211> LENGTH: 11
<212> TYPE: PRT
<213> ORGANISM: Mus sp.

<400> SEQUENCE: 22

Lys Ala Ser Gln Asp Val Val Thr Ala Val Ala
1               5                   10

<210> SEQ ID NO 23
<211> LENGTH: 7
<212> TYPE: PRT
<213> ORGANISM: Mus sp.

<400> SEQUENCE: 23

Ser Ala Ser His Arg Tyr Thr
1               5
```

```
<210> SEQ ID NO 24
<211> LENGTH: 9
<212> TYPE: PRT
<213> ORGANISM: Mus sp.

<400> SEQUENCE: 24

Gln Gln His Tyr Thr Thr Pro Thr Thr
1               5

<210> SEQ ID NO 25
<211> LENGTH: 5
<212> TYPE: PRT
<213> ORGANISM: Mus sp.

<400> SEQUENCE: 25

Ser Tyr Thr Leu Ser
1               5

<210> SEQ ID NO 26
<211> LENGTH: 17
<212> TYPE: PRT
<213> ORGANISM: Mus sp.

<400> SEQUENCE: 26

Thr Ile Ser Ile Gly Gly Arg Tyr Thr Tyr Tyr Pro Asp Ser Val Glu
1               5                   10                  15

Gly

<210> SEQ ID NO 27
<211> LENGTH: 8
<212> TYPE: PRT
<213> ORGANISM: Mus sp.

<400> SEQUENCE: 27

Asp Phe Asn Gly Tyr Ser Asp Phe
1               5

<210> SEQ ID NO 28
<211> LENGTH: 11
<212> TYPE: PRT
<213> ORGANISM: Mus sp.

<400> SEQUENCE: 28

Lys Ala Ser Gln Val Val Gly Ser Ala Val Ala
1               5                   10

<210> SEQ ID NO 29
<211> LENGTH: 7
<212> TYPE: PRT
<213> ORGANISM: Mus sp.

<400> SEQUENCE: 29

Trp Ala Ser Thr Arg His Thr
1               5

<210> SEQ ID NO 30
<211> LENGTH: 9
<212> TYPE: PRT
<213> ORGANISM: Mus sp.

<400> SEQUENCE: 30

Gln Gln Tyr Asn Ser Tyr Pro Tyr Thr
1               5
```

```
<210> SEQ ID NO 31
<211> LENGTH: 5
<212> TYPE: PRT
<213> ORGANISM: Mus sp.

<400> SEQUENCE: 31

Asn Phe Gly Met His
1               5

<210> SEQ ID NO 32
<211> LENGTH: 17
<212> TYPE: PRT
<213> ORGANISM: Mus sp.

<400> SEQUENCE: 32

Tyr Ile Arg Ser Gly Ser Gly Thr Ile Tyr Tyr Ser Asp Thr Val Lys
1               5                   10                  15

Gly

<210> SEQ ID NO 33
<211> LENGTH: 11
<212> TYPE: PRT
<213> ORGANISM: Mus sp.

<400> SEQUENCE: 33

Ser Tyr Tyr Asp Phe Gly Ala Trp Phe Ala Tyr
1               5                   10

<210> SEQ ID NO 34
<211> LENGTH: 11
<212> TYPE: PRT
<213> ORGANISM: Mus sp.

<400> SEQUENCE: 34

Lys Ala Ser Gln Asn Val Gly Thr Asn Val Ala
1               5                   10

<210> SEQ ID NO 35
<211> LENGTH: 7
<212> TYPE: PRT
<213> ORGANISM: Mus sp.

<400> SEQUENCE: 35

Ser Ala Ser Ser Arg Tyr Ser
1               5

<210> SEQ ID NO 36
<211> LENGTH: 9
<212> TYPE: PRT
<213> ORGANISM: Mus sp.

<400> SEQUENCE: 36

Gln Gln Tyr Asn Ser Tyr Pro Leu Thr
1               5

<210> SEQ ID NO 37
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 37 aac att gtg ctg acc caa tct cca gct tct ttg gct gtg tct ctt ggg        48
```

```
                Asn Ile Val Leu Thr Gln Ser Pro Ala Ser Leu Ala Val Ser Leu Gly
                1               5                   10                  15 cag agg gcc acc ata tcc tgc aga gcc agt gaa agt gtt gag att tat          96
Gln Arg Ala Thr Ile Ser Cys Arg Ala Ser Glu Ser Val Glu Ile Tyr
            20                  25                  30 ggc aat ggt ttt atg aac tgg ttc cag cag aaa cca gga cag cca ccc          144
Gly Asn Gly Phe Met Asn Trp Phe Gln Gln Lys Pro Gly Gln Pro Pro
        35                  40                  45 aaa ctc ctc atc tat cgt gca tcc aac cta gaa tct ggg atc cct gcc          192
Lys Leu Leu Ile Tyr Arg Ala Ser Asn Leu Glu Ser Gly Ile Pro Ala
    50                  55                  60 agg ttc agt ggc agt ggg tct agg aca gag ttc acc ctc acc att gat          240
Arg Phe Ser Gly Ser Gly Ser Arg Thr Glu Phe Thr Leu Thr Ile Asp
65                  70                  75                  80 cct gtg gag gct gat gat gtt gca acc tat tac tgt caa caa att aat          288
Pro Val Glu Ala Asp Asp Val Ala Thr Tyr Tyr Cys Gln Gln Ile Asn
                85                  90                  95 gag gat cca ttc acg ttc ggc tcg ggg aca aag ttg gaa ata aaa cgg          336
Glu Asp Pro Phe Thr Phe Gly Ser Gly Thr Lys Leu Glu Ile Lys Arg
            100                 105                 110
```

<210> SEQ ID NO 38
<211> LENGTH: 112
<212> TYPE: PRT
<213> ORGANISM: Mus sp.

<400> SEQUENCE: 38

```
Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Glu Ile Tyr
            20                  25                  30

Gly Asn Gly Phe Met Asn Trp Phe Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Glu Phe Thr Leu Thr Ile Asp
65                  70                  75                  80

Pro Val Glu Ala Asp Asp Val Ala Thr Tyr Tyr Cys Gln Gln Ile Asn
                85                  90                  95

Glu Asp Pro Phe Thr Phe Gly Ser Gly Thr Lys Leu Glu Ile Lys Arg
            100                 105                 110
```

<210> SEQ ID NO 39
<211> LENGTH: 336
<212> TYPE: DNA
<213> ORGANISM: Mus sp.
<220> FEATURE:
<221> NAME/KEY: CDS
<222> LOCATION: (1)..(336)

<400> SEQUENCE: 39

```
gac att gta ctg acc caa tct cca gct tct ttg gct gtg tct cta ggg          48
Asp Ile Val Leu Thr Gln Ser Pro Ala Ser Leu Ala Val Ser Leu Gly
1               5                   10                  15 cag agg gcc acc ata tcc tgc aga gcc agt gag agt gtt gct att tat          96
Gln Arg Ala Thr Ile Ser Cys Arg Ala Ser Glu Ser Val Ala Ile Tyr
            20                  25                  30 ggc aat agt ttt ctg aaa tgg ttc cag cag aaa ccg gga cag cca ccc          144
Gly Asn Ser Phe Leu Lys Trp Phe Gln Gln Lys Pro Gly Gln Pro Pro
        35                  40                  45 aaa ctc ctc atc tat cgt gca tcc aac cta gaa tct ggg atc cct gcc          192
```

```
                Lys Leu Leu Ile Tyr Arg Ala Ser Asn Leu Glu Ser Gly Ile Pro Ala
                     50                  55                  60 agg ttc agt ggc agt ggg tct ggg aca gac ttc acc ctc acc att aat        240
Arg Phe Ser Gly Ser Gly Ser Gly Thr Asp Phe Thr Leu Thr Ile Asn
 65                  70                  75                  80 cct gtg gag gct gat gat gtt gca acc tat tac tgt cag caa att aat        288
Pro Val Glu Ala Asp Asp Val Ala Thr Tyr Tyr Cys Gln Gln Ile Asn
                 85                  90                  95 gag gat ccg tac acg ttc gga ggg ggg acc aag ctg gaa ata aaa cgg        336
Glu Asp Pro Tyr Thr Phe Gly Gly Gly Thr Lys Leu Glu Ile Lys Arg
            100                 105                 110
```

<210> SEQ ID NO 40
<211> LENGTH: 112
<212> TYPE: PRT
<213> ORGANISM: Mus sp.

<400> SEQUENCE: 40

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Ala Ile Tyr
             20                  25                  30

Gly Asn Ser Phe Leu Lys Trp Phe Gln Gln Lys Pro Gly Gln Pro Pro
         35                  40                  45

Lys Leu Leu Ile Tyr Arg Ala Ser Asn Leu Glu Ser Gly Ile Pro Ala
     50                  55                  60

Arg Phe Ser Gly Ser Gly Ser Gly Thr Asp Phe Thr Leu Thr Ile Asn
 65                  70                  75                  80

Pro Val Glu Ala Asp Asp Val Ala Thr Tyr Tyr Cys Gln Gln Ile Asn
                 85                  90                  95

Glu Asp Pro Tyr Thr Phe Gly Gly Gly Thr Lys Leu Glu Ile Lys Arg
            100                 105                 110

<210> SEQ ID NO 41
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 41

```
gac att gtg atg gcc cag tct cac aaa ttc atg tcc aca tca gtt gga        48
Asp Ile Val Met Ala Gln Ser His Lys Phe Met Ser Thr Ser Val Gly
 1               5                  10                  15 gac agg gtc agc atc acc tgc aag gcc agt cag gat gtg agt act gtt        96
Asp Arg Val Ser Ile Thr Cys Lys Ala Ser Gln Asp Val Ser Thr Val
             20                  25                  30 gtg gcc tgg tat caa cag aaa cca gga caa tct cct aaa cga ctg att       144
Val Ala Trp Tyr Gln Gln Lys Pro Gly Gln Ser Pro Lys Arg Leu Ile
         35                  40                  45 tac tcg gca tcc tat cgg tat att gga gtc cct gat cgc ttc act ggc       192
Tyr Ser Ala Ser Tyr Arg Tyr Ile Gly Val Pro Asp Arg Phe Thr Gly
     50                  55                  60 agt gga tct ggg acg gat ttc act ttc acc atc agc agt gtg cag gct       240
Ser Gly Ser Gly Thr Asp Phe Thr Phe Thr Ile Ser Ser Val Gln Ala
 65                  70                  75                  80 gaa gac ctg gca gtt tat tac tgt cag caa cat tat agt cct ccg tac       288
Glu Asp Leu Ala Val Tyr Tyr Cys Gln Gln His Tyr Ser Pro Pro Tyr
                 85                  90                  95 acg ttc gga ggg ggg acc aag ctg gaa ata aaa cgg                        324
```

Thr Phe Gly Gly Gly Thr Lys Leu Glu Ile Lys Arg
            100                 105

<210> SEQ ID NO 42
<211> LENGTH: 108
<212> TYPE: PRT
<213> ORGANISM: Mus sp.

<400> SEQUENCE: 42

Asp Ile Val Met Ala Gln Ser His Lys Phe Met Ser Thr Ser Val Gly
1               5                   10                  15

Asp Arg Val Ser Ile Thr Cys Lys Ala Ser Gln Asp Val Ser Thr Val
            20                  25                  30

Val Ala Trp Tyr Gln Gln Lys Pro Gly Gln Ser Pro Lys Arg Leu Ile
        35                  40                  45

Tyr Ser Ala Ser Tyr Arg Tyr Ile Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105

<210> SEQ ID NO 43
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 43 gac att gtg atg acc cag tct cac aaa ttc ttg tcc aca tca gtt gga      48
Asp Ile Val Met Thr Gln Ser His Lys Phe Leu Ser Thr Ser Val Gly
1               5                   10                  15 gac agg gtc agt atc acc tgc aag gcc agt cag gat gtg gtt act gct      96
Asp Arg Val Ser Ile Thr Cys Lys Ala Ser Gln Asp Val Val Thr Ala
            20                  25                  30 gtt gcc tgg ttt caa cag aaa cca gga caa tct cca aaa cta ctg att    144
Val Ala Trp Phe Gln Gln Lys Pro Gly Gln Ser Pro Lys Leu Leu Ile
        35                  40                  45 tat tcg gca tcc cac cgg tac act gga gtc cct gat cgc ttc act ggc    192
Tyr Ser Ala Ser His Arg Tyr Thr Gly Val Pro Asp Arg Phe Thr Gly
    50                  55                  60 agt gga tct ggg aca gat ttc act ttc acc atc atc agt gtg cag gct    240
Ser Gly Ser Gly Thr Asp Phe Thr Phe Thr Ile Ile Ser Val Gln Ala
65                  70                  75                  80 gaa gac ctg gca gtt tat tac tgt caa caa cat tat act act ccc acg    288
Glu Asp Leu Ala Val Tyr Tyr Cys Gln Gln His Tyr Thr Thr Pro Thr
                85                  90                  95 acg ttc ggt gga ggc acc aag ctg gac ttc aga cgg                    324
Thr Phe Gly Gly Gly Thr Lys Leu Asp Phe Arg Arg
            100                 105

<210> SEQ ID NO 44
<211> LENGTH: 108
<212> TYPE: PRT
<213> ORGANISM: Mus sp.

<400> SEQUENCE: 44

Asp Ile Val Met Thr Gln Ser His Lys Phe Leu Ser Thr Ser Val Gly

```
                1               5                   10                  15
Asp Arg Val Ser Ile Thr Cys Lys Ala Ser Gln Asp Val Thr Ala
            20                  25                  30

Val Ala Trp Phe Gln Gln Lys Pro Gly Gln Ser Pro Lys Leu Leu Ile
            35                  40                  45

Tyr Ser Ala Ser His Arg Tyr Thr Gly Val Pro Asp Arg Phe Thr Gly
            50                  55                  60

Ser Gly Ser Gly Thr Asp Phe Thr Phe Thr Ile Ser Val Gln Ala
65                      70                  75                  80

Glu Asp Leu Ala Val Tyr Tyr Cys Gln Gln His Tyr Thr Thr Pro Thr
                85                  90                  95

Thr Phe Gly Gly Gly Thr Lys Leu Asp Phe Arg Arg
            100                 105

<210> SEQ ID NO 45
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 45 gac act gtg atg acc cag tct cac aaa ttc ata tcc aca tca gtt gga        48
Asp Thr Val Met Thr Gln Ser His Lys Phe Ile Ser Thr Ser Val Gly
1               5                   10                  15 gac agg gtc agc atc acc tgc aag gcc agt cag gtt gtg ggt agt gct       96
Asp Arg Val Ser Ile Thr Cys Lys Ala Ser Gln Val Val Gly Ser Ala
            20                  25                  30 gta gcc tgg tat caa cag aaa cca ggg caa tct cct aaa cta ctg att      144
Val Ala Trp Tyr Gln Gln Lys Pro Gly Gln Ser Pro Lys Leu Leu Ile
            35                  40                  45 tac tgg gca tcc acc cgg cac act gga gtc cct gat cgc ttc aca ggc      192
Tyr Trp Ala Ser Thr Arg His Thr Gly Val Pro Asp Arg Phe Thr Gly
            50                  55                  60 agt gga tct ggg aca gat ttc act ctc acc att agc aat gtg cag tct      240
Ser Gly Ser Gly Thr Asp Phe Thr Leu Thr Ile Ser Asn Val Gln Ser
65                      70                  75                  80 gaa gac ttg gca gat tat ttc tgt cag caa tat aac agc tat ccg tac      288
Glu Asp Leu Ala Asp Tyr Phe Cys Gln Gln Tyr Asn Ser Tyr Pro Tyr
                85                  90                  95 acg ttc gga ggg ggg acc aag ctg gaa ata aaa cgg                      324
Thr Phe Gly Gly Gly Thr Lys Leu Glu Ile Lys Arg
            100                 105

<210> SEQ ID NO 46
<211> LENGTH: 108
<212> TYPE: PRT
<213> ORGANISM: Mus sp.

<400> SEQUENCE: 46

Asp Thr Val Met Thr Gln Ser His Lys Phe Ile Ser Thr Ser Val Gly
1               5                   10                  15

Asp Arg Val Ser Ile Thr Cys Lys Ala Ser Gln Val Val Gly Ser Ala
            20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
            50                  55                  60

Ser Gly Ser Gly Thr Asp Phe Thr Leu Thr Ile Ser Asn Val Gln Ser
```

```
                65                  70                  75                  80
Glu Asp Leu Ala Asp Tyr Phe Cys Gln Gln Tyr Asn Ser Tyr Pro Tyr
                    85                  90                  95

Thr Phe Gly Gly Gly Thr Lys Leu Glu Ile Lys Arg
            100                 105

<210> SEQ ID NO 47
<211> LENGTH: 324
<212> TYPE: DNA
<213> ORGANISM: Mus sp.
<220> FEATURE:
<221> NAME/KEY: CDS
<222> LOCATION: (1)..(324)

<400> SEQUENCE: 47 gac att gtg atg acc cag tct caa aaa ttc atg tcc aca tca gta gga      48
Asp Ile Val Met Thr Gln Ser Gln Lys Phe Met Ser Thr Ser Val Gly
1               5                   10                  15 gac agg gtc agc gtc acc tgc aag gcc agt cag aat gtg ggt act aat      96
Asp Arg Val Ser Val Thr Cys Lys Ala Ser Gln Asn Val Gly Thr Asn
            20                  25                  30 gtt gcc tgg tat caa cac aaa cca gga caa tcc cct aaa ata atg att     144
Val Ala Trp Tyr Gln His Lys Pro Gly Gln Ser Pro Lys Ile Met Ile
        35                  40                  45 tat tcg gcg tcc tcc cgg tac agt gga gtc cct gat cgc ttc aca ggc     192
Tyr Ser Ala Ser Ser Arg Tyr Ser Gly Val Pro Asp Arg Phe Thr Gly
    50                  55                  60 agt gga tct ggg aca ctt ttc act ctc acc atc aac aat gtg cag tct     240
Ser Gly Ser Gly Thr Leu Phe Thr Leu Thr Ile Asn Asn Val Gln Ser
65                  70                  75                  80 gaa gac ttg gca gag tat ttc tgt cag caa tat aac agc tat cct ctc     288
Glu Asp Leu Ala Glu Tyr Phe Cys Gln Gln Tyr Asn Ser Tyr Pro Leu
                85                  90                  95 acg ttc ggc tcg ggg aca aag ttg gaa ata aaa cgg                     324
Thr Phe Gly Ser Gly Thr Lys Leu Glu Ile Lys Arg
            100                 105

<210> SEQ ID NO 48
<211> LENGTH: 108
<212> TYPE: PRT
<213> ORGANISM: Mus sp.

<400> SEQUENCE: 48

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln His Lys Pro Gly Gln Ser Pro Lys Ile Met Ile
        35                  40                  45

Tyr Ser Ala Ser Ser Arg Tyr Ser Gly Val Pro Asp Arg Phe Thr Gly
    50                  55                  60

Ser Gly Ser Gly Thr Leu Phe Thr Leu Thr Ile Asn Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ser Gly Thr Lys Leu Glu Ile Lys Arg
            100                 105

<210> SEQ ID NO 49
<211> LENGTH: 342
<212> TYPE: DNA
```

<213> ORGANISM: Mus sp.
<220> FEATURE:
<221> NAME/KEY: CDS
<222> LOCATION: (1)..(342)

<400> SEQUENCE: 49

```
cag atc cag ttg gtg cag tct gga cct gag ctg aag aag cct gga gag       48
Gln Ile Gln Leu Val Gln Ser Gly Pro Glu Leu Lys Lys Pro Gly Glu
1               5                   10                  15 aca gtc aag atc tcc tgc aag gct tct ggg tat acc ctc aca agc tac       96
Thr Val Lys Ile Ser Cys Lys Ala Ser Gly Tyr Thr Leu Thr Ser Tyr
            20                  25                  30 gga atg aac tgg gtg aag cag gct cca gga aag ggt tta aag tgg atg      144
Gly Met Asn Trp Val Lys Gln Ala Pro Gly Lys Gly Leu Lys Trp Met
        35                  40                  45 ggc tgg ata aac acc tac act gga gaa cca aca tat gct gat gac ttt      192
Gly Trp Ile Asn Thr Tyr Thr Gly Glu Pro Thr Tyr Ala Asp Asp Phe
    50                  55                  60 aag gga cgt ttt gcc ttc tct ttg gaa acc tct gcc agc act gcc ttt      240
Lys Gly Arg Phe Ala Phe Ser Leu Glu Thr Ser Ala Ser Thr Ala Phe
65                  70                  75                  80 ttg cag atc aac aac ctc aaa aat gag gac acg gct aca tat ttc tgt      288
Leu Gln Ile Asn Asn Leu Lys Asn Glu Asp Thr Ala Thr Tyr Phe Cys
                85                  90                  95 gta aga cgc ggg ttt gct tac tgg ggc caa ggg act ctg gtc act gtc      336
Val Arg Arg Gly Phe Ala Tyr Trp Gly Gln Gly Thr Leu Val Thr Val
            100                 105                 110 tct gca                                                              342
Ser Ala
```

<210> SEQ ID NO 50
<211> LENGTH: 114
<212> TYPE: PRT
<213> ORGANISM: Mus sp.

<400> SEQUENCE: 50

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Leu Thr Ser Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Phe
65                  70                  75                  80

Leu Gln Ile Asn Asn Leu Lys Asn Glu Asp Thr Ala Thr Tyr Phe Cys
                85                  90                  95

Val Arg Arg Gly Phe Ala Tyr Trp Gly Gln Gly Thr Leu Val Thr Val
            100                 105                 110

Ser Ala
```

<210> SEQ ID NO 51
<211> LENGTH: 342
<212> TYPE: DNA
<213> ORGANISM: Mus sp.
<220> FEATURE:
<221> NAME/KEY: CDS
<222> LOCATION: (1)..(342)

<400> SEQUENCE: 51

```
cag atc cag ttg gtg cag tct gga cct gag ctg aag aag cct gga gag        48
Gln Ile Gln Leu Val Gln Ser Gly Pro Glu Leu Lys Lys Pro Gly Glu
1               5                   10                  15 aca gtc aag atc tcc tgc aag gct tct ggg tat acc ttc aca aac tct        96
Thr Val Lys Ile Ser Cys Lys Ala Ser Gly Tyr Thr Phe Thr Asn Ser
            20                  25                  30 gga atg aac tgg gtg aag cag gct cca gga aag ggt tta aag tgg atg       144
Gly Met Asn Trp Val Lys Gln Ala Pro Gly Lys Gly Leu Lys Trp Met
        35                  40                  45 ggc tgg ata aac acc tac act gga gag ccg aca tat gct gat gac ttc       192
Gly Trp Ile Asn Thr Tyr Thr Gly Glu Pro Thr Tyr Ala Asp Asp Phe
    50                  55                  60 aag gga cgg ttt gcc ttc tct ttg gaa acc tct gcc agc tct gcc tat       240
Lys Gly Arg Phe Ala Phe Ser Leu Glu Thr Ser Ala Ser Ser Ala Tyr
65                  70                  75                  80 ttg cag atc agt aac ctc aaa aat gag gac acg gct aca tat ttc tgt       288
Leu Gln Ile Ser Asn Leu Lys Asn Glu Asp Thr Ala Thr Tyr Phe Cys
                85                  90                  95 gca aga agg ggt ttt gtt tac tgg ggc caa ggg act ctg gta act gtc       336
Ala Arg Arg Gly Phe Val Tyr Trp Gly Gln Gly Thr Leu Val Thr Val
            100                 105                 110 tct gca                                                                342
Ser Ala <210> SEQ ID NO 52
<211> LENGTH: 114
<212> TYPE: PRT
<213> ORGANISM: Mus sp.

<400> SEQUENCE: 52

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Ser
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Ser Ala Tyr
65                  70                  75                  80

Leu Gln Ile Ser Asn Leu Lys Asn Glu Asp Thr Ala Thr Tyr Phe Cys
                85                  90                  95

Ala Arg Arg Gly Phe Val Tyr Trp Gly Gln Gly Thr Leu Val Thr Val
            100                 105                 110

Ser Ala

<210> SEQ ID NO 53
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 53 cag gtt cag ctc cag cag tct ggg gct gag ctg gca aga cct ggg act        48
Gln Val Gln Leu Gln Gln Ser Gly Ala Glu Leu Ala Arg Pro Gly Thr
1               5                   10                  15 tca gtg aag ttg tcc tgt aag gct tct ggc tac acc ttt act gac tac        96
Ser Val Lys Leu Ser Cys Lys Ala Ser Gly Tyr Thr Phe Thr Asp Tyr
            20                  25                  30
```

```
tgg atg cag tgg gta aaa cag agg cct gga cag ggt ctg gag tgg att    144
Trp Met Gln Trp Val Lys Gln Arg Pro Gly Gln Gly Leu Glu Trp Ile
         35                  40                  45 ggg act att tat cct gga gat ggt gat act ggg tac gct cag aag ttc    192
Gly Thr Ile Tyr Pro Gly Asp Gly Asp Thr Gly Tyr Ala Gln Lys Phe
 50                  55                  60 aag ggc aag gcc aca ttg act gcg gat aaa tcc tcc aaa aca gtc tac    240
Lys Gly Lys Ala Thr Leu Thr Ala Asp Lys Ser Ser Lys Thr Val Tyr
 65                  70                  75                  80 atg cac ctc agc agt ttg gct tct gag gac tct gcg gtc tat tac tgt    288
Met His Leu Ser Ser Leu Ala Ser Glu Asp Ser Ala Val Tyr Tyr Cys
                 85                  90                  95 gca aga ggg gat tac tac ggt agt aat tct ttg gac tat tgg ggt caa    336
Ala Arg Gly Asp Tyr Tyr Gly Ser Asn Ser Leu Asp Tyr Trp Gly Gln
            100                 105                 110 gga acc tca gtc acc gtc tcc tca                                    360
Gly Thr Ser Val Thr Val Ser Ser
            115                 120

<210> SEQ ID NO 54
<211> LENGTH: 120
<212> TYPE: PRT
<213> ORGANISM: Mus sp.

<400> SEQUENCE: 54

Gln Val Gln Leu Gln Gln Ser Gly Ala Glu Leu Ala Arg Pro Gly Thr
 1               5                  10                  15

Ser Val Lys Leu Ser Cys Lys Ala Ser Gly Tyr Thr Phe Thr Asp Tyr
             20                  25                  30

Trp Met Gln Trp Val Lys Gln Arg Pro Gly Gln Gly Leu Glu Trp Ile
         35                  40                  45

Gly Thr Ile Tyr Pro Gly Asp Gly Asp Thr Gly Tyr Ala Gln Lys Phe
 50                  55                  60

Lys Gly Lys Ala Thr Leu Thr Ala Asp Lys Ser Ser Lys Thr Val Tyr
 65                  70                  75                  80

Met His Leu Ser Ser Leu Ala Ser Glu Asp Ser Ala Val Tyr Tyr Cys
                 85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
            115                 120

<210> SEQ ID NO 55
<211> LENGTH: 357
<212> TYPE: DNA
<213> ORGANISM: Mus sp.
<220> FEATURE:
<221> NAME/KEY: CDS
<222> LOCATION: (1)..(357)

<400> SEQUENCE: 55 cag gtc cag tta cag caa tct gga cct gaa ctg gtg agg cct ggg gcc     48
Gln Val Gln Leu Gln Gln Ser Gly Pro Glu Leu Val Arg Pro Gly Ala
 1               5                  10                  15 tca gtg aag att tcc tgc aaa act tct ggc tac gca ttc agt ggc tcc     96
Ser Val Lys Ile Ser Cys Lys Thr Ser Gly Tyr Ala Phe Ser Gly Ser
             20                  25                  30 tgg atg aac tgg gtg aag cag agg cct gga cag ggt cta gag tgg att    144
Trp Met Asn Trp Val Lys Gln Arg Pro Gly Gln Gly Leu Glu Trp Ile
         35                  40                  45
```

```
gga cgg att tat ccg gga gat gga gat atc att tac aat ggg aat ttc      192
Gly Arg Ile Tyr Pro Gly Asp Gly Asp Ile Ile Tyr Asn Gly Asn Phe
    50                  55                  60 agg gac aag gtc aca ctg tct gca gac aaa tcc tcc aac aca gcc tac      240
Arg Asp Lys Val Thr Leu Ser Ala Asp Lys Ser Ser Asn Thr Ala Tyr
65                  70                  75                  80 atg cag ctc agc agc ctg acc tct gtg gac tct gcg gtc tat ttt tgt      288
Met Gln Leu Ser Ser Leu Thr Ser Val Asp Ser Ala Val Tyr Phe Cys
                85                  90                  95 tcg aga tgg ggg aca ttt acg ccg agt ttt gac tat tgg ggc caa ggc      336
Ser Arg Trp Gly Thr Phe Thr Pro Ser Phe Asp Tyr Trp Gly Gln Gly
            100                 105                 110 acc act ctc aca gtc tcc tca                                          357
Thr Thr Leu Thr Val Ser Ser
            115
```

<210> SEQ ID NO 56
<211> LENGTH: 119
<212> TYPE: PRT
<213> ORGANISM: Mus sp.

<400> SEQUENCE: 56

```
Gln Val Gln Leu Gln Gln Ser Gly Pro Glu Leu Val Arg Pro Gly Ala
1               5                   10                  15

Ser Val Lys Ile Ser Cys Lys Thr Ser Gly Tyr Ala Phe Ser Gly Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Ile Ile Tyr Asn Gly Asn Phe
    50                  55                  60

Arg Asp Lys Val Thr Leu Ser Ala Asp Lys Ser Ser Asn Thr Ala Tyr
65                  70                  75                  80

Met Gln Leu Ser Ser Leu Thr Ser Val Asp Ser Ala Val Tyr Phe Cys
                85                  90                  95

Ser Arg Trp Gly Thr Phe Thr Pro Ser Phe Asp Tyr Trp Gly Gln Gly
            100                 105                 110

Thr Thr Leu Thr Val Ser Ser
            115
```

<210> SEQ ID NO 57
<211> LENGTH: 351
<212> TYPE: DNA
<213> ORGANISM: Mus sp.
<220> FEATURE:
<221> NAME/KEY: CDS
<222> LOCATION: (1)..(351)

<400> SEQUENCE: 57

```
gac gtg aag ctg gtg gag tct ggg gga ggc tta gtg aag cct gga ggg      48
Asp Val Lys Leu Val Glu Ser Gly Gly Gly Leu Val Lys Pro Gly Gly
1               5                   10                  15 tcc ctg aaa ctc tcc tgt gaa gcc tct gga ttc act ttc agt agc tat      96
Ser Leu Lys Leu Ser Cys Glu Ala Ser Gly Phe Thr Phe Ser Ser Tyr
            20                  25                  30 acc ctg tct tgg gtt cgc cag act ccg gag acg agg ctg gag tgg gtc     144
Thr Leu Ser Trp Val Arg Gln Thr Pro Glu Thr Arg Leu Glu Trp Val
        35                  40                  45 gca acc att agt att ggt ggt cgc tac acc tat tat cca gac agt gtg     192
Ala Thr Ile Ser Ile Gly Gly Arg Tyr Thr Tyr Tyr Pro Asp Ser Val
    50                  55                  60 gag ggc cga ttc acc atc tcc aga gac aat gcc aag aac acc ctg tac     240
Glu Gly Arg Phe Thr Ile Ser Arg Asp Asn Ala Lys Asn Thr Leu Tyr
```

```
Glu Gly Arg Phe Thr Ile Ser Arg Asp Asn Ala Lys Asn Thr Leu Tyr
 65                  70                  75                  80 ctg caa atg aac agt ctg aag tct gag gac aca gcc atg tat tac tgt      288
Leu Gln Met Asn Ser Leu Lys Ser Glu Asp Thr Ala Met Tyr Tyr Cys
                 85                  90                  95 aca aga gat ttt aat ggt tac tct gac ttc tgg ggc caa ggc acc act      336
Thr Arg Asp Phe Asn Gly Tyr Ser Asp Phe Trp Gly Gln Gly Thr Thr
            100                 105                 110 ctc aca gtc tcc tca                                                  351
Leu Thr Val Ser Ser
        115

<210> SEQ ID NO 58
<211> LENGTH: 117
<212> TYPE: PRT
<213> ORGANISM: Mus sp.

<400> SEQUENCE: 58

Asp Val Lys Leu Val Glu Ser Gly Gly Gly Leu Val Lys Pro Gly Gly
  1               5                  10                  15

Ser Leu Lys Leu Ser Cys Glu Ala Ser Gly Phe Thr Phe Ser Ser Tyr
             20                  25                  30

Thr Leu Ser Trp Val Arg Gln Thr Pro Glu Thr Arg Leu Glu Trp Val
         35                  40                  45

Ala Thr Ile Ser Ile Gly Gly Arg Tyr Thr Tyr Tyr Pro Asp Ser Val
     50                  55                  60

Glu Gly Arg Phe Thr Ile Ser Arg Asp Asn Ala Lys Asn Thr Leu Tyr
 65                  70                  75                  80

Leu Gln Met Asn Ser Leu Lys Ser Glu Asp Thr Ala Met Tyr Tyr Cys
                 85                  90                  95

Thr Arg Asp Phe Asn Gly Tyr Ser Asp Phe Trp Gly Gln Gly Thr Thr
            100                 105                 110

Leu Thr Val Ser Ser
        115

<210> SEQ ID NO 59
<211> LENGTH: 360
<212> TYPE: DNA
<213> ORGANISM: Mus sp.
<220> FEATURE:
<221> NAME/KEY: CDS
<222> LOCATION: (1)..(360)

<400> SEQUENCE: 59 aat gta cag ctg gta gag tct ggg gga ggc tta gtg cag cct gga ggg       48
Asn Val Gln Leu Val Glu Ser Gly Gly Gly Leu Val Gln Pro Gly Gly
  1               5                  10                  15 tcc cgg aaa ctc tcc tgt gca gcc tct gga ttc act ttc agt aac ttt       96
Ser Arg Lys Leu Ser Cys Ala Ala Ser Gly Phe Thr Phe Ser Asn Phe
             20                  25                  30 gga atg cac tgg gtt cgt cag gct cca gag aag ggt ctg gag tgg gtc      144
Gly Met His Trp Val Arg Gln Ala Pro Glu Lys Gly Leu Glu Trp Val
         35                  40                  45 gca tac att cgt agt ggc agt ggt acc atc tac tat tca gac aca gtg      192
Ala Tyr Ile Arg Ser Gly Ser Gly Thr Ile Tyr Tyr Ser Asp Thr Val
     50                  55                  60 aag ggc cga ttc acc atc tcc aga gac aat ccc aag aac acc ctg ttc      240
Lys Gly Arg Phe Thr Ile Ser Arg Asp Asn Pro Lys Asn Thr Leu Phe
 65                  70                  75                  80 ctg caa atg acc agt cta agg tct gag gac acg gcc atg tat tac tgt      288
Leu Gln Met Thr Ser Leu Arg Ser Glu Asp Thr Ala Met Tyr Tyr Cys
```

```
                    85                  90                  95
gca aga tcc tac tat gat ttc ggg gcc tgg ttt gct tac tgg ggc caa      336
Ala Arg Ser Tyr Tyr Asp Phe Gly Ala Trp Phe Ala Tyr Trp Gly Gln
            100                 105                 110 ggg act ctg gtc act gtc tct gca                                      360
Gly Thr Leu Val Thr Val Ser Ala
        115                 120

<210> SEQ ID NO 60
<211> LENGTH: 120
<212> TYPE: PRT
<213> ORGANISM: Mus sp.

<400> SEQUENCE: 60

Asn Val Gln Leu Val Glu Ser Gly Gly Leu Val Gln Pro Gly Gly
 1               5                  10                  15

Ser Arg Lys Leu Ser Cys Ala Ala Ser Gly Phe Thr Phe Ser Asn Phe
             20                  25                  30

Gly Met His Trp Val Arg Gln Ala Pro Glu Lys Gly Leu Glu Trp Val
         35                  40                  45

Ala Tyr Ile Arg Ser Gly Ser Gly Thr Ile Tyr Tyr Ser Asp Thr Val
     50                  55                  60

Lys Gly Arg Phe Thr Ile Ser Arg Asp Asn Pro Lys Asn Thr Leu Phe
 65                  70                  75                  80

Leu Gln Met Thr Ser Leu Arg Ser Glu Asp Thr Ala Met Tyr Tyr Cys
                 85                  90                  95

Ala Arg Ser Tyr Tyr Asp Phe Gly Ala Trp Phe Ala Tyr Trp Gly Gln
            100                 105                 110

Gly Thr Leu Val Thr Val Ser Ala
        115                 120

<210> SEQ ID NO 61
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 61 gat atc gta atg acc cag tcc cac ctg agt atg agt acc tcc ctg gga      48
Asp Ile Val Met Thr Gln Ser His Leu Ser Met Ser Thr Ser Leu Gly
 1               5                  10                  15 gat cct gtg tca atc act tgc aag gcc tca cag gat gtg agc acc gtc      96
Asp Pro Val Ser Ile Thr Cys Lys Ala Ser Gln Asp Val Ser Thr Val
             20                  25                  30 gtt gct tgg tat cag cag aag ccc ggg caa tca ccc aga cgt ctc atc     144
Val Ala Trp Tyr Gln Gln Lys Pro Gly Gln Ser Pro Arg Arg Leu Ile
         35                  40                  45 tac tca gca tca tac cgt tac atc ggg gtg cct gac cga ttt act ggc     192
Tyr Ser Ala Ser Tyr Arg Tyr Ile Gly Val Pro Asp Arg Phe Thr Gly
     50                  55                  60 tct ggc gct ggc aca gat ttc acc ttt aca att agt tcc gtc cag gcc     240
Ser Gly Ala Gly Thr Asp Phe Thr Phe Thr Ile Ser Ser Val Gln Ala
 65                  70                  75                  80 gaa gac ctg gcc gtg tac tac tgc cag cag cac tac agt ccc cca tac     288
Glu Asp Leu Ala Val Tyr Tyr Cys Gln Gln His Tyr Ser Pro Pro Tyr
                 85                  90                  95 act ttc ggg gga ggg act aag ctc gaa atc aaa cgt                     324
Thr Phe Gly Gly Gly Thr Lys Leu Glu Ile Lys Arg
            100                 105
```

<210> SEQ ID NO 62
<211> LENGTH: 108
<212> TYPE: PRT
<213> ORGANISM: Homo sapiens

<400> SEQUENCE: 62

```
Asp Ile Val Met Thr Gln Ser His Leu Ser Met Ser Thr Ser Leu Gly
1               5                   10                  15

Asp Pro Val Ser Ile Thr Cys Lys Ala Ser Gln Asp Val Ser Thr Val
            20                  25                  30

Val Ala Trp Tyr Gln Gln Lys Pro Gly Gln Ser Pro Arg Arg Leu Ile
        35                  40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Pro Pro Tyr
                85                  90                  95

Thr Phe Gly Gly Gly Thr Lys Leu Glu Ile Lys Arg
            100                 105
```

<210> SEQ ID NO 63
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 63

```
gac att gtt atg gct caa agc cat ctg tct atg agc aca tct ctg gga      48
Asp Ile Val Met Ala Gln Ser His Leu Ser Met Ser Thr Ser Leu Gly
1               5                   10                  15 gat cct gtg tcc atc act tgc aaa gcc agt caa gac gtg tct aca gtt      96
Asp Pro Val Ser Ile Thr Cys Lys Ala Ser Gln Asp Val Ser Thr Val
            20                  25                  30 gtt gca tgg tat caa cag aag cca ggc cag tca ccc aga cgg ctc att     144
Val Ala Trp Tyr Gln Gln Lys Pro Gly Gln Ser Pro Arg Arg Leu Ile
        35                  40                  45 tac tca gct tct tac cga tac atc ggg gtc cct gac aga ttt aca ggt     192
Tyr Ser Ala Ser Tyr Arg Tyr Ile Gly Val Pro Asp Arg Phe Thr Gly
    50                  55                  60 agt ggg gcc ggt act gac ttc act ttt act atc tca tcc gta caa gcc     240
Ser Gly Ala Gly Thr Asp Phe Thr Phe Thr Ile Ser Ser Val Gln Ala
65                  70                  75                  80 gaa gac ctg gca gta tat tac tgc cag caa cat tat tcc cca ccc tac     288
Glu Asp Leu Ala Val Tyr Tyr Cys Gln Gln His Tyr Ser Pro Pro Tyr
                85                  90                  95 aca ttc ggc ggg ggt act aag ctg gaa att aaa cgt                     324
Thr Phe Gly Gly Gly Thr Lys Leu Glu Ile Lys Arg
            100                 105
```

<210> SEQ ID NO 64
<211> LENGTH: 108
<212> TYPE: PRT
<213> ORGANISM: Homo sapiens

<400> SEQUENCE: 64

```
Asp Ile Val Met Ala Gln Ser His Leu Ser Met Ser Thr Ser Leu Gly
1               5                   10                  15
```

```
Asp Pro Val Ser Ile Thr Cys Lys Ala Ser Gln Asp Val Ser Thr Val
         20                  25                  30

Val Ala Trp Tyr Gln Lys Pro Gly Gln Ser Pro Arg Leu Ile
         35              40                  45

Tyr Ser Ala Ser Tyr Arg Tyr Ile Gly Val Pro Asp Arg Phe Thr Gly
    50                  55                  60

Ser Gly Ala Gly Thr Asp Phe Thr Phe Thr Ile Ser Ser Val Gln Ala
65                   70                  75                  80

Glu Asp Leu Ala Val Tyr Tyr Cys Gln Gln His Tyr Ser Pro Pro Tyr
                 85                  90                  95

Thr Phe Gly Gly Gly Thr Lys Leu Glu Ile Lys Arg
            100                 105
```

<210> SEQ ID NO 65
<211> LENGTH: 360
<212> TYPE: DNA
<213> ORGANISM: Homo sapiens
<220> FEATURE:
<221> NAME/KEY: CDS
<222> LOCATION: (1)..(360)

<400> SEQUENCE: 65

```
cag gta cag ctc gtt cag tcc ggc gcc gag gta gct aag cct ggt act      48
Gln Val Gln Leu Val Gln Ser Gly Ala Glu Val Ala Lys Pro Gly Thr
1               5                   10                  15 tcc gta aaa ttg tcc tgt aag gct tcc ggg tac aca ttt aca gac tac      96
Ser Val Lys Leu Ser Cys Lys Ala Ser Gly Tyr Thr Phe Thr Asp Tyr
             20                  25                  30 tgg atg cag tgg gta aaa cag cgg cca ggt cag ggc ctg gag tgg att     144
Trp Met Gln Trp Val Lys Gln Arg Pro Gly Gln Gly Leu Glu Trp Ile
         35                  40                  45 gga aca ata tat ccc ggc gac ggc gac aca ggc tat gcc cag aag ttt     192
Gly Thr Ile Tyr Pro Gly Asp Gly Asp Thr Gly Tyr Ala Gln Lys Phe
    50                  55                  60 caa ggc aag gca acc ctt act gct gat aaa tct tcc aag act gtc tac     240
Gln Gly Lys Ala Thr Leu Thr Ala Asp Lys Ser Ser Lys Thr Val Tyr
65                  70                  75                  80 atg cat ctg tct tcc ttg gca tct gag gat agc gct gtc tat tac tgt     288
Met His Leu Ser Ser Leu Ala Ser Glu Asp Ser Ala Val Tyr Tyr Cys
                 85                  90                  95 gct agg ggg gac tac tat ggg tca aat tcc ctg gat tac tgg ggc cag     336
Ala Arg Gly Asp Tyr Tyr Gly Ser Asn Ser Leu Asp Tyr Trp Gly Gln
            100                 105                 110 ggc acc agt gtc acc gtg agc agc                                     360
Gly Thr Ser Val Thr Val Ser Ser
            115                 120
```

<210> SEQ ID NO 66
<211> LENGTH: 120
<212> TYPE: PRT
<213> ORGANISM: Homo sapiens

<400> SEQUENCE: 66

```
Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
             20                  25                  30

Trp Met Gln Trp Val Lys Gln Arg Pro Gly Gln Gly Leu Glu Trp Ile
         35                  40                  45

Gly Thr Ile Tyr Pro Gly Asp Gly Asp Thr Gly Tyr Ala Gln Lys Phe
    50                  55                  60
```

```
Gln Gly Lys Ala Thr Leu Thr Ala Asp Lys Ser Ser Lys Thr Val Tyr
 65                  70                  75                  80

Met His Leu Ser Ser Leu Ala Ser Glu Asp Ser Ala Val Tyr Tyr Cys
                 85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
            115                 120

<210> SEQ ID NO 67
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 67 gac acc gtg atg acc cag tcc ccc tcc acc atc tcc acc tct gtg ggc      48
Asp Thr Val Met Thr Gln Ser Pro Ser Thr Ile Ser Thr Ser Val Gly
 1               5                  10                  15 gac cgg gtg tcc atc acc tgt aag gcc tcc cag gtg gtg ggc tcc gcc      96
Asp Arg Val Ser Ile Thr Cys Lys Ala Ser Gln Val Val Gly Ser Ala
             20                  25                  30 gtg gcc tgg tat cag cag aag cct ggc cag tcc cct aag ctg ctg atc     144
Val Ala Trp Tyr Gln Gln Lys Pro Gly Gln Ser Pro Lys Leu Leu Ile
         35                  40                  45 tac tgg gcc tcc acc cgg cat acc ggc gtg cct gac cgg ttc acc ggc     192
Tyr Trp Ala Ser Thr Arg His Thr Gly Val Pro Asp Arg Phe Thr Gly
     50                  55                  60 tcc ggc agc ggc acc gac ttc acc ctg acc atc tcc aac gtg cag tcc     240
Ser Gly Ser Gly Thr Asp Phe Thr Leu Thr Ile Ser Asn Val Gln Ser
 65                  70                  75                  80 gac gac ctg gcc gac tac ttc tgc cag cag tac aac tcc tac cct tac     288
Asp Asp Leu Ala Asp Tyr Phe Cys Gln Gln Tyr Asn Ser Tyr Pro Tyr
                 85                  90                  95 acc ttt ggc ggc gga aca aag ctg gag atc aag cgt                     324
Thr Phe Gly Gly Gly Thr Lys Leu Glu Ile Lys Arg
            100                 105

<210> SEQ ID NO 68
<211> LENGTH: 108
<212> TYPE: PRT
<213> ORGANISM: Homo sapiens

<400> SEQUENCE: 68

Asp Thr Val Met Thr Gln Ser Pro Ser Thr Ile Ser Thr Ser Val Gly
 1               5                  10                  15

Asp Arg Val Ser Ile Thr Cys Lys Ala Ser Gln Val Val Gly Ser Ala
             20                  25                  30

Val Ala Trp Tyr Gln Gln Lys Pro Gly Gln Ser Pro Lys Leu Leu Ile
         35                  40                  45

Tyr Trp Ala Ser Thr Arg His Thr Gly Val Pro Asp Arg Phe Thr Gly
     50                  55                  60

Ser Gly Ser Gly Thr Asp Phe Thr Leu Thr Ile Ser Asn Val Gln Ser
 65                  70                  75                  80

Asp Asp Leu Ala Asp Tyr Phe Cys Gln Gln Tyr Asn Ser Tyr Pro Tyr
                 85                  90                  95

Thr Phe Gly Gly Gly Thr Lys Leu Glu Ile Lys Arg
            100                 105
```

<210> SEQ ID NO 69
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 69

```
gac acc gtg atg acc cag tcc ccc tcc tcc atc tcc acc tcc atc ggc      48
Asp Thr Val Met Thr Gln Ser Pro Ser Ser Ile Ser Thr Ser Ile Gly
1               5                   10                  15 gac cgg gtg tcc atc acc tgt aag gcc tcc cag gtg gtg ggc tcc gcc      96
Asp Arg Val Ser Ile Thr Cys Lys Ala Ser Gln Val Val Gly Ser Ala
            20                  25                  30 gtg gcc tgg tat cag cag aag cct ggc cag tcc cct aag ctg ctg atc     144
Val Ala Trp Tyr Gln Gln Lys Pro Gly Gln Ser Pro Lys Leu Leu Ile
        35                  40                  45 tac tgg gcc tcc acc cgg cat acc ggc gtg cct gcc cgg ttc acc ggc     192
Tyr Trp Ala Ser Thr Arg His Thr Gly Val Pro Ala Arg Phe Thr Gly
    50                  55                  60 tcc ggc agc ggc acc gac ttc acc ctg acc atc tcc aac gtg cag tcc     240
Ser Gly Ser Gly Thr Asp Phe Thr Leu Thr Ile Ser Asn Val Gln Ser
65                  70                  75                  80 gag gac ctg gcc gac tac ttc tgc cag cag tac aac tcc tac cct tac     288
Glu Asp Leu Ala Asp Tyr Phe Cys Gln Gln Tyr Asn Ser Tyr Pro Tyr
                85                  90                  95 acc ttt ggc ggc gga aca aag ctg gag atc aag cgt                     324
Thr Phe Gly Gly Gly Thr Lys Leu Glu Ile Lys Arg
            100                 105
```

<210> SEQ ID NO 70
<211> LENGTH: 108
<212> TYPE: PRT
<213> ORGANISM: Homo sapiens

<400> SEQUENCE: 70

```
Asp Thr Val Met Thr Gln Ser Pro Ser Ser Ile Ser Thr Ser Ile Gly
1               5                   10                  15

Asp Arg Val Ser Ile Thr Cys Lys Ala Ser Gln Val Val Gly Ser Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Ala Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Asn Ser Tyr Pro Tyr
                85                  90                  95

Thr Phe Gly Gly Gly Thr Lys Leu Glu Ile Lys Arg
            100                 105
```

<210> SEQ ID NO 71
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 71

```
gag gtg cag ctg gtg gag tct ggc ggc gga ctg gtg aag cct ggc ggc      48
Glu Val Gln Leu Val Glu Ser Gly Gly Gly Leu Val Lys Pro Gly Gly
1               5                   10                  15 tcc ctg agg ctg tcc tgt gag gcc tcc ggc ttc acc ttc tcc tcc tac      96
Ser Leu Arg Leu Ser Cys Glu Ala Ser Gly Phe Thr Phe Ser Ser Tyr
            20                  25                  30 acc ctg tcc tgg gtg agg cag acc cct ggc aag ggc ctg gag tgg gtg     144
Thr Leu Ser Trp Val Arg Gln Thr Pro Gly Lys Gly Leu Glu Trp Val
        35                  40                  45 gcc acc atc tcc atc ggc ggc agg tac acc tac tac cct gac tcc gtg     192
Ala Thr Ile Ser Ile Gly Gly Arg Tyr Thr Tyr Tyr Pro Asp Ser Val
50                  55                  60 aag ggc cgg ttc acc atc tcc cgg gac aac gcc aag aac acc ctg tac     240
Lys Gly Arg Phe Thr Ile Ser Arg Asp Asn Ala Lys Asn Thr Leu Tyr
65                  70                  75                  80 ctg cag atg aac tcc ctg aag tcc gag gac acc gcc atg tac tac tgt     288
Leu Gln Met Asn Ser Leu Lys Ser Glu Asp Thr Ala Met Tyr Tyr Cys
                85                  90                  95 acc cgg gac ttc aac ggc tac tcc gac ttc tgg ggc cag ggc acc aca     336
Thr Arg Asp Phe Asn Gly Tyr Ser Asp Phe Trp Gly Gln Gly Thr Thr
            100                 105                 110 ctg acc gtg tcc tcc                                                  351
Leu Thr Val Ser Ser
        115
```

<210> SEQ ID NO 72
<211> LENGTH: 117
<212> TYPE: PRT
<213> ORGANISM: Homo sapiens

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Glu Ala Ser Gly Phe Thr Phe Ser Ser Tyr
            20                  25                  30

Thr Leu Ser Trp Val Arg Gln Thr Pro Gly Lys Gly Leu Glu Trp Val
        35                  40                  45

Ala Thr Ile Ser Ile Gly Gly Arg Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Met Tyr Tyr Cys
                85                  90                  95

Thr Arg Asp Phe Asn Gly Tyr Ser Asp Phe Trp Gly Gln Gly Thr Thr
            100                 105                 110

Leu Thr Val Ser Ser
        115

<210> SEQ ID NO 73
<211> LENGTH: 36
<212> TYPE: DNA
<213> ORGANISM: Mus sp.

<400> SEQUENCE: 73
ggaggatcca tagacagatg ggggtgtcgt tttggc                              36

<210> SEQ ID NO 74
<211> LENGTH: 32
<212> TYPE: DNA
<213> ORGANISM: Mus sp.

```
<400> SEQUENCE: 74
ggaggatccc ttgaccaggc atcctagagt ca                                      32

<210> SEQ ID NO 75
<211> LENGTH: 32
<212> TYPE: DNA
<213> ORGANISM: Mus sp.
<220> FEATURE:
<221> NAME/KEY: misc_feature
<222> LOCATION: (1)..(32)
<223> OTHER INFORMATION: mixed bases are defined as follows: H=A+T+C,
      S=G+C, Y=C+T, K=G+T, M=A+C, R=A+G, W=A+T, V = A+C+G, N = A+C+G+T

<400> SEQUENCE: 75
cttccggaat tcsargtnma gctgsagsag tc                                      32

<210> SEQ ID NO 76
<211> LENGTH: 35
<212> TYPE: DNA
<213> ORGANISM: Mus sp.
<220> FEATURE:
<221> NAME/KEY: misc_feature
<222> LOCATION: (1)..(35)
<223> OTHER INFORMATION: mixed bases are defined as follows: H=A+T+C,
      S=G+C, Y=C+T, K=G+T, M=A+C, R=A+G, W=A+T, V = A+C+G, N = A+C+G+T

<400> SEQUENCE: 76
cttccggaat tcsargtnma gctgsagsag tcwgg                                   35

<210> SEQ ID NO 77
<211> LENGTH: 31
<212> TYPE: DNA
<213> ORGANISM: Mus sp.
<220> FEATURE:
<221> NAME/KEY: misc_feature
<222> LOCATION: (1)..(31)
<223> OTHER INFORMATION: mixed bases are defined as follows: H=A+T+C,
      S=G+C, Y=C+T, K=G+T, M=A+C, R=A+G, W=A+T, V = A+C+G, N = A+C+G+T

<400> SEQUENCE: 77
ggagctcgay attgtgmtsa cmcarwctmc a                                       31

<210> SEQ ID NO 78
<211> LENGTH: 46
<212> TYPE: DNA
<213> ORGANISM: Mus sp.

<400> SEQUENCE: 78
tatagagctc aagcttggat ggtgggaaga tggatacagt tggtgc                       46

<210> SEQ ID NO 79
<211> LENGTH: 21
<212> TYPE: DNA
<213> ORGANISM: Mus sp.

<400> SEQUENCE: 79
atggagtcac agattcaggt c                                                  21

<210> SEQ ID NO 80
<211> LENGTH: 32
<212> TYPE: DNA
<213> ORGANISM: Mus sp.

<400> SEQUENCE: 80
ttttgaattc cagtaacttc aggtgtccac tc                                      32
```

```
<210> SEQ ID NO 81
<211> LENGTH: 17
<212> TYPE: PRT
<213> ORGANISM: Homo sapiens

<400> SEQUENCE: 81

Thr Ile Tyr Pro Gly Asp Gly Asp Thr Gly Tyr Ala Gln Lys Phe Gln
1               5                   10                  15

Gly
```